US011136558B2

(12) United States Patent
Mabashi-Asazuma et al.

(10) Patent No.: US 11,136,558 B2

(45) Date of Patent: Oct. 5, 2021

(54) COMPOSITIONS AND METHODS FOR REDUCING FUCOSYLATION OF GLYCOPROTEINS IN INSECT CELLS AND METHODS OF USE THEREOF FOR PRODUCTION OF RECOMBINANT GLYCOPROTEINS

(71) Applicant: The University of Wyoming, Laramie, WY (US)

(72) Inventors: Hideaki Mabashi-Asazuma, Laramie, WY (US); Donald L. Jarvis, Laramie, WY (US)

(73) Assignee: THE UNIVERSITY OF WYOMING, Laramie, WY (US)

( * ) Notice: Subject to any disclaimer, the term of this patent is extended or adjusted under 35 U.S.C. 154(b) by 0 days.

(21) Appl. No.: 16/287,304

(22) Filed: Feb. 27, 2019

(65) Prior Publication Data

US 2019/0359952 A1 Nov. 28, 2019

Related U.S. Application Data

(63) Continuation of application No. 14/504,195, filed on Oct. 1, 2014, now abandoned.

(60) Provisional application No. 61/885,294, filed on Oct. 1, 2013.

(51) Int. Cl.

| | |
|---|---|
| ***C12N 9/04*** | (2006.01) |
| ***C12P 21/00*** | (2006.01) |
| ***C07K 16/28*** | (2006.01) |
| *A61K 38/00* | (2006.01) |

(52) U.S. Cl.

CPC ........ *C12N 9/0006* (2013.01); *C07K 16/2887* (2013.01); *C12P 21/005* (2013.01); *C12Y 101/01281* (2013.01); *A61K 38/00* (2013.01); *C07K 2317/14* (2013.01); *C07K 2317/24* (2013.01); *C07K 2317/41* (2013.01)

(58) Field of Classification Search

CPC .............. C12N 9/0006; C07K 16/2887; C12Y 101/01281

See application file for complete search history.

(56) References Cited

U.S. PATENT DOCUMENTS

| | | | | |
|---|---|---|---|---|
| 6,461,863 B1 * | 10/2002 | Jarvis | A61K 31/7048 435/320.1 |
| 2012/0214975 A1 * | 8/2012 | Sandig | C12P 21/005 530/395 |

OTHER PUBLICATIONS

Mabashi-Asazuma, H., et al., "A novel baculovirus vector for the production of nonfucosylated recombinant glycoproteins in insect cells" Glycobiology (2014) 24(3):325-40.

Ailor et al. N-glycan patterns of human transferrin produced in Trichoplusia ni insect cells: effects of mammalian galactosyltransferase. Glycobiology, 2000, 837-847,10.

Aumiller et al., A transgenic insect cell line engineered to produce CMP-sialic acid and sialylated glycoproteins, Glycobiology, 2003, 497-507, 13.

Aumiller et al., A new glycoengineered insect cell line with an inducibly mammalianized protein N-glycosylation pathway, Glycobiology, 2012, 417-428, 22.

Chang et al., Improvement of glycosylation in insect cells with mammalian glycosyltransferases, J Biotechnol., 2003, 61-71, 102.

Hill et al., Isolation and analysis of a baculovirus vector that supports recombinant glycoprotein sialylation by SfSWT-1 cells cultured in serum-free medium, Biotechnol Bioengr., 2006, 37-47, 95.

Hollister et al., Stable expression of mammalian β1,4-galactosyltransferase extends the N-glycosylation pathway in insect cells, Glycobiology, 1998, 473-480, 8.

Hollister et al., Engineering lepidopteran insect cells for sialoglycoprotein production by genetic transformation with mammalian β1,4-galactosyltransferase and α2,6-sialyltransferase genes, Glycobiology, 2001, 1-9, 11.

Jarvis et al., Use of early baculovirus promoters for continuous expression and efficient processing of foreign gene products in stably transformed lepidopteran cells, Nat Biotechnol., 1990, 950-955, 8.

Jarvis et al., Modifying the insect cell N-glycosylation pathway with immediate early baculovirus expression vectors. Nat Biotechnol., 1996, 1288-1292, 14.

Jefferis et al., Glycosylation as a strategy to improve antibody-based therapeutics, Nat Rev Drug Discov., 2009, 226-234, 8.

Mabashi-Asazuma et al., Impact of a human CMP-sialic acid transporter on recombinant glycoprotein sialylation in glycoengineered insect cells, Glycobiology, 2013, 199-210, 23.

Passarelli et al., Baculovirus late and very late gene regulation, Curr Drug Targets, 2007, 1103-1115, 8.

Rendic et al., Towards abolition of immunogenic structures in insect cells: characterization of a honey-bee (*Apis mellifera*) multi-gene family reveals both an allergy-related core α1,3-fucosyltransferase and the first insect Lewis-histo-blood-group-related antigen-synthesizing enzyme, Biochem J., 2007, 105-115, 402.

Satoh et al., Non-fucosylated therapeutic antibodies as next-generation therapeutic antibodies, Exp Op Biol Ther., 2006, 1161-1173, 6.

Shinkawa et al., The absence of fucose but not the presence of galactose or bisecting N-acetylglucosamine of human IgG1 complex-type oligosaccharides shows the critical role of enhancing antibody-dependent cellular cytotoxicity, J Biol Chem., 2003, 3466-3473, 278.

(Continued)

*Primary Examiner* — Antonio Galisteo Gonzalez

(74) *Attorney, Agent, or Firm* — Robert C. Netter, Jr.; Dann, Dorfman, Herrell & Skillman

(57) ABSTRACT

Compositions for reducing fucosylation of glycoproteins in insect cells are provided. Also disclosed are methods of use of such compositions for the production of recombinant humanized proteins.

21 Claims, 30 Drawing Sheets

Specification includes a Sequence Listing.

(56) References Cited

OTHER PUBLICATIONS

Tomiya et al., Complex-type biantennary N-glycans of recombinant human transferrin from Trichoplusia ni insect cells expressing mammalian β-1,4-galactosyltransferase and β-1,2-N-acetylglucosaminyltransferase II, Glycobiology, 2003, 23-24, 13.
Von Horsten et al., Production of non-fucosylated antibodies by co-expression of heterologous GDP-6-deoxy-D-lyxo-4-hexulose reductase, Glycobiology, 2010, 1607-1618, 20.
Wagner et al., Elongation of the N-glycans of fowl plague virus hemagglutinin expressed in Spodoptera frugiperda (Sf9) cells by coexpression of human β1,2-N-acetylglucosaminyltransferase I, Glycobiology, 1996, 165-175, 6.
Yamane-Ohnuki et al., Production of therapeutic antibodies with controlled fucosylation, MAbs, 2009, 230-236, 1.
Palmberger et al., Minimizing fucosylation in insect cell-derived glycoproteins reduces binding to IgE antibodies from the sera of patients with allergy, Biotechnol J., 2014, 1206-1214, 9(9).

* cited by examiner

Plasmid map of pΔChi/Cath-EGFP/RMD

FIG. 14B

Sequence of pΔChi/Cath-EGFP/RMD: It contains AcMNPV *hr5* enhancer sequence (yellow, 201-11555), AcMNPV IE1 promoter sequences (purple, 239-835, 10958-11554), codon-optimized RMD coding sequence (red, 10034-10948), and EGFP coding sequence (green, 845-1564).pΔChi/Cath-EGFP/RMD (11884 bp)

5'- ttacacgtagaattctactcgtaaagcagtttatgagcccgtgtgcaaaacatgacatcatctcgatttgaaaaacaaatgaccatcatccactcg
atcgtgcgttacaagtagaattctactcgtaaagccagttcggttatgagccgtgtgcaaaacatgacatcagcttatgactcatacttgattgtgt
tttacgcgaagggcgaattccagcacactggcggccgttactagacgatgtctttgtgatgcgcgcgacatttttgtaggttattgataaaatgaa
cggatacgttgcccgacattatcattaaatccttggcgtagaatttgtcgggtccattgtccgtgtgcgctagcatgcccgtaacggacctcgtact
tttggcttcaaaggttttgcgcacagacaaaatgtgccacacttgcagctctgcatgtgtgcgcgttaccacaaatcccaacggcgcagtgtactt
gttgtatgcaaataaatctcgataaaggcgcggcgcgcgaatgcagctgatcacgtacgctcctcgtgttccgttcaaggacggtgttatcgacct
cagattaatgtttatcggccgactgttttcgtatccgctcaccaaacgcgtttttgcattaacattgtatgtcggcggatgttctatatctaatttgaa
taaataaacgataaccgcgttggttttagagggcataataaaagaaatattgttatcgtgttcgccattagggcagtataaattgacgttcatgtt
ggatattgtttcagttgcaagttgacactggcggcgacaagatcgtgaacaaccaagtgaccggtaccaccatggtgagcaagggcgaggagc
tgttcaccggggtggtgcccatcctggtcgagctggacggcgacgtaaacggccacaagttcagcgtgtccggcgagggcgagggcgatgcca
cctacggcaagctgaccctgaagttcatctgcaccaccggcaagctgcccgtgccctggcccaccctcgtgaccaccctgacctacggcgtgcag
tgcttcagccgctaccccgaccacatgaagcagcacgacttcttcaagtccgccatgcccgaaggctacgtccaggagcgcaccatcttcttcaa
ggacgacggcaactacaagacccgcgccgaggtgaagttcgagggcgacaccctggtgaaccgcatcgagctgaagggcatcgacttcaagg
aggacggcaacatcctggggcacaagctggagtacaactacaacagccacaacgtctatatcatggccgacaagcagaagaacggcatcaag
gtgaacttcaagatccgccacaacatcgaggacggcagcgtgcagctcgccgaccactaccagcagaacacccccatcggcgacggccccgtg
ctgctgcccgacaaccactacctgagcacccagtccgccctgagcaaagaccccaacgagaagcgcgatcacatggtcctgctggagttcgtga
ccgccgccgggatcactctcggcatggacgagctgtacaagtaatcgaaacgcctcgactgtgccttctagttgccagccatctgttgtttgcccct
cccccgtgccttccttgaccctggaaggtgccactcccactgtcctttcctaataaaatgaggaaattgcatcgcattgtctgagtaggtgtcattct
attctggggggtggggtggggcaggacagcaagggggaggattgggaagacaatagcaggcatgctggggaactagtgtggcggcgctaaac
aagaaatagccccggtggccaagagtatgcccgttcctcctacttttaagctaattcgactggcgtcgtctcaacaaagtcactagcgtaaaaa
tcagggcatgtgtggcgcctgctgggcgtttgccactctggctagtttggaaagtcaatttgcaatcaaacataaccagttgattaatctgtcgga
gcagcaaatgatcgattgtgattttgtcgacgctggctgtaacggcggcttgttgcacacagcgttcgaagccatcattaaaatgggcggcgtac
agctggaaagcgactatccatacgaagcagacaataacaattgccgtatgaactccaataagtttctagttcaagtaaaagattgttatagatac
attaccgtgtacgaggaaaaacttaaagatttgttacgccttgtcggccctattcctatggccatagacgctgccgacattgttaactataaacag
ggtattataaaatattgtttcaacagcggtctaaaccatgcggttcttttagtgggttatggtgttgaaaacaacattccatattggacctttaaaa
acacttggggcacggattggggagaggacggatttttcagggtacaacaaaacataaacgcctgtggtatgagaaacgaacttgcgtctactgc
agtcatttattaatctcaacacactcgctatttggaacataatcatatcgtctcagtagctcaaggtagagcgtagcgctctggatcgtatagatct
tgctaaggttgtgagttcaagtctcgcctgagatattaaaaaactttgtaattttaaaaattttattttataatatacaattaaaaactatacaatttt
ttattattacattaataatgatacaatttttattattacatttaatattgtctattacggtttctaatcatacagtacaaaaataaaatcacaattaat
ataattacaaagttaactacatgaccaaacatgaacgaagtcaatttagcggccaattcgccttcagccatggaagtgatatcgctcagactggt
gccgacgccgccaaacttggtgttctccatggtggttatgaggttgctttttttgttgggcaataaacgaccagccgctggcatctttccaactgtcgt
gataggtcgtgttgccgatggtcgggatccaaaactcgacgtcgtcgtcaattgctagttccttgtagttgctaaaatctatgcattgcgacgagtc
cgtgttggccacccaacgcccttctttgtagatgctgttgttgtagcaattactggtgtgtgccggcggattggtgcacggcatcagcaaaaacgt
gtcgtccgacaaaaaatgttgaagaaacagagttgttcatgagattgccaatcaaacgctcgtccaccttggccacggagactatcaggtcgtgca
gcatattgtttagcttgttgatgtgcgcatgcatcagctcaatgttcattttcagcaaatcgttttcgtacatcagctcctcttgaatatgcatcaggt
cgcctttggtggcagtgtctccctctgt

FIG. 14C gtacttggctctaacgttgtggcgccaagtgggcggccgcttcttgactcggtgctcgactttgcgtttaatgcatctgttaaacttgcagttccacg
tgtttttagaaagatcatatatatcattgtcaatcaaacagtgttcgcgtgtcaccgactcggggttatttttgtcatctttaatgagcagacacgca
gcttttatttggcgcgtggtgaacgtagacttttgtttgagaatcatactcacgccgtctcgatgaagcacagtgtccacggtcacgttgatggggt
tgccctcagcgtccaaaatgtatacctggcactcgtccgtgtcgtcctggcactcgagcctgctgtacattttcgaagtggaaatgccgcatcgcc
acgatttgttgcacgtgtggtgcgcaaagtgattgttattctgccgcttcaccaactctttgcctttgacccactggccgcggccctcgttgtcgcga
aaacagtcgtcgctgtcactgccccaacggtcgatcagctcttcgcccacctcgcactgctgcctgatgctccacataagcaaatcctctttgccca
cattcagcgttttcatggtttcttcgacgcgtgtgttgggatccagcgagccgccgttgtacgcatacgcctggtagtaccccttgtagccgataat
cacgttttcgttgtagtccgtctccacgatggtgatttccacgtccttttgcagcgtttccttgggcggggtaatgtccaagtttttaatcttgtacgg
acccgtcttcatttgcgcgttgcagtgctccgccgcaaaggcagaatgcgccgccgccgccaaaagcacatataaaacaatagcgcttaccatct
tgctaatcccgcggccatggcggccgggagcatgcgacgtcgggcccaattcgccctatagtgagtcgtattacaattcactggccgtcgttttac
aacgtcgtgactgggaaaaccctggcgttacccaacttaatcgccttgcagcacatccccctttcgccagctggcgtaatagcgaagaggcccgc
accgatcgcccttcccaacagttgcgcagcctgaatggcgaatggacgcgccctgtagcggcgcattaagcgcggcgggtgtggtggttacgcg
cagcgtgaccgctacacttgccagcgccctagcgcccgctcctttcgctttcttcccttcctttctcgccacgttcgccggctttccccgtcaagctct
aaatcgggggctccctttagggttccgatttagtgctttacggcacctcgaccccaaaaaacttgattagggtgatggttcacgtagtgggccatc
gccctgatagacggtttttcgccctttgacgttggagtccacgttctttaatagtggactcttgttccaaactggaacaacactcaaccctatctcgg
tctattcttttgatttataagggattttgccgatttcggcctattggttaaaaaatgagctgatttaacaaaaatttaacgcgaattttaacaaaata
ttaacgcttacaatttcctgatgcggtattttctccttacgcatctgtgcggtatttcacaccgcatcaggtggcacttttcggggaaatgtgcgcgg
aacccctatttgtttatttttctaaatacattcaaatatgtatccgctcatgagacaataaccctgataaatgcttcaataatattgaaaaaggaag
agtatgagtattcaacatttccgtgtcgcccttattcccttttttgcggcattttgccttcctgtttttgctcacccagaaacgctggtgaaagtaaaa
gatgctgaagatcagttgggtgcacgagtgggttacatcgaactggatctcaacagcggtaagatccttgagagttttcgccccgaagaacgttt
tccaatgatgagcacttttaaagttctgctatgtggcgcggtattatcccgtattgacgccgggcaagagcaactcggtcgccgcatacactattct
cagaatgacttggttgagtactcaccagtcacagaaaagcatcttacggatggcatgacagtaagagaattatgcagtgctgccataaccatga
gtgataacactgcggccaacttacttctgacaacgatcggaggaccgaaggagctaaccgcttttttgcacaacatgggggatcatgtaactcgc
cttgatcgttgggaaccggagctgaatgaagccataccaaacgacgagcgtgacaccacgatgcctgtagcaatggcaacaacgttgcgcaaa
ctattaactggcgaactacttactctagcttcccggcaacaattaatagactggatggaggcggataaagttgcaggaccacttctgcgctcggc
ccttccggctggctggtttattgctgataaatctggagccggtgagcgtgggtctcgcggtatcattgcagcactggggccagatggtaagccctc
ccgtatcgtagttatctacacgacggggagtcaggcaactatggatgaacgaaatagacagatcgctgagataggtgcctcactgattaagcat
tggtaactgtcagaccaagtttactcatatatactttagattgatttaaaacttcatttttaatttaaaaggatctaggtgaagatcctttttgataat
ctcatgaccaaaatcccttaacgtgagttttcgttccactgagcgtcagaccccgtagaaaagatcaaaggatcttcttgagatcctttttttctgc
gcgtaatctgctgcttgcaaacaaaaaaaccaccgctaccagcggtggtttgtttgccggatcaagagctaccaactctttttccgaaggtaactg
gcttcagcagagcgcagataccaaatactgttcttctagtgtagccgtagttaggccaccacttcaagaactctgtagcaccgcctacatacctcg
ctctgctaatcctgttaccagtggctgctgccagtggcgataagtcgtgtcttaccgggttggactcaagacgatagttaccggataaggcgcagc
ggtcgggctgaacggggggttcgtgcacacagcccagcttggagcgaacgacctacaccgaactgagatacctacagcgtgagctatgagaaa
gcgccacgcttcccgaagggagaaaggcggacaggtatccggtaagcggcagggtcggaacaggagagcgcacgagggagcttccagggggg
aaacgcctggtatctttatagtcctgtcgggtttcgccacctctgacttgagcgtcgatttttgtgatgctcgtcaggggggcggagcctatggaaa
aacgccagcaacgcggcctttttacggttcctggccttttgctggccttttgctcacatgttctttcctgcgttatcccctgattctgtggataaccgta
ttaccgcctttgagtgagctgataccgctcgccgcagccgaacgaccgagcgcagcgagtcagtgagcgaggaagcggaagagcgcccaatac
gcaaaccgcctctccccgcgcgttggccgattcattaatgcagctggcacgacaggtttcccgactggaaagcgggcagtgagcgcaacgcaat
taatgtgagttagctcactcattaggcaccccaggctttacactttatgcttccggctcgtatgttgtgtggaattgtgagcggataacaatttcaca
caggaaacagctatgaccatgattacgccaagctatttaggtgacactatagaatactcaagctatgcatccaacgcgttgggagctctcccata
tggtcgacctgcaggcggccgcactagtgattatgggtttgtttgcgtgttgcacaaaatacacaaggctgtcgaccgacacaaaaatgaagttt
ccctatgttgcgttgtcgtacatcaacgtgacgctgtgcacctacaccg

FIG. 14D ccatgttggtgggatacatggtaacattcaatgactccagcgaattgaaatatttacaatactggttgctgttgtcgtttttgatgtccgtggtgcta
aacgctccgactctgtggacgatgctcaaaaccacagaagcccatgaagtaatttacgaaatgaagctgttccacgccatgtactttagtaacgt
gctgttgaattatgtggtgtttttggacaatcaaatgggtacaaattttgtttttgttaacaatttaattcactgttgtgtactttttatgatatttgttg
aattgcttatcctgttgggccacacaatgggcacgtacacggattatcaatatgtcaaatcgtgttatatggttatattgtttgtttcagttatgagt
gttactattgttatgggtttagagtgtttgaaaacgaaactaattgataacagtttgatgtttaacgcgtttgtgtgcgctttgtacattgtgattgca
ataatgtggtctttaaaaaataatttgactagttattacgtttcaaatttacaaagtattcaagttgttccgttttcatacaacgatccgccgccacc
gttctctaacattgtaatggatgacataaaaaataaaaaataatttataaaaatgtttttattctttcacaattctgtaaattctaaacaaaaaat
ataaatacaaacttattatgttgtcgtctaaataaacatcaatttgtaaatctggacacctattcatatcattgatattacagtctactatacaacaa
ttaaaactaaccaaattatctttacaacaattaaagcaattaaaacaatttaaataatcttcattgtcgtcgtataagtttatttgcactgtagacg
gtgttacacagcgatccattcgacgttcgtgttcgatcaactttctcgccaacttgtaccataaaaattgtttggacaaaaagttttccaacaatgg
taacggccaattcaacgtgacgatgcgcacgtcctcgggtatgcatttgttaaaaaacacacagctcgctttaccaaacgaaagcaaaggtact
aaatatggcgccattggctgatttgttattccaagataattacaaataaactgatccgtcgtggggtgataactggcaggtgtcagctttaaataa
tcttcaacgttgttgtcgcgcaaaagtctgcattttacacgcgttgttaatcccacgacttttgcatgtaaaatcggatccaaatactgcagaatcg
tgtctataatttctaatggtaaacgtatgcgttttgctcgtgggcgctttgtaacgctcgacatcctaataacaactaacacaaaactaaaatgata
ctcaatatattgcttttacagttcatctttaggtttaaactgtgcgtttatcgcgttgagcaagtcgccgttatcggcatcaatctcccaagcaaaca
ggccgcccaatttatttcggtcgacatatttaacttttcctaacacagagtcgacgctgtcaaacgaaatcaaatcacctttacttttatcgaaaac
gtacgacgcttgagcggcgctgtcaaacgtgtacacataattgttgagatctttttgaatttgacgataatctacaacaccgtcctcccacgtgccc
gaccccggcccgttgccagtgccggaaaaatagttgtcattcgtataatttgttacgccggtccagccgcggccgtacatggcgacgcccacaat
tattttgttgggatcgacgccttgtttcagtaacgcatcgacagcgtagtgtgtagtgtatagctcttccgagttccaacttggcgcgtagactgttg
tttggtagcccaaatccgtgtttgaccaagcccctttaaaatcgtaactcatgagaaatattttgcctaatgacttttgcgcttcggcgtagtttacc
acggcaatcttgtcgtaacccgcgcttatagcgcttgttaattcgtaaaccctgccggtttgcgcttcgaggtcgtctagcattgcgcgcagctcctc
caacaacaaaatgtatgttttggcgtcaccgtccgcatcgcccaacgacgggttagcccctttgccgcccggaaactcccaatcgatgtctacac
cgtcaaagaatttccacacttgcagaaattccttaaccgaatctacaaaaacgtttctttttttcaacatcgtgcataaaataaaatgggtctgata
gagtccagcctcctattgaaggaagaatttttaaatgggggtttgctaattttgccgccatcaactgtccaaaattgcctttatacggctcgttcca
agcggacacacctttttggggtttttgtacggcggcccacggatcgtgaatggcaactttgaaatcttcgcgtcccttgcacgatctttgcaaagat
tcaaagctgatcctccccagcatgcctgctattgtcttcccaatcctccccttgctgtcctgccccaccccacccccccagaatagaatgacaccta
ctcagacaatgcgatgcaatttcctcattttattaggaaaggacagtgggagtggcaccttccagggtcaaggaaggcacgggggaggggcaa
acaacagatggctggcaactagaaggcacagtcgaggcgggcccttactcctctctaacacgagattcccaatcggacaggatggccctcagtg
attgtttgatagtgatttcgggtttccatccagtagtatcatggaggcggcatgagagcctctaacacgacgttgctcggcacgcctcattctggc
gggatcttgaacgatttccagctcaacttgagcaatatcggccaacagctcgatgagttcacgaatttttgttcttgtccagagcacacgttgtaa
acggctccggcctctccgtgggacaacagtctcaggtaagcagacagcacgtcttgaacgtccaagaagtccctcgacacgtcgatgtcaccaa
cttcgaggcggtttgcctggaggccttgtttcatcctagcaatttggcgagcagcagaagcgatcacgaacgaatcctttggccaggaccaatgt
ggttgaaaggacgggcaaccaaaacacgccagccctcagtgattccccattggagacacagagattcagcagccaatttggacacagcgtaag
ggttacgggcatgagggatgagttcctcgtgaatagcaaggcagcctcggccacttgaccgtacacatcaccggaggagatgtacaggaagg
ttccggagaatcctctagccttcagagcttggagcaagttcagtgttcccagcaggttgatttggagagtacgagcaggatcacggaatgcctcg
ggtacgtatgtttgaccagcgaggtgaataacagcatccggcaattcgggccacaaatcgcccaaagagtcgggttccaacaagtcgtagcggt
gaggaacagggagcaaagcccaaggtgtgtgagcagccgccaagtatgcctggaggtgtttaccgacgaagccagacagtcccgttacgaac
aagcgttgagtcatggttcgcgaggtcacttggttgttcacgatcttgtcgccgccagtgtcaacttgcaactgaaacaatatccaacatgaacgt
caatttatactgccctaatggcgaacacgataacaatatttctttattatgccctctaaaaccaacgcggttatcgtttatttattcaaattagatat
agaacatccgccgacatacaatgttaatgcaaaaacgcgtttggtgagcggatacgaaaacagtcggccgataaacattaatctgaggtcgat
aacaccgtccttgaacggaacacgaggagcgtacgtgatcagctgcattcgcgcgccgcgcctttatcgagatttatttgcatacaacaagtaca
ctgcgccgttgggatttgtggtaacgcgcacacatgcagagctgcaagt

FIG. 14E gtggcacattttgtctgtgcgcaaaacctttgaagccaaaagtacgaggtccgttacgggcatgctagcgcacacggacaatggacccgacaaa
ttctacgccaaggatttaatgataatgtcgggcaacgtatccgttcattttatcaataacctacaaaaatgtcgcgcgcatcacaaagacatcgac
gcgcgtagaattctacccgtaaagcgagtttagttatgagccatgtgcaaaacatgacatcagcttttatttttataacaaatgacatcatttcttg
attgtgttttacacgtagaattctactcgtaaagccgagagttcagttttgaaaaacaaatgacatcatctttttgattgtgctttacgagtagaatt
ctacccgtaaatcaagttcggttttgaaaaacaaatgagtcatattgtatgatatcatattgcaaaacaaatgactcatcaatcgatcgtgcg-3’

FIG. 15A pVL1393-polh-antiCD20-IgG sequence: It contains AcMNPV polyhedrin promoters (purple, 129-1, 227-355), anti-CD20-IgG heavy chain coding sequence (green, 367-1779), and anti-CD20-IgG light chain coding sequence (red, 12408-11701).

pVL1393-polh-antiCD20-IgG

5'- agcgcccgatggtgggacggtatgaataatccggaatatttataggtttttttattacaaaactgttacgaaaacagtaaaatacttatttatttgc
gagatggttatcattttaattatctccatgatgctagctgagtttcaaattggtaattggacccttcattaagatttcacacagatcagccgactgcg
aatagaaactcacctaggcactagtctcgagatcatggagataattaaaatgataaccatctcgcaaataaataagtattttactgttttcgtaac
agttttgtaataaaaaaacctataaatattccggattattcataccgtcccaccatcgggcgctgtttaaacaccatgggctggtccctgatcctgc
tgttcctggtggccgtggccacccgcgtgctgagccaggtgcagctgcagcagcccggcgccgagctggtgaagcccggcgcctccgtgaagat
gagctgcaaggccagcggctacaccttcacctcctacaatatgcactgggtgaagcagaccccgggccgcggcctggagtggatcggcgccatc
tacccgggcaacggcgatacctcctacaaccagaagttcaagggcaaggccaccctgaccgccgataagagctccagcaccgcctacatgcag
ctgtcctcgctgaccagcgaggacagcgccgtgtactactgcgcccgcagcacctactacggcggcgattggtacttcaacgtgtggggcgccgg
caccaccgtgaccgtgagcgccgccagcaccaagggcccctccgtgttcccgctggccccgtcgagcaagagcaccagcggcggcaccgccgc
cctgggctgcctggtgaaggattacttcccggagcccgtgaccgtgtcgtggaacagcggcgccctgaccagcggcgtgcacaccttcccagcc
gtgctgcagagctcgggcctgtactcgctgagcagcgtggtgaccgtgccgtcgagctcgctgggcacccagacctacatctgcaacgtgaacc
acaagccatccaataccaaggtggataagaaggccgagcccaagagctgcgacaagacccacacctgccccccctgcccggccccagagctg
ctgggcggcccatccgtgttcctgttcccccccgaagccgaaggacaccctgatgatcagccgcacccccgaggtgacctgcgtggtggtggatgt
gagccacgaggaccccgaggtgaagttcaactggtacgtggatggcgtggaggtgcacaacgccaagaccaagccccgcgaggagcagtaca
acagcacctaccgcgtggtgtcggtgctgaccgtgctgcaccaggattggctgaacggcaaggagtacaagtgcaaggtgtccaacaaggccct
gcccgccccgatcgagaagaccatctccaaggccaagggccagccacgcgagccgcaggtgtacaccctgccaccctcccgcgatgagctgac
caagaaccaggtgagcctgacctgcctggtgaagggcttctacccctcggatatcgccgtggagtgggagagcaacggccagccggagaacaa
ctacaagaccaccccacccgtgctggacagcgacggcagcttcttcctgtacagcaagctgaccgtggacaagtcgcgctggcagcagggcaa
cgtgttctcctgcagcgtgatgcacgaggccctgcacaaccactacacccagaagagcctgagcctgagccccggcaagtaacctgcagatctg
cctcgactgtgccttctagttgccagccatctgttgtttgcccctcccccgtgccttccttgaccctggaaggtgccactcccactgtcctttcctaat
aaaatgaggaaattgcatcgcattgtctgagtaggtgtcattctattctggggggtggggtggggcaggacagcaagggggaggattgggaag
acaatagcaggcatgctggggaggatctgatcctttcctgggacccggcaagaaccaaaaactcactctcttcaaggaaatccgtaatgttaaa
cccgacacgatgaagcttgtcgttggatggaaaggaaaagagttctacagggaaacttggacccgcttcatggaagacagcttccccattgtta
acgaccaagaagtgatggatgttttccttgttgtcaacatgcgtcccactagacccaaccgttgttacaaattcctggcccaacacgctctgcgttg
cgaccccgactatgtacctcatgacgtgattaggatcgtcgagccttcatgggtgggcagcaacaacgagtaccgcatcagcctggctaagaag
ggcggcggctgcccaataatgaaccttcactctgagtacaccaactcgttcgaacagttcatcgatcgtgtcatctgggagaacttctacaagccc
atcgtttacatcggtaccgactctgctgaagaggaggaaattctccttgaagtttccctggtgttcaaagtaaaggagtttgcaccagacgcacct
ctgttcactggtccggcgtattaaaacacgatacattgttattagtacatttattaagcgctagattctgtgcgttgttgatttacagacaattgttgt
acgtattttaataattcattaaatttataatctttagggtggtatgttagagcgaaaatcaaatgatttcagcgtctttatatctgaatttaaatatt
aaatcctcaatagatttgtaaaataggtttcgattagtttcaaacaagggttgtttttccgaaccgatggctggactatctaatggattttcgctcaa
cgccacaaaacttgccaaatcttgtagcagcaatctagctttgtcgatattcgtttgtgttttgttttgtaataaaggttcgacgtcgttcaaaatatt
atgcgcttttgtatttctttcatcactgtcgttagtgtacaattgactcgacgtaaacacgttaaataaagcttggacatatttaacatcgggcgtgt
tagctttattaggccgattatcgtcgtcgtcccaaccctcgtcgttagaagttgcttccgaagacgattttgccatagccacacgacgcctattaatt
gtgtcggctaacacgtccgcgatcaaatttgtagttgagctttttggaattatttctgattgcgggcgtttttgggcgggtttcaatctaactgtgccc
gattttaattcagacaacacgttagaaagcgatggtgcaggcggtggtaacatttcagacggcaaatctactaatggcggcggtggtggagctg
atgataaatctaccatcggtggaggcg

FIG. 15B caggcggggctggcggcggaggcggaggcggaggtggtggcggtgatgcagacggcggtttaggctcaaatgtctctttaggcaacacagtcg
gcacctcaactattgtactggtttcgggcgccgtttttggtttgaccggtctgagacgagtgcgatttttttcgtttctaatagcttccaacaattgtt
gtctgtcgtctaaaggtgcagcgggttgaggttccgtcggcattggtggagcgggcggcaattcagacatcgatggtggtggtggtggtggaggc
gctggaatgttaggcacgggagaaggtggtggcggcggtgccgccggtataatttgttctggtttagtttgttcgcgcacgattgtgggcaccggc
gcaggcgccgctggctgcacaacggaaggtcgtctgcttcgaggcagcgcttggggtggtggcaattcaatattataattggaatacaaatcgta
aaaatctgctataagcattgtaatttcgctatcgtttaccgtgccgatatttaacaaccgctcaatgtaagcaattgtattgtaaagagattgtctc
aagctccgcacgccgataacaagccttttcatttttactacagcattgtagtggcgagacacttcgctgtcgtcgacgtacatgtatgctttgttgtc
aaaaacgtcgttggcaagctttaaaatatttaaaagaacatctctgttcagcaccactgtgttgtcgtaaatgttgtttttgataatttgcgcttccg
cagtatcgacacgttcaaaaaattgatgcgcatcaattttgttgttcctattattgaataaataagattgtacagattcatatctacgattcgtcatg
gccaccacaaatgctacgctgcaaacgctggtacaattttacgaaaactgcaaaaacgtcaaaactcggtataaaataatcaacgggcgctttg
gcaaaatatctattttatcgcacaagcccactagcaaattgtatttgcagaaaacaatttcggcgcacaattttaacgctgacgaaataaaagttc
accagttaatgagcgaccacccaaattttataaaaatctattttaatcacggttccatcaacaaccaagtgatcgtgatggactacattgactgtc
ccgatttatttgaaacactacaaattaaaggcgagctttcgtaccaacttgttagcaatattattagacagctgtgtgaagcgctcaacgatttgc
acaagcacaatttcatacacaacgacataaaactcgaaaatgtcttatatttcgaagcacttgatcgcgtgtatgtttgcgattacggattgtgca
aacacgaaaactcacttagcgtgcacgacggcacgttggagtattttagtccggaaaaaattcgacacacaactatgcacgtttcgtttgactgg
tacgcggcgtgttaacatacaagttgctaaccggcggttcgtaatcatggtcatagctgtttcctgtgtgaaattgttatccgctcacaattccaca
caacatacgagccggaagcataaagtgtaaagcctggggtgcctaatgagtgagctaactcacattaattgcgttgcgctcactgcccgctttcc
agtcgggaaacctgtcgtgccagctgcattaatgaatcggccaacgcgcggggagaggcggtttgcgtattgggcgctcttccgcttcctcgctc
actgactcgctgcgctcggtcgttcggctgcggcgagcggtatcagctcactcaaaggcggtaatacggttatccacagaatcaggggataacg
caggaaagaacatgtgagcaaaaggccagcaaaaggccaggaaccgtaaaaaggccgcgttgctggcgtttttccataggctccgcccccctg
acgagcatcacaaaaatcgacgctcaagtcagaggtggcgaaacccgacaggactataaagataccaggcgtttccccctggaagctccctcg
tgcgctctcctgttccgaccctgccgcttaccggatacctgtccgcctttctcccttcgggaagcgtggcgctttctcatagctcacgctgtaggtatc
tcagttcggtgtaggtcgttcgctccaagctgggctgtgtgcacgaaccccccgttcagcccgaccgctgcgccttatccggtaactatcgtcttga
gtccaacccggtaagacacgacttatcgccactggcagcagccactggtaacaggattagcagagcgaggtatgtaggcggtgctacagagttc
ttgaagtggtggcctaactacggctacactagaaggacagtatttggtatctgcgctctgctgaagccagttaccttcggaaaaagagttggtag
ctcttgatccggcaaacaaaccaccgctggtagcggtggtttttttgtttgcaagcagcagattacgcgcagaaaaaaaggatctcaagaagatc
ctttgatcttttctacggggtctgacgctcagtggaacgaaaactcacgttaagggattttggtcatgagattatcaaaaaggatcttcacctagat
ccttttaaattaaaaatgaagttttaaatcaatctaaagtatatatgagtaaacttggtctgacagttaccaatgcttaatcagtgaggcacctatc
tcagcgatctgtctatttcgttcatccatagttgcctgactccccgtcgtgtagataactacgatacgggagggcttaccatctggccccagtgctg
caatgataccgcgagacccacgctcaccggctccagatttatcagcaataaaccagccagccggaagggccgagcgcagaagtggtcctgcaa
ctttatccgcctccatccagtctattaattgttgccgggaagctagagtaagtagttcgccagttaatagtttgcgcaacgttgttgccattgctaca
ggcatcgtggtgtcacgctcgtcgtttggtatggcttcattcagctccggttcccaacgatcaaggcgagttacatgatcccccatgttgtgcaaaa
aagcggttagctccttcggtcctccgatcgttgtcagaagtaagttggccgcagtgttatcactcatggttatggcagcactgcataattctcttact
gtcatgccatccgtaagatgcttttctgtgactggtgagtactcaaccaagtcattctgagaatagtgtatgcggcgaccgagttgctcttgcccgg
cgtcaatacgggataataccgcgccacatagcagaactttaaaagtgctcatcattggaaaacgttcttcggggcgaaaactctcaaggatctta
ccgctgttgagatccagttcgatgtaacccactcgtgcacccaactgatcttcagcatcttttactttcaccagcgtttctgggtgagcaaaaacag
gaaggcaaaatgccgcaaaaaagggaataagggcgacacggaaatgttgaatactcatactcttcctttttcaatattattgaagcatttatcag
ggttattgtctcatgagcggatacatatttgaatgtatttagaaaaataaacaaataggggttccgcgcacatttccccgaaaagtgccacctgac
gtctaagaaaccattattatcatgacattaacctataaaaataggcgtatcacgaggccctttcgtctcgcgcgtttcggtgatgacggtgaaaac
ctctgacacatgcagctcccggagacggtcacagcttgtc

FIG. 15C tgtaagcggatgccgggagcagacaagcccgtcagggcgcgtcagcgggtgttggcgggtgtcggggctggcttaactatgcggcatcagagc
agattgtactgagagtgcaccatatgcggtgtgaaataccgcacagatgcgtaaggagaaaataccgcatcaggcgccattcgccattcaggct
gcgcaactgttgggaagggcgatcggtgcgggcctcttcgctattacgccagctggcgaaagggggatgtgctgcaaggcgattaagttgggta
acgccagggttttcccagtcacgacgttgtaaaacgacggccagtgccaagctttactcgtaaagcgagttgaaggatcatatttagttgcgttta
tgagataagattgaaagcacgtgtaaaatgtttcccgcgcgttggcacaactatttacaatgcggccaagttataaaagattctaatctgatatgt
tttaaaacacctttgcggcccgagttgtttgcgtacgtgactagcgaagaagatgtgtggaccgcagaacagatagtaaaacaaaaccctagta
ttggagcaataatcgatttaaccaacacgtctaaatattatgatggtgtgcatttttttgcgggcgggcctgttatacaaaaaaattcaagtacctg
gccagactttgccgcctgaaagcatagttcaagaatttattgacacggtaaaagaatttacagaaaagtgtcccggcatgttggtgggcgtgcac
tgcacacacggtattaatcgcaccggttacatggtgtgcagatatttaatgcacaccctgggtattgcgccgcaggaagccatagatagattcga
aaaagccagaggtcacaaaattgaaagacaaaattacgttcaagatttattaatttaattaatattatttgcattctttaacaaatactttatccta
ttttcaaattgttgcgcttcttccagcgaaccaaaactatgcttcgcttgctccgtttagcttgtagccgatcagtggcgttgttccaatcgacggta
ggattaggccggatattctccaccacaatgttggcaacgttgatgttacgtttatgcttttggttttccacgtacgtcttttggccggtaatagccgta
aacgtagtgccgtcgcgcgtcacgcacaacaccggatgtttgcgcttgtccgcggggtattgaaccgcgcgatccgacaaatccacactttggc
aactaaatcggtgacctgcgcgtctttttctgcattatttcgtctttcttttgcatggtttcctggaagccggtgtacatgcggtttagatcagtcatg
acgcgcgtgacctgcaaatctttggcctcgatctgcttgtccttgatggcaacgatgcgttcaataaactcttgtttttaacaagttcctcggtttt
tgcgccaccaccgcttgcagcgcgtttgtgtgctcggtgaatgtcgcaatcagcttagtcaccaactgtttgctctcctcctcccgttgtttgatcgc
gggatcgtacttgccggtgcagagcacttgaggaattacttcttctaaaagccattcttgtaattctatggcgtaaggcaatttggacttcataatc
agctgaatcacgccggatttagtaatgagcactgtatgcggctgcaaatacagcgggtcgccccttttcacgacgctgttagaggtagggccccc
attttggatggtctgctcaaataacgatttgtatttattgtctacatgaacacgtatagctttatcacaaactgtatattttaaactgttagcgacgtc
cttggccacgaaccggacctgttggtcgcgctctagcacgtaccgcaggttgaacgtatcttctccaaatttaaattctccaattttaacgcgagcc
attttgatacacgtgtgtcgattttgcaacaactattgtttttaacgcaaactaaacttattgtggtaagcaataattaaatatgggggaacatgc
gccgctacaacactcgtcgttatgaacgcagacggcgccggtctcggcgcaagcggctaaaacgtgttgcgcgttcaacgcggcaaacatcgca
aaagccaatagtacagttttgatttgcatattaacggcgatttttaaattatcttatttaataaatagttatgacgcctacaactccccgcccgcgt
tgactcgctgcacctcgagcagttcgttgacgccttcctccgtgtggccgaacacgtcgagcgggtggtcgatgaccagcggcgtgccgcacgcg
acgcacaagtatctgtacaccgaatgatcgtcgggcgaaggcacgtcggcctccaagtggcaatattggcaaattcgaaaatatatacagttgg
gttgtttgcgcatatctatcgtggcgttgggcatgtacgtccgaacgttgatttgcatgcaagccgaaattaaatcattgcgattagtgcgattaaa
acgttgtacatcctcgcttttaatcatgccgtcgattaaatcgcgcaatcgagtcaagtgatcaaagtgtggaataatgttttctttgtattcccgag
tcaagcgcagcgcgtattttaacaaactagccatcttgtaagttagtttcatttaatgcaactttatccaataatatattatgtatcgcacgtcaaga
attaacaatgcgcccgttgtcgcatctcaacacgactatgatagagatcaaataaagcgcgaattaaatagcttgcgacgcaacgtgcacgatct
gtgcacgcgttccggcacgagctttgattgtaataagtttttacgaagcgatgacatgacccccgtagtgacaacgatcacgcccaaaagaactg
ccgactacaaaattaccgagtatgtcggtgacgttaaaactattaagccatccaatcgaccgttagtcgaatcaggaccgctggtgcgagaagc
cgcgaagtatggcgaatgcatcgtataacgtgtggagtccgctcattagagcgtcatgtttagacaagaaagctacatatttaattgatcccgatg
attttattgataaattgaccctaactccatacacggtattctacaatggcggggttttggtcaaaatttccggactgcgattgtacatgctgttaacg
gctccgcccactattaatgaaattaaaaattccaattttaaaaaacgcagcaagagaaacatttgtatgaaagaatgcgtagaaggaaagaaa
aatgtcgtcgacatgctgaacaacaagattaatatgcctccgtgtataaaaaaaatattgaacgatttgaaagaaaacaatgtaccgcgcggcg
gtatgtacaggaagaggtttatactaaactgttacattgcaaacgtggtttcgtgtgccaagtgtgaaaaccgatgtttaatcaaggctctgacgc
atttctacaaccacgactccaagtgtgtgggtgaagtcatgcatcttttaatcaaatcccaagatgtgtataaaccaccaaactgccaaaaaatg
aaaactgtcgacaagctctgtccgtttgctggcaactgcaagggtctcaatcctatttgtaattattgaataataaaacaattataaatgctaaatt
tgtttttattaacgatacaaaccaaacgcaacaagaacatttgtagtattatctataattgaaaacgcgtagttataatcgctgaggtaatattta
aaatcattttcaaatgattcacagttaatttgcgacaatataattttattttcacataaactagacgccttgtcgtcttcttcttcgtattccttctcttt
ttcatttttctcctcataaaaattaacatagttattatcgtat

FIG. 15D ccatatatgtatctatcgtatagagtaaatttttttgttgtcataaatatatatgtctttttttaatggggtgtatagtaccgctgcgcatagtttttctgt
aatttacaacagtgctattttctggtagttcttcggagtgtgttgctttaattattaaatttatataatcaatgaatttgggatcgtcggttttgtacaa
tatgttgccggcatagtacgcagcttcttctagttcaattacaccatttttagcagcaccggattaacataactttccaaaatgttgtacgaaccgt
taaacaaaaacagttcacctcccttttctatactattgtctgcgagcagttgtttgttgttaaaaataacagccattgtaatgagacgcacaaacta
atatcacaaactggaaatgtctatcaatatatagttgctgatatctccccagcatgcctgctattgtcttcccaatcctcccccttgctgtcctgcccc
accccaccccccagaatagaatgacacctactcagacaatgcgatgcaatttcctcattttattaggaaaggacagtgggagtggcaccttccag
ggtcaaggaaggcacgggggaggggcaaacaacagatggctggcaactagaaggcacagtcgaggcgaattcttagcactcgccgcggttga
aggacttggtcaccgggctcgacaggccctggtgggtcacctcgcaggcgtacaccttgtgcttctcgtaatcggccttggacagggtcagggtg
gagctcagcgagtaggtgctatccttggaatcctgctcggtcacgctctcctggaagttgccggactgcagggcgttatccaccttccactgcacc
ttggcctcgcgggggtagaagttgttcagcaggcacaccacggaggcggtgccggacttcagctgctcgtccgacggcgggaagatgaacacg
gagggggcggccacggtgcgcttgatctccagcttggtgccgccgccgaaggtcgggggttgctggtccactgctggcagtagtaggtggcgg
catcctcggcctccacgcgggagatggtcaggctgtaggaggtgccgctgccgctgccggagaagcgcaccggcacgccggaggccagattgg
aggtggcgtagatccagggcttcggggagctgcctggcttctgctggaaccagtgaatgtagctcacgctggaggaggcgcggcaggtcatggt
caccttctcgcccggcgaggcgctcaggatggcggggctctgcgacagcacgatctggccgcggctcatgatcacggaggcgctgatcagcagg
aaggagatgatctgcacctggaaatccatggtggcggccgc-3′

FIG. 16A pVL1393-p6.9-antiCD20-IgG sequence: It contains AcMNPV p6.9 promoters (purple, 342-18, 440-764), anti-CD20-IgG heavy chain coding sequence (green, 776-2188), and anti-CD20-IgG light chain coding sequence (red, 5-12110).

pVL1393-p6.9-antiCD20-IgG:

5'-
tccatggtggcggccgcgtttaaattgtgtaatttatgtagctgtaatttttaccttattaatatttttacgctttgcattcgacgactgaactcccaa
atatatgtttaactcgtcttggtcgtttgaattttgttgctgtgtttcctaatatttccatcaccttaaatatgttattgtaatcctcaatgttgaactt
gcaattggacacggcatagttttccatagtcgtgtaaaacatggtattggctgcattgtaatacatccgactgagcgggtacggatctatgtgtttg
agcagcctgttcaaaaactctgcatcgtcgcaaaacggaatttgctagctgagtttcaaattggtaattggacccttcattaagatttcacacaga
tcagccgactgcgaatagaaactcacctaggcactagtctcgagaaattccgttttgcgacgatgcagagtttttgaacaggctgctcaaacaca
tagatccgtacccgctcagtcggatgtattacaatgcagccaataccatgttttacacgactatggaaaactatgccgtgtccaattgcaagttca
acattgaggattacaataacatatttaaggtgatggaaaatattaggaaacacagcaacaaaaattcaaacgaccaagacgagttaaacatat
atttgggagttcagtcgtcgaatgcaaagcgtaaaaaatattaataaggtaaaaattacagctacataaattacacaatttaaacgtttaaacac
catgggctggtccctgatcctgctgttcctggtggccgtggccacccgcgtgctgagccaggtgcagctgcagcagcccggcgccgagctggtga
agcccggcgcctccgtgaagatgagctgcaaggccagcggctacaccttcacctcctacaatatgcactgggtgaagcagaccccgggccgcg
gcctggagtggatcggcgccatctacccgggcaacggcgatacctcctacaaccagaagttcaagggcaaggccaccctgaccgccgataaga
gctccagcaccgcctacatgcagctgtcctcgctgaccagcgaggacagcgccgtgtactactgcgcccgcagcacctactacggcggcgattg
gtacttcaacgtgtggggcgccggcaccaccgtgaccgtgagcgccgccagcaccaagggcccctccgtgttcccgctggccccgtcgagcaag
agcaccagcggcggcaccgccgccctgggctgcctggtgaaggattacttcccggagcccgtgaccgtgtcgtggaacagcggcgccctgacca
gcggcgtgcacaccttcccagccgtgctgcagagctcgggcctgtactcgctgagcagcgtggtgaccgtgccgtcgagctcgctgggcacccag
acctacatctgcaacgtgaaccacaagccatccaataccaaggtggataagaaggccgagcccaagagctgcgacaagacccacacctgccc
cccctgcccggccccagagctgctgggcggcccatccgtgttcctgttccccccgaagccgaaggacaccctgatgatcagccgcacccccgag
gtgacctgcgtggtggtggatgtgagccacgaggaccccgaggtgaagttcaactggtacgtggatggcgtggaggtgcacaacgccaagacc
aagccccgcgaggagcagtacaacagcacctaccgcgtggtgtcggtgctgaccgtgctgcaccaggattggctgaacggcaaggagtacaag
tgcaaggtgtccaacaaggccctgcccgccccgatcgagaagaccatctccaaggccaagggccagccacgcgagccgcaggtgtacaccctg
ccaccctcccgcgatgagctgaccaagaaccaggtgagcctgacctgcctggtgaagggcttctacccctcggatatcgccgtggagtgggaga
gcaacggccagccggagaacaactacaagaccacccccacccgtgctggacagcgacggcagcttcttcctgtacagcaagctgaccgtggaca
agtcgcgctggcagcagggcaacgtgttctcctgcagcgtgatgcacgaggccctgcacaaccactacacccagaagagcctgagcctgagcc
ccggcaagtaacctgcagatctgcctcgactgtgccttctagttgccagccatctgttgtttgcccctcccccgtgccttccttgaccctggaaggtg
ccactcccactgtcctttcctaataaaatgaggaaattgcatcgcattgtctgagtaggtgtcattctattctggggggtggggtggggcaggaca
gcaagggggaggattgggaagacaatagcaggcatgctggggaggatctgatcctttcctgggacccggcaagaaccaaaaactcactctctt
caaggaaatccgtaatgttaaacccgacacgatgaagcttgtcgttggatggaaaggaaaagagttctacagggaaacttggacccgcttcatg
gaagacagcttccccattgttaacgaccaagaagtgatggatgttttccttgttgtcaacatgcgtcccactagacccaaccgttgttacaaattcc
tggcccaacacgctctgcgttgcgaccccgactatgtacctcatgacgtgattaggatcgtcgagccttcatgggtgggcagcaacaacgagtac
cgcatcagcctggctaagaagggcggcggctgcccaataatgaaccttcactctgagtacaccaactcgttcgaacagttcatcgatcgtgtcat
ctgggagaacttctacaagcccatcgtttacatcggtaccgactctgctgaagaggaggaaattctccttgaagtttccctggtgttcaaagtaaa
ggagtttgcaccagacgcacctctgttcactggtccggcgtattaaaacacgatacattgttattagtacatttattaagcgctagattctgtgcgtt
gttgatttacagacaattgttgtacgtattttaataattcattaaatttataatctttagggtggtatgttagagcgaaaatcaaatgattttcagcgt
ctttatatctgaattta

FIG. 16B aatattaaatcctcaatagatttgtaaaataggtttcgattagtttcaaacaagggttgtttttccgaaccgatggctggactatctaatggattttc
gctcaacgccacaaaacttgccaaatcttgtagcagcaatctagctttgtcgatattcgtttgtgttttgttttgtaataaaggttcgacgtcgttca
aaatattatgcgcttttgtatttctttcatcactgtcgttagtgtacaattgactcgacgtaaacacgttaaataaagcttggacatatttaacatcg
ggcgtgttagctttattaggccgattatcgtcgtcgtcccaaccctcgtcgttagaagttgcttccgaagacgattttgccatagccacacgacgcc
tattaattgtgtcggctaacacgtccgcgatcaaatttgtagttgagctttttggaattatttctgattgcgggcgtttttgggcgggtttcaatctaa
ctgtgcccgattttaattcagacaacacgttagaaagcgatggtgcaggcggtggtaacatttcagacggcaaatctactaatggcggcggtggt
ggagctgatgataaatctaccatcggtggaggcgcaggcggggctggcggcggaggcggaggcggaggtggtggcggtgatgcagacggcgg
tttaggctcaaatgtctctttaggcaacacagtcggcacctcaactattgtactggtttcgggcgccgtttttggtttgaccggtctgagacgagtgc
gatttttttcgtttctaatagcttccaacaattgttgtctgtcgtctaaaggtgcagcgggttgaggttccgtcggcattggtggagcgggcggcaat
tcagacatcgatggtggtggtggtggtggaggcgctggaatgttaggcacgggagaaggtggtggcggcggtgccgccggtataatttgttctg
gtttagtttgttcgcgcacgattgtgggcaccggcgcaggcgccgctggctgcacaacggaaggtcgtctgcttcgaggcagcgcttggggtggt
ggcaattcaatattataattggaatacaaatcgtaaaaatctgctataagcattgtaatttcgctatcgtttaccgtgccgatatttaacaaccgct
caatgtaagcaattgtattgtaaagagattgtctcaagctccgcacgccgataacaagccttttcatttttactacagcattgtagtggcgagaca
cttcgctgtcgtcgacgtacatgtatgctttgttgtcaaaaacgtcgttggcaagctttaaaatatttaaaagaacatctctgttcagcaccactgtg
ttgtcgtaaatgttgtttttgataatttgcgcttccgcagtatcgacacgttcaaaaaattgatgcgcatcaattttgttgttcctattattgaataaat
aagattgtacagattcatatctacgattcgtcatggccaccacaaatgctacgctgcaaacgctggtacaattttacgaaaactgcaaaaacgtc
aaaactcggtataaaataatcaacgggcgctttggcaaaatatctattttatcgcacaagcccactagcaaattgtatttgcagaaaacaatttc
ggcgcacaattttaacgctgacgaaataaaagttcaccagttaatgagcgaccacccaaattttataaaatctattttaatcacggttccatcaa
caaccaagtgatcgtgatggactacattgactgtcccgatttatttgaaacactacaaattaaaggcgagctttcgtaccaacttgttagcaatatt
attagacagctgtgtgaagcgctcaacgatttgcacaagcacaatttcatacacaacgacataaaactcgaaaatgtcttatatttcgaagcact
tgatcgcgtgtatgtttgcgattacggattgtgcaaacacgaaaactcacttagcgtgcacgacggcacgttggagtattttagtccggaaaaaat
tcgacacacaactatgcacgtttcgtttgactggtacgcggcgtgttaacatacaagttgctaaccggcggttcgtaatcatggtcatagctgtttc
ctgtgtgaaattgttatccgctcacaattccacacaacatacgagccggaagcataaagtgtaaagcctggggtgcctaatgagtgagctaactc
acattaattgcgttgcgctcactgcccgctttccagtcgggaaacctgtcgtgccagctgcattaatgaatcggccaacgcgcggggagaggcgg
tttgcgtattgggcgctcttccgcttcctcgctcactgactcgctgcgctcggtcgttcggctgcggcgagcggtatcagctcactcaaaggcggta
atacggttatccacagaatcaggggataacgcaggaaagaacatgtgagcaaaaggccagcaaaaggccaggaaccgtaaaaaggccgcgt
tgctggcgtttttccataggctccgcccccctgacgagcatcacaaaaatcgacgctcaagtcagaggtggcgaaacccgacaggactataaag
ataccaggcgtttccccctggaagctccctcgtgcgctctcctgttccgaccctgccgcttaccggatacctgtccgcctttctcccttcgggaagcg
tggcgctttctcatagctcacgctgtaggtatctcagttcggtgtaggtcgttcgctccaagctgggctgtgtgcacgaaccccccgttcagcccga
ccgctgcgccttatccggtaactatcgtcttgagtccaacccggtaagacacgacttatcgccactggcagcagccactggtaacaggattagca
gagcgaggtatgtaggcggtgctacagagttcttgaagtggtggcctaactacggctacactagaaggacagtatttggtatctgcgctctgctg
aagccagttaccttcggaaaaagagttggtagctcttgatccggcaaacaaaccaccgctggtagcggtggtttttttgtttgcaagcagcagatt
acgcgcagaaaaaaaggatctcaagaagatcctttgatcttttctacggggtctgacgctcagtggaacgaaaactcacgttaagggattttggt
catgagattatcaaaaaggatcttcacctagatccttttaaattaaaaatgaagttttaaatcaatctaaagtatatatgagtaaacttggtctgac
agttaccaatgcttaatcagtgaggcacctatctcagcgatctgtctatttcgttcatccatagttgcctgactccccgtcgtgtagataactacgat
acgggagggcttaccatctggccccagtgctgcaatgataccgcgagacccacgctcaccggctccagatttatcagcaataaaccagccagcc
ggaagggccgagcgcagaagtggtcctgcaactttatccgcctccatccagtctattaattgttgccgggaagctagagtaagtagttcgccagtt
aatagtttgcgcaacgttgttgccattgctacaggcatcgtggtgtcacgctcgtcgtttggtatggcttcattcagctccggttcccaacgatcaag
gcgagttacatgatcccccatgttgtgcaaaaaagcggttagctccttcggtcctccgatcgttgtcagaagtaagttggccgcagtgttatcactc
atggttatggcagcactgcataattctcttactgtcatgccatccgtaagatgcttttctgtgactggtgagtactcaaccaagtcattctgagaata
gtgtatgcggcgaccgagttgctcttgcccggcgtcaa

FIG. 16C tacgggataataccgcgccacatagcagaactttaaaagtgctcatcattggaaaacgttcttcggggcgaaaactctcaaggatcttaccgctg
ttgagatccagttcgatgtaacccactcgtgcacccaactgatcttcagcatcttttactttcaccagcgtttctgggtgagcaaaaacaggaagg
caaaatgccgcaaaaaagggaataagggcgacacggaaatgttgaatactcatactcttcctttttcaatattattgaagcatttatcagggttat
tgtctcatgagcggatacatatttgaatgtatttagaaaaataaacaaataggggttccgcgcacatttccccgaaaagtgccacctgacgtcta
agaaaccattattatcatgacattaacctataaaaataggcgtatcacgaggccctttcgtctcgcgcgtttcggtgatgacggtgaaaacctctg
acacatgcagctcccggagacggtcacagcttgtctgtaagcggatgccgggagcagacaagcccgtcagggcgcgtcagcgggtgttggcgg
gtgtcggggctggcttaactatgcggcatcagagcagattgtactgagagtgcaccatatgcggtgtgaaataccgcacagatgcgtaaggaga
aaataccgcatcaggcgccattcgccattcaggctgcgcaactgttgggaagggcgatcggtgcgggcctcttcgctattacgccagctggcgaa
agggggatgtgctgcaaggcgattaagttgggtaacgccagggttttcccagtcacgacgttgtaaaacgacggccagtgccaagctttactcgt
aaagcgagttgaaggatcatatttagttgcgtttatgagataagattgaaagcacgtgtaaaatgtttcccgcgcgttggcacaactatttacaat
gcggccaagttataaaagattctaatctgatatgttttaaaacacctttgcggcccgagttgtttgcgtacgtgactagcgaagaagatgtgtgga
ccgcagaacagatagtaaaacaaaaccctagtattggagcaataatcgatttaaccaacacgtctaaatattatgatggtgtgcatttttttgcgg
gcgggcctgttatacaaaaaaattcaagtacctggccagactttgccgcctgaaagcatagttcaagaatttattgacacggtaaaagaatttac
agaaaagtgtcccggcatgttggtgggcgtgcactgcacacacggtattaatcgcaccggttacatggtgtgcagatatttaatgcacaccctgg
gtattgcgccgcaggaagccatagatagattcgaaaaagccagaggtcacaaaattgaaagacaaaattacgttcaagatttattaatttaatt
aatattatttgcattctttaacaaatactttatcctattttcaaattgttgcgcttcttccagcgaaccaaaactatgcttcgcttgctccgtttagctt
gtagccgatcagtggcgttgttccaatcgacggtaggattaggccggatattctccaccacaatgttggcaacgttgatgttacgtttatgcttttg
gttttccacgtacgtcttttggccggtaatagccgtaaacgtagtgccgtcgcgcgtcacgcacaacaccggatgtttgcgcttgtccgcggggtat
tgaaccgcgcgatccgacaaatccaccactttggcaactaaatcggtgacctgcgcgtctttttctgcattatttcgtctttcttttgcatggtttcct
ggaagccggtgtacatgcggtttagatcagtcatgacgcgcgtgacctgcaaatctttggcctcgatctgcttgtccttgatggcaacgatgcgttc
aataaactcttgtttttaacaagttcctcggtttttgcgccaccaccgcttgcagcgcgtttgtgtgctcggtgaatgtcgcaatcagcttagtcac
caactgtttgctctcctcctcccgttgtttgatcgcgggatcgtacttgccggtgcagagcacttgaggaattacttcttctaaaagccattcttgta
attctatggcgtaaggcaatttggacttcataatcagctgaatcacgccggatttagtaatgagcactgtatgcggctgcaaatacagcgggtcg
ccccttttcacgacgctgttagaggtagggcccccattttggatggtctgctcaaataacgatttgtatttattgtctacatgaacacgtatagcttt
atcacaaactgtatattttaaactgttagcgacgtccttggccacgaaccggacctgttggtcgcgctctagcacgtaccgcaggttgaacgtatc
ttctccaaatttaaattctccaattttaacgcgagccattttgatacacgtgtgtcgattttgcaacaactattgtttttaacgcaaactaaacttat
tgtggtaagcaataattaaatatgggggaacatgcgccgctacaacactcgtcgttatgaacgcagacggcgccggtctcggcgcaagcggcta
aaacgtgttgcgcgttcaacgcggcaaacatcgcaaaagccaatagtacagttttgatttgcatattaacggcgatttttttaaattatcttatttaa
taaatagttatgacgcctacaactccccgcccgcgttgactcgctgcacctcgagcagttcgttgacgccttcctccgtgtggccgaacacgtcga
gcgggtggtcgatgaccagcggcgtgccgcacgcgacgcacaagtatctgtacaccgaatgatcgtcgggcgaaggcacgtcggcctccaagt
ggcaatattggcaaattcgaaaatatatacagttgggttgtttgcgcatatctatcgtggcgttgggcatgtacgtccgaacgttgatttgcatgca
agccgaaattaaatcattgcgattagtgcgattaaaacgttgtacatcctcgcttttaatcatgccgtcgattaaatcgcgcaatcgagtcaagtg
atcaaagtgtggaataatgttttctttgtattcccgagtcaagcgcagcgcgtattttaacaaactagccatcttgtaagttagtttcatttaatgca
actttatccaataatatattatgtatcgcacgtcaagaattaacaatgcgcccgttgtcgcatctcaacacgactatgatagagatcaaataaagc
gcgaattaaatagcttgcgacgcaacgtgcacgatctgtgcacgcgttccggcacgagctttgattgtaataagtttttacgaagcgatgacatg
acccccgtagtgacaacgatcacgcccaaaagaactgccgactacaaaattaccgagtatgtcggtgacgttaaaactattaagccatccaatc
gaccgttagtcgaatcaggaccgctggtgcgagaagccgcgaagtatggcgaatgcatcgtataacgtgtggagtccgctcattagagcgtcat
gtttagacaagaaagctacatatttaattgatcccgatgattttattgataaattgaccctaactccatacacggtattctacaatggcggggtttt
ggtcaaaatttccggactgcgattgtacatgctgttaacggctccgcccactattaatgaaattaaaaattccaattttaaaaaacgcagcaaga
gaaacatttgtatgaaagaatgcgtagaaggaaagaaaaatgtcgtcgacatgctgaacaacaagattaatatgcctccgtgtataaaaaaaa
tattgaacgatttgaaagaaaacaatgtaccgcgcggcggtatgta

FIG. 16D caggaagaggtttatactaaactgttacattgcaaacgtggtttcgtgtgccaagtgtgaaaaccgatgtttaatcaaggctctgacgcatttcta
caaccacgactccaagtgtgtgggtgaagtcatgcatcttttaatcaaatcccaagatgtgtataaaccaccaaactgccaaaaaatgaaaact
gtcgacaagctctgtccgtttgctggcaactgcaagggtctcaatcctatttgtaattattgaataataaaacaattataaatgctaaatttgttttt
tattaacgatacaaaccaaacgcaacaagaacatttgtagtattatctataattgaaaacgcgtagttataatcgctgaggtaatatttaaaatc
attttcaaatgattcacagttaatttgcgacaatataattttattttcacataaactagacgccttgtcgtcttcttcttcgtattccttctctttttcatt
tttctcctcataaaaattaacatagttattatcgtatccatatatgtatctatcgtatagagtaaatttttttgttgtcataaatatatatgtcttttttaa
tggggtgtatagtaccgctgcgcatagtttttctgtaatttacaacagtgctattttctggtagttcttcggagtgtgttgctttaattattaaatttat
ataatcaatgaatttgggatcgtcggttttgtacaatatgttgccggcatagtacgcagcttcttctagttcaattacaccatttttttagcagcaccg
gattaacataactttccaaaatgttgtacgaaccgttaaacaaaaacagttcacctcccttttctatactattgtctgcgagcagttgtttgttgtta
aaaataacagccattgtaatgagacgcacaaactaatatcacaaactggaaatgtctatcaatatatagttgctgatatctccccagcatgcctg
ctattgtcttcccaatcctcccccttgctgtcctgccccaccccacccccccagaatagaatgacacctactcagacaatgcgatgcaatttcctcatt
ttattaggaaaggacagtgggagtggcaccttccagggtcaaggaaggcacgggggaggggcaaacaacagatggctggcaactagaaggc
acagtcgaggcgaattcttagcactcgccgcggttgaaggacttggtcaccgggctcgacaggccctggtgggtcacctcgcaggcgtacactt
gtgcttctcgtaatcggccttggacagggtcagggtggagctcagcgagtaggtgctatccttggaatcctgctcggtcacgctctcctgggagtt
gccggactgcagggcgttatccaccttccactgcaccttggcctcgcggggtagaagttgttcagcaggcacaccacggaggcggtgccggac
ttcagctgctcgtccgacggcggggaagatgaacacggagggggcggccacggtgcgcttgatctccagcttggtgccgcccgccgaaggtcggg
gggttgctggtccactgctggcagtagtaggtggcggcatcctcggcctccacgcgggagatggtcaggctgtaggaggtgccgctgccgctgcc
ggagaagcgcaccggcacgccggaggccagattggaggtggcgtagatccaggccttcggggagctgcctggcttctgctggaaccagtgaat
gtagctcacgctggaggaggcgcggcaggtcatggtcaccttctcgcccggcgaggcgctcaggatggcggggctctgcgacagcacgatctgg
ccgcggctcatgatcacggaggcgctgatcagcaggaaggagatgatctgcacctggaaa-3′

SEQUENCE LISTING

<160> NUMBER OF SEQ ID NOS: 27

<210> SEQ ID NO 1
<211> LENGTH: 11844
<212> TYPE: DNA
<213> ORGANISM: Artificial Sequence
<220> FEATURE:
<223> OTHER INFORMATION: pChi/Cath-EGFP/RMD

<400> SEQUENCE: 1

```
ttacacgtag aattctactc gtaaagcagt ttatgagccc gtgtgcaaaa catgacatca     60

tctcgatttg aaaaacaaat gaccatcatc cactcgatcg tgcgttacaa gtagaattct    120

actcgtaaag ccagttcggt tatgagccgt gtgcaaaaca tgacatcagc ttatgactca    180

tacttgattg tgttttacgc gaagggcgaa ttccagcaca ctggcggccg ttactagacg    240

atgtctttgt gatgcgcgcg acatttttgt aggttattga taaaatgaac ggatacgttg    300

cccgacatta tcattaaatc cttggcgtag aatttgtcgg gtccattgtc cgtgtgcgct    360

agcatgcccg taacggacct cgtacttttg gcttcaaagg ttttgcgcac agacaaaatg    420

tgccacactt gcagctctgc atgtgtgcgc gttaccacaa atcccaacgg cgcagtgtac    480

ttgttgtatg caaataaatc tcgataaagg cgcggcgcgc gaatgcagct gatcacgtac    540

gctcctcgtg ttccgttcaa ggacggtgtt atcgacctca gattaatgtt tatcggccga    600

ctgttttcgt atccgctcac caaacgcgtt tttgcattaa cattgtatgt cggcggatgt    660

tctatatcta atttgaataa ataaacgata accgcgttgg ttttagaggg cataataaaa    720

gaaatattgt tatcgtgttc gccattaggg cagtataaat tgacgttcat gttggatatt    780

gtttcagttg caagttgaca ctggcggcga caagatcgtg aacaaccaag tgaccggtac    840

caccatggtg agcaagggcg aggagctgtt caccggggtg gtgcccatcc tggtcgagct    900

ggacggcgac gtaaacggcc acaagttcag cgtgtccggc gagggcgagg gcgatgccac    960

ctacggcaag ctgaccctga agttcatctg caccaccggc aagctgcccg tgccctggcc   1020

caccctcgtg accaccctga cctacggcgt gcagtgcttc agccgctacc ccgaccacat   1080

gaagcagcac gacttcttca agtccgccat gcccgaaggc tacgtccagg agcgcaccat   1140

cttcttcaag gacgacggca actacaagac ccgcgccgag gtgaagttcg agggcgacac   1200

cctggtgaac cgcatcgagc tgaagggcat cgacttcaag gaggacggca acatcctggg   1260

gcacaagctg gagtacaact acaacagcca caacgtctat atcatggccg acaagcagaa   1320

gaacggcatc aaggtgaact tcaagatccg ccacaacatc gaggacggca gcgtgcagct   1380

cgccgaccac taccagcaga acacccccat cggcgacggc cccgtgctgc tgcccgacaa   1440

ccactacctg agcacccagt ccgccctgag caaagacccc aacgagaagc gcgatcacat   1500

ggtcctgctg gagttcgtga ccgccgccgg gatcactctc ggcatggacg agctgtacaa   1560

gtaatcgaaa cgcctcgact gtgccttcta gttgccagcc atctgttgtt tgcccctccc   1620

ccgtgccttc cttgaccctg gaaggtgcca ctcccactgt cctttcctaa taaaatgagg   1680

aaattgcatc gcattgtctg agtaggtgtc attctattct ggggggtggg gtggggcagg   1740

acagcaaggg ggaggattgg gaagacaata gcaggcatgc tggggaacta gtgtggcggc   1800

gctaaacaag aaatagcccc ggtggccaag agtatgcccg ttcctcctac ttttaagcta   1860

attcgactgg cgtcgtctca acaaagtcac tagcgtaaaa aatcagggca tgtgtggcgc   1920
```

-continued

```
ctgctgggcg tttgccactc tggctagttt ggaaagtcaa tttgcaatca aacataacca   1980
gttgattaat ctgtcggagc agcaaatgat cgattgtgat tttgtcgacg ctggctgtaa   2040
cggcggcttg ttgcacacag cgttcgaagc catcattaaa atgggcggcg tacagctgga   2100
aagcgactat ccatacgaag cagacaataa caattgccgt atgaactcca ataagtttct   2160
agttcaagta aaagattgtt atagatacat taccgtgtac gaggaaaaac ttaaagattt   2220
gttacgcctt gtcggcccta ttcctatggc catagacgct gccgacattg ttaactataa   2280
acagggtatt ataaaatatt gtttcaacag cggtctaaac catgcggttc ttttagtggg   2340
ttatggtgtt gaaaacaaca ttccatattg gacctttaaa aacacttggg gcacggattg   2400
gggagaggac ggatttttca gggtacaaca aaacataaac gcctgtggta tgagaaacga   2460
acttgcgtct actgcagtca tttattaatc tcaacacact cgctatttgg aacataatca   2520
tatcgtctca gtagctcaag gtagagcgta gcgctctgga tcgtatagat cttgctaagg   2580
ttgtgagttc aagtctcgcc tgagatatta aaaaactttg taattttaaa aattttattt   2640
tataatatac aattaaaaac tatacaattt tttattatta cattaataat gatacaattt   2700
ttattattac atttaatatt gtctattacg gtttctaatc atacagtaca aaaataaaat   2760
cacaattaat ataattacaa agttaactac atgaccaaac atgaacgaag tcaatttagc   2820
ggccaattcg ccttcagcca tggaagtgat atcgctcaga ctggtgccga cgccgccaaa   2880
cttggtgttc tccatggtgg ttatgaggtt gctttttttgt tgggcaataa acgaccagcc   2940
gctggcatct ttccaactgt cgtgataggt cgtgttgccg atggtcggga tccaaaactc   3000
gacgtcgtcg tcaattgcta gttccttgta gttgctaaaa tctatgcatt gcgacgagtc   3060
cgtgttggcc acccaacgcc cttctttgta gatgctgttg ttgtagcaat tactggtgtg   3120
tgccggcgga ttggtgcacg gcatcagcaa aaacgtgtcg tccgacaaaa atgttgaaga   3180
aacagagttg ttcatgagat tgccaatcaa acgctcgtcc accttggcca cggagactat   3240
caggtcgtgc agcatattgt ttagcttgtt gatgtgcgca tgcatcagct caatgttcat   3300
tttcagcaaa tcgttttcgt acatcagctc ctcttgaata tgcatcaggt cgcctttggt   3360
ggcagtgtct ccctctgtgt acttggctct aacgttgtgg cgccaagtgg gcggccgctt   3420
cttgactcgg tgctcgactt tgcgtttaat gcatctgtta aacttgcagt tccacgtgtt   3480
tttagaaaga tcatatatat cattgtcaat caaacagtgt tcgcgtgtca ccgactcggg   3540
gttatttttg tcatctttaa tgagcagaca cgcagctttt atttggcgcg tggtgaacgt   3600
agacttttgt ttgagaatca tactcacgcc gtctcgatga agcacagtgt ccacggtcac   3660
gttgatgggg ttgccctcag cgtccaaaat gtatacctgg cactcgtccg tgtcgtcctg   3720
gcactcgagc ctgctgtaca ttttcgaagt ggaaatgccg catcgccacg atttgttgca   3780
cgtgtggtgc gcaaagtgat tgttattctg ccgcttcacc aactctttgc ctttgaccca   3840
ctggccgcgg ccctcgttgt cgcgaaaaca gtcgtcgctg tcactgcccc aacggtcgat   3900
cagctcttcg cccacctcgc actgctgcct gatgctccac ataagcaaat cctctttgcc   3960
cacattcagc gttttcatgg tttcttcgac gcgtgtgttg ggatccagcg agccgccgtt   4020
gtacgcatac gcctggtagt acccccttgta gccgataatc acgttttcgt tgtagtccgt   4080
ctccacgatg gtgatttcca cgtccttttg cagcgtttcc ttgggcgggg taatgtccaa   4140
gtttttaatc ttgtacggac ccgtcttcat ttgcgcgttg cagtgctccg ccgcaaaggc   4200
agaatgcgcc gccgccgcca aaagcacata taaaacaata gcgcttacca tcttgctaat   4260
cccgcggcca tggcggccgg gagcatgcga cgtcgggccc aattcgccct atagtgagtc   4320
```

-continued

```
gtattacaat tcactggccg tcgttttaca acgtcgtgac tgggaaaacc ctggcgttac   4380
ccaacttaat cgccttgcag cacatccccc tttcgccagc tggcgtaata gcgaagaggc   4440
ccgcaccgat cgcccttccc aacagttgcg cagcctgaat ggcgaatgga cgcgccctgt   4500
agcggcgcat taagcgcggc gggtgtggtg gttacgcgca gcgtgaccgc tacacttgcc   4560
agcgccctag cgcccgctcc tttcgctttc ttcccttcct ttctcgccac gttcgccggc   4620
tttccccgtc aagctctaaa tcgggggctc cctttagggt tccgatttag tgctttacgg   4680
cacctcgacc ccaaaaaact tgattagggt gatggttcac gtagtgggcc atcgccctga   4740
tagacggttt ttcgcccttt gacgttggag tccacgttct ttaatagtgg actcttgttc   4800
caaactggaa caacactcaa ccctatctcg gtctattctt ttgatttata agggattttg   4860
ccgatttcgg cctattggtt aaaaaatgag ctgatttaac aaaaatttaa cgcgaatttt   4920
aacaaaatat taacgcttac aatttcctga tgcggtattt tctccttacg catctgtgcg   4980
gtatttcaca ccgcatcagg tggcactttt cggggaaatg tgcgcggaac ccctatttgt   5040
ttatttttct aaatacattc aaatatgtat ccgctcatga gacaataacc ctgataaatg   5100
cttcaataat attgaaaaag gaagagtatg agtattcaac atttccgtgt cgcccttatt   5160
cccttttttg cggcattttg ccttcctgtt tttgctcacc cagaaacgct ggtgaaagta   5220
aaagatgctg aagatcagtt gggtgcacga gtgggttaca tcgaactgga tctcaacagc   5280
ggtaagatcc ttgagagttt tcgccccgaa gaacgttttc caatgatgag cacttttaaa   5340
gttctgctat gtggcgcggt attatcccgt attgacgccg ggcaagagca actcggtcgc   5400
cgcatacact attctcagaa tgacttggtt gagtactcac cagtcacaga aaagcatctt   5460
acggatggca tgacagtaag agaattatgc agtgctgcca taaccatgag tgataacact   5520
gcggccaact tacttctgac aacgatcgga ggaccgaagg agctaaccgc ttttttgcac   5580
aacatggggg atcatgtaac tcgccttgat cgttgggaac cggagctgaa tgaagccata   5640
ccaaacgacg agcgtgacac cacgatgcct gtagcaatgg caacaacgtt gcgcaaacta   5700
ttaactggcg aactacttac tctagcttcc cggcaacaat taatagactg gatggaggcg   5760
gataaagttg caggaccact tctgcgctcg gcccttccgg ctggctggtt tattgctgat   5820
aaatctggag ccggtgagcg tgggtctcgc ggtatcattg cagcactggg gccagatggt   5880
aagccctccc gtatcgtagt tatctacacg acggggagtc aggcaactat ggatgaacga   5940
aatagacaga tcgctgagat aggtgcctca ctgattaagc attggtaact gtcagaccaa   6000
gtttactcat atatacttta gattgattta aaacttcatt tttaatttaa aaggatctag   6060
gtgaagatcc tttttgataa tctcatgacc aaaatccctt aacgtgagtt ttcgttccac   6120
tgagcgtcag accccgtaga aaagatcaaa ggatcttctt gagatccttt ttttctgcgc   6180
gtaatctgct gcttgcaaac aaaaaaacca ccgctaccag cggtggtttg tttgccggat   6240
caagagctac caactctttt tccgaaggta actggcttca gcagagcgca gataccaaat   6300
actgttcttc tagtgtagcc gtagttaggc caccacttca agaactctgt agcaccgcct   6360
acatacctcg ctctgctaat cctgttacca gtggctgctg ccagtggcga taagtcgtgt   6420
cttaccgggt tggactcaag acgatagtta ccggataagg cgcagcggtc gggctgaacg   6480
gggggttcgt gcacacagcc cagcttggag cgaacgacct acaccgaact gagataccta   6540
cagcgtgagc tatgagaaag cgccacgctt cccgaaggga gaaaggcgga caggtatccg   6600
gtaagcggca gggtcggaac aggagagcgc acgagggagc ttccaggggg aaacgcctgg   6660
```

-continued

```
tatctttata gtcctgtcgg gtttcgccac ctctgacttg agcgtcgatt tttgtgatgc   6720
tcgtcagggg ggcggagcct atggaaaaac gccagcaacg cggccttttt acggttcctg   6780
gccttttgct ggccttttgc tcacatgttc tttcctgcgt tatcccctga ttctgtggat   6840
aaccgtatta ccgcctttga gtgagctgat accgctcgcc gcagccgaac gaccgagcgc   6900
agcgagtcag tgagcgagga agcggaagag cgcccaatac gcaaaccgcc tctccccgcg   6960
cgttggccga ttcattaatg cagctggcac gacaggtttc ccgactggaa agcgggcagt   7020
gagcgcaacg caattaatgt gagttagctc actcattagg caccccaggc tttacacttt   7080
atgcttccgg ctcgtatgtt gtgtggaatt gtgagcggat aacaatttca cacaggaaac   7140
agctatgacc atgattacgc caagctattt aggtgacact atagaatact caagctatgc   7200
atccaacgcg ttgggagctc tcccatatgg tcgacctgca ggcggccgca ctagtgatta   7260
tgggtttgtt tgcgtgttgc acaaaataca caaggctgtc gaccgacaca aaaatgaagt   7320
ttccctatgt tgcgttgtcg tacatcaacg tgacgctgtg cacctacacc gccatgttgg   7380
tgggatacat ggtaacattc aatgactcca gcgaattgaa atatttacaa tactggttgc   7440
tgttgtcgtt tttgatgtcc gtggtgctaa acgctccgac tctgtggacg atgctcaaaa   7500
ccacagaagc ccatgaagta atttacgaaa tgaagctgtt ccacgccatg tactttagta   7560
acgtgctgtt gaattatgtg gtgtttttgg acaatcaaat gggtacaaat tttgtttttg   7620
ttaacaattt aattcactgt tgtgtacttt ttatgatatt tgttgaattg cttatcctgt   7680
tgggccacac aatgggcacg tacacggatt atcaatatgt caaatcgtgt tatatggtta   7740
tattgtttgt ttcagttatg agtgttacta ttgttatggg tttagagtgt ttgaaaacga   7800
aactaattga taacagtttg atgtttaacg cgtttgtgtg cgctttgtac attgtgattg   7860
caataatgtg gtctttaaaa aataatttga ctagttatta cgtttcaaat ttacaaagta   7920
ttcaagttgt tccgttttca tacaacgatc cgccgccacc gttctctaac attgtaatgg   7980
atgacataaa aaataaaaaa taatttataa aaatgttttt tattctttca caattctgta   8040
aattctaaac aaaaaatata aatacaaact tattatgttg tcgtctaaat aaacatcaat   8100
ttgtaaatct ggacacctat tcatatcatt gatattacag tctactatac aacaattaaa   8160
actaaccaaa ttatctttac aacaattaaa gcaattaaaa caatttaaat aatcttcatt   8220
gtcgtcgtat aagtttattt gcactgtaga cggtgttaca cagcgatcca ttcgacgttc   8280
gtgttcgatc aactttctcg ccaacttgta ccataaaaat tgtttggaca aaaagttttc   8340
caacaatggt aacggccaat tcaacgtgac gatgcgcacg tcctcgggta tgcatttgtt   8400
aaaaaacaca cagctcgctt taccaaacga aagcaaaggt actaaatatg gcgccattgg   8460
ctgatttgtt attccaagat aattacaaat aaactgatcc gtcgtggggt gataactggc   8520
aggtgtcagc tttaaataat cttcaacgtt gttgtcgcgc aaaagtctgc attttacacg   8580
cgttgttaat cccacgactt ttgcatgtaa aatcggatcc aaatactgca gaatcgtgtc   8640
tataatttct aatggtaaac gtatgcgttt tgctcgtggg cgctttgtaa cgctcgacat   8700
cctaataaca actaacacaa aactaaaatg atactcaata tattgctttt acagttcatc   8760
tttaggttta aactgtgcgt ttatcgcgtt gagcaagtcg ccgttatcgg catcaatctc   8820
ccaagcaaac aggccgccca atttatttcg gtcgacatat ttaacttttc ctaacacaga   8880
gtcgacgctg tcaaacgaaa tcaaatcacc tttactttta tcgaaaacgt acgacgcttg   8940
agcggcgctg tcaaacgtgt acacataatt gttgagatct ttttgaattt gacgataatc   9000
tacaacaccg tcctcccacg tgcccgaccc cggcccgttg ccagtgccgg aaaaatagtt   9060
```

-continued

```
gtcattcgta taatttgtta cgccggtcca gccgcggccg tacatggcga cgcccacaat   9120
tattttgttg ggatcgacgc cttgtttcag taacgcatcg acagcgtagt gtgtagtgta   9180
tagctcttcc gagttccaac ttggcgcgta gactgttgtt tggtagccca aatccgtgtt   9240
tgaccaagcc cctttaaaat cgtaactcat gagaaatatt ttgcctaatg acttttgcgc   9300
ttcggcgtag tttaccacgg caatcttgtc gtaacccgcg cttatagcgc ttgttaattc   9360
gtaaaccctg ccggtttgcg cttcgaggtc gtctagcatt gcgcgcagct cctccaacaa   9420
caaaatgtat gttttggcgt caccgtccgc atcgcccaac gacgggttag cccctttgcc   9480
gcccggaaac tcccaatcga tgtctacacc gtcaaagaat ttccacactt gcagaaattc   9540
cttaaccgaa tctacaaaaa cgtttctttt ttcaacatcg tgcataaaat aaaatgggtc   9600
tgatagagtc cagcctccta ttgaaggaag aatttttaaa tgggggtttg ctaattttgc   9660
cgccatcaac tgtccaaaat tgcctttata cggctcgttc caagcggaca caccttttg    9720
gggtttttgt acggcggccc acggatcgtg aatggcaact ttgaaatctt cgcgtccctt   9780
gcacgatctt tgcaaagatt caaagctgat cctccccagc atgcctgcta ttgtcttccc   9840
aatcctcccc cttgctgtcc tgccccaccc cacccccag aatagaatga cacctactca    9900
gacaatgcga tgcaatttcc tcattttatt aggaaaggac agtgggagtg gcaccttcca   9960
gggtcaagga aggcacgggg gaggggcaaa caacagatgg ctggcaacta gaaggcacag  10020
tcgaggcggg cccttactcc tctctaacac gagattccca atcggacagg atggccctca  10080
gtgattgttt gatagtgatt tcgggtttcc atccagtagt atcatggagg cgggcatgag  10140
agcctctaac acgacgttgc tcggcacgcc tcattctggc gggatcttga acgatttcca  10200
gctcaacttg agcaatatcg gccaacagct cgatgagttc acgaattttt tgttcttgtc  10260
cagagcacac gttgtaaacg gctccggcct ctccgtggga caacagtctc aggtaagcag  10320
acagcacgtc ttgaacgtcc aagaagtccc tcgacacgtc gatgtcacca acttcgaggc  10380
ggtttgcctg gaggccttgt ttcatcctag caatttggcg agcagcagaa gcgatcacga  10440
acgaatcctt ttggccagga ccaatgtggt tgaaaggacg ggcaaccaaa acacgccagc  10500
cctcagtgat tccccattgg agacacagag attcagcagc caatttggac acagcgtaag  10560
ggttacgggg atgagggatg agttcctcgt gaataggcaa ggcagcctcg gccacttgac  10620
cgtacacatc accggaggag atgtacagga aggttccgga gaatcctcta gccttcagag  10680
cttggagcaa gttcagtgtt cccagcaggt tgatttggag agtacgagca ggatcacgga  10740
atgcctcggg tacgtatgtt tgaccagcga ggtgaataac agcatccggc aattcgggcc  10800
acaaatcgcc caaagagtcg ggttccaaca agtcgtagcg gtgaggaaca gggagcaaag  10860
cccaaggtgt gtgagcagcc gccaagtatg cctggaggtg tttaccgacg aagccagaca  10920
gtcccgttac gaacaagcgt tgagtcatgg ttcgcgaggt cacttggttg ttcacgatct  10980
tgtcgccgcc agtgtcaact tgcaactgaa acaatatcca acatgaacgt caatttatac  11040
tgccctaatg gcgaacacga taacaatatt tcttttatta tgccctctaa aaccaacgcg  11100
gttatcgttt atttattcaa attagatata gaacatccgc cgacatacaa tgttaatgca  11160
aaaacgcgtt tggtgagcgg atacgaaaac agtcggccga taaacattaa tctgaggtcg  11220
ataacaccgt ccttgaacgg aacacgagga gcgtacgtga tcagctgcat tcgcgcgccg  11280
cgcctttatc gagatttatt tgcatacaac aagtacactg cgccgttggg atttgtggta  11340
acgcgcacac atgcagagct gcaagtgtgg cacattttgt ctgtgcgcaa aacctttgaa  11400
```

-continued

```
gccaaaagta cgaggtccgt tacgggcatg ctagcgcaca cggacaatgg acccgacaaa  11460

ttctacgcca aggatttaat gataatgtcg ggcaacgtat ccgttcattt tatcaataac  11520

ctacaaaaat gtcgcgcgca tcacaaagac atcgacgcgc gtagaattct acccgtaaag  11580

cgagtttagt tatgagccat gtgcaaaaca tgacatcagc ttttattttt ataacaaatg  11640

acatcatttc ttgattgtgt tttacacgta gaattctact cgtaaagccg agagttcagt  11700

tttgaaaaac aaatgacatc atctttttga ttgtgcttta cgagtagaat tctacccgta  11760

aatcaagttc ggttttgaaa aacaaatgag tcatattgta tgatatcata ttgcaaaaca  11820

aatgactcat caatcgatcg tgcg                                        11844
```

<210> SEQ ID NO 2
<211> LENGTH: 12420
<212> TYPE: DNA
<213> ORGANISM: Artificial Sequence
<220> FEATURE:
<223> OTHER INFORMATION: pVL1393-polh-antiCD20-IgG

<400> SEQUENCE: 2

```
agcgcccgat ggtgggacgg tatgaataat ccggaatatt tataggtttt tttattacaa     60

aactgttacg aaaacagtaa aatacttatt tatttgcgag atggttatca ttttaattat    120

ctccatgatg ctagctgagt ttcaaattgg taattggacc cttcattaag atttcacaca    180

gatcagccga ctgcgaatag aaactcacct aggcactagt ctcgagatca tggagataat    240

taaaatgata accatctcgc aaataaataa gtattttact gttttcgtaa cagttttgta    300

ataaaaaaac ctataaatat tccggattat tcataccgtc ccaccatcgg gcgctgttta    360

aacaccatgg gctggtccct gatcctgctg ttcctggtgg ccgtggccac ccgcgtgctg    420

agccaggtgc agctgcagca gcccggcgcc gagctggtga agcccggcgc ctccgtgaag    480

atgagctgca aggccagcgg ctacaccttc acctcctaca atatgcactg ggtgaagcag    540

accccgggcc gcggcctgga gtggatcggc gccatctacc cgggcaacgg cgatacctcc    600

tacaaccaga agttcaaggg caaggccacc ctgaccgccg ataagagctc cagcaccgcc    660

tacatgcagc tgtcctcgct gaccagcgag gacagcgccg tgtactactg cgcccgcagc    720

acctactacg gcggcgattg gtacttcaac gtgtggggcg ccggcaccac cgtgaccgtg    780

agcgccgcca gcaccaaggg cccctccgtg ttcccgctgg ccccgtcgag caagagcacc    840

agcggcggca ccgccgccct gggctgcctg gtgaaggatt acttcccgga gcccgtgacc    900

gtgtcgtgga acagcggcgc cctgaccagc ggcgtgcaca ccttcccagc cgtgctgcag    960

agctcgggcc tgtactcgct gagcagcgtg gtgaccgtgc cgtcgagctc gctgggcacc   1020

cagacctaca tctgcaacgt gaaccacaag ccatccaata ccaaggtgga taagaaggcc   1080

gagcccaaga gctgcgacaa gacccacacc tgccccccct gcccggcccc agagctgctg   1140

ggcggcccat ccgtgttcct gttccccccg aagccgaagg acaccctgat gatcagccgc   1200

acccccgagg tgacctgcgt ggtggtggat gtgagccacg aggaccccga ggtgaagttc   1260

aactggtacg tggatggcgt ggaggtgcac aacgccaaga ccaagccccg cgaggagcag   1320

tacaacagca cctaccgcgt ggtgtcggtg ctgaccgtgc tgcaccagga ttggctgaac   1380

ggcaaggagt acaagtgcaa ggtgtccaac aaggccctgc ccgcccccgat cgagaagacc   1440

atctccaagg ccaagggcca gccacgcgag ccgcaggtgt acaccctgcc accctcccgc   1500

gatgagctga ccaagaacca ggtgagcctg acctgcctgg tgaagggctt ctacccctcg   1560

gatatcgccg tggagtggga gagcaacggc cagccggaga acaactacaa gaccaccccca   1620
```

```
cccgtgctgg acagcgacgg cagcttcttc ctgtacagca agctgaccgt ggacaagtcg   1680
cgctggcagc agggcaacgt gttctcctgc agcgtgatgc acgaggccct gcacaaccac   1740
tacacccaga agagcctgag cctgagcccc ggcaagtaac ctgcagatct gcctcgactg   1800
tgccttctag ttgccagcca tctgttgttt gcccctcccc cgtgccttcc ttgaccctgg   1860
aaggtgccac tcccactgtc ctttcctaat aaaatgagga aattgcatcg cattgtctga   1920
gtaggtgtca ttctattctg gggggtgggg tggggcagga cagcaagggg gaggattggg   1980
aagacaatag caggcatgct ggggaggatc tgatcctttc ctgggacccg gcaagaacca   2040
aaaactcact ctcttcaagg aaatccgtaa tgttaaaccc gacacgatga agcttgtcgt   2100
tggatggaaa ggaaaagagt tctacaggga aacttggacc cgcttcatgg aagacagctt   2160
ccccattgtt aacgaccaag aagtgatgga tgttttcctt gttgtcaaca tgcgtcccac   2220
tagacccaac cgttgttaca aattcctggc ccaacacgct ctgcgttgcg accccgacta   2280
tgtacctcat gacgtgatta ggatcgtcga gccttcatgg gtgggcagca acaacgagta   2340
ccgcatcagc ctggctaaga agggcggcgg ctgcccaata atgaaccttc actctgagta   2400
caccaactcg ttcgaacagt tcatcgatcg tgtcatctgg gagaacttct acaagcccat   2460
cgtttacatc ggtaccgact ctgctgaaga ggaggaaatt ctccttgaag tttccctggt   2520
gttcaaagta aaggagtttg caccagacgc acctctgttc actggtccgg cgtattaaaa   2580
cacgatacat tgttattagt acatttatta agcgctagat tctgtgcgtt gttgatttac   2640
agacaattgt tgtacgtatt ttaataattc attaaattta taatctttag ggtggtatgt   2700
tagagcgaaa atcaaatgat tttcagcgtc tttatatctg aatttaaata ttaaatcctc   2760
aatagatttg taaaataggt ttcgattagt ttcaaacaag ggttgttttt ccgaaccgat   2820
ggctggacta tctaatggat tttcgctcaa cgccacaaaa cttgccaaat cttgtagcag   2880
caatctagct ttgtcgatat tcgtttgtgt tttgttttgt aataaaggtt cgacgtcgtt   2940
caaaatatta tgcgcttttg tatttctttc atcactgtcg ttagtgtaca attgactcga   3000
cgtaaacacg ttaaataaag cttggacata tttaacatcg ggcgtgttag ctttattagg   3060
ccgattatcg tcgtcgtccc aaccctcgtc gttagaagtt gcttccgaag acgattttgc   3120
catagccaca cgacgcctat taattgtgtc ggctaacacg tccgcgatca aatttgtagt   3180
tgagcttttt ggaattattt ctgattgcgg gcgtttttgg gcgggtttca atctaactgt   3240
gcccgatttt aattcagaca acacgttaga aagcgatggt gcaggcggtg gtaacatttc   3300
agacggcaaa tctactaatg gcggcggtgg tggagctgat gataaatcta ccatcggtgg   3360
aggcgcaggc ggggctggcg gcggaggcgg aggcggaggt ggtggcggtg atgcagacgg   3420
cggtttaggc tcaaatgtct ctttaggcaa cacagtcggc acctcaacta ttgtactggt   3480
ttcgggcgcc gtttttggtt tgaccggtct gagacgagtg cgattttttt cgtttctaat   3540
agcttccaac aattgttgtc tgtcgtctaa aggtgcagcg ggttgaggtt ccgtcggcat   3600
tggtggagcg ggcggcaatt cagacatcga tggtggtggt ggtggtggag gcgctggaat   3660
gttaggcacg ggagaaggtg gtggcggcgg tgccgccggt ataatttgtt ctggtttagt   3720
ttgttcgcgc acgattgtgg gcaccggcgc aggcgccgct ggctgcacaa cggaaggtcg   3780
tctgcttcga ggcagcgctt ggggtggtgg caattcaata ttataattgg aatacaaatc   3840
gtaaaaatct gctataagca ttgtaatttc gctatcgttt accgtgccga tatttaacaa   3900
ccgctcaatg taagcaattg tattgtaaag agattgtctc aagctccgca cgccgataac   3960
```

-continued

```
aagcctttc atttttacta cagcattgta gtggcgagac acttcgctgt cgtcgacgta 4020
catgtatgct ttgttgtcaa aaacgtcgtt ggcaagcttt aaaatattta aaagaacatc 4080
tctgttcagc accactgtgt tgtcgtaaat gttgtttttg ataatttgcg cttccgcagt 4140
atcgacacgt tcaaaaaatt gatgcgcatc aattttgttg ttcctattat tgaataaata 4200
agattgtaca gattcatatc tacgattcgt catggccacc acaaatgcta cgctgcaaac 4260
gctggtacaa ttttacgaaa actgcaaaaa cgtcaaaact cggtataaaa taatcaacgg 4320
gcgctttggc aaaatatcta ttttatcgca caagcccact agcaaattgt atttgcagaa 4380
aacaatttcg gcgcacaatt ttaacgctga cgaaataaaa gttcaccagt taatgagcga 4440
ccacccaaat tttataaaaa tctattttaa tcacggttcc atcaacaacc aagtgatcgt 4500
gatggactac attgactgtc ccgatttatt tgaaacacta caaattaaag gcgagctttc 4560
gtaccaactt gttagcaata ttattagaca gctgtgtgaa gcgctcaacg atttgcacaa 4620
gcacaatttc atacacaacg acataaaact cgaaaatgtc ttatatttcg aagcacttga 4680
tcgcgtgtat gtttgcgatt acggattgtg caaacacgaa aactcactta gcgtgcacga 4740
cggcacgttg gagtatttta gtccggaaaa aattcgacac acaactatgc acgtttcgtt 4800
tgactggtac gcggcgtgtt aacatacaag ttgctaaccg gcggttcgta atcatggtca 4860
tagctgtttc ctgtgtgaaa ttgttatccg ctcacaattc cacacaacat acgagccgga 4920
agcataaagt gtaaagcctg gggtgcctaa tgagtgagct aactcacatt aattgcgttg 4980
cgctcactgc ccgctttcca gtcgggaaac ctgtcgtgcc agctgcatta atgaatcggc 5040
caacgcgcgg ggagaggcgg tttgcgtatt gggcgctctt ccgcttcctc gctcactgac 5100
tcgctgcgct cggtcgttcg gctgcggcga gcggtatcag ctcactcaaa ggcggtaata 5160
cggttatcca cagaatcagg ggataacgca ggaaagaaca tgtgagcaaa aggccagcaa 5220
aaggccagga accgtaaaaa ggccgcgttg ctggcgtttt tccataggct ccgcccccct 5280
gacgagcatc acaaaaatcg acgctcaagt cagaggtggc gaaacccgac aggactataa 5340
agataccagg cgtttccccc tggaagctcc ctcgtgcgct ctcctgttcc gaccctgccg 5400
cttaccggat acctgtccgc ctttctccct tcgggaagcg tggcgctttc tcatagctca 5460
cgctgtaggt atctcagttc ggtgtaggtc gttcgctcca agctgggctg tgtgcacgaa 5520
ccccccgttc agcccgaccg ctgcgcctta tccggtaact atcgtcttga gtccaacccg 5580
gtaagacacg acttatcgcc actggcagca gccactggta acaggattag cagagcgagg 5640
tatgtaggcg gtgctacaga gttcttgaag tggtggccta actacggcta cactagaagg 5700
acagtatttg gtatctgcgc tctgctgaag ccagttacct tcggaaaaag agttggtagc 5760
tcttgatccg gcaaacaaac caccgctggt agcggtggtt tttttgtttg caagcagcag 5820
attacgcgca gaaaaaaagg atctcaagaa gatcctttga tcttttctac ggggtctgac 5880
gctcagtgga acgaaaactc acgttaaggg attttggtca tgagattatc aaaaaggatc 5940
ttcacctaga tccttttaaa ttaaaaatga agttttaaat caatctaaag tatatatgag 6000
taaacttggt ctgacagtta ccaatgctta atcagtgagg cacctatctc agcgatctgt 6060
ctatttcgtt catccatagt tgcctgactc cccgtcgtgt agataactac gatacgggag 6120
ggcttaccat ctggccccag tgctgcaatg ataccgcgag acccacgctc accggctcca 6180
gatttatcag caataaacca gccagccgga agggccgagc gcagaagtgg tcctgcaact 6240
ttatccgcct ccatccagtc tattaattgt tgccgggaag ctagagtaag tagttcgcca 6300
gttaatagtt tgcgcaacgt tgttgccatt gctacaggca tcgtggtgtc acgctcgtcg 6360
```

tttggtatgg cttcattcag ctccggttcc caacgatcaa ggcgagttac atgatccccc 6420
atgttgtgca aaaaagcggt tagctccttc ggtcctccga tcgttgtcag aagtaagttg 6480
gccgcagtgt tatcactcat ggttatggca gcactgcata attctcttac tgtcatgcca 6540
tccgtaagat gcttttctgt gactggtgag tactcaacca agtcattctg agaatagtgt 6600
atgcggcgac cgagttgctc ttgcccggcg tcaatacggg ataataccgc gccacatagc 6660
agaactttaa aagtgctcat cattggaaaa cgttcttcgg ggcgaaaact ctcaaggatc 6720
ttaccgctgt tgagatccag ttcgatgtaa cccactcgtg cacccaactg atcttcagca 6780
tcttttactt tcaccagcgt ttctgggtga gcaaaaacag gaaggcaaaa tgccgcaaaa 6840
aagggaataa gggcgacacg gaaatgttga atactcatac tcttcctttt tcaatattat 6900
tgaagcattt atcagggtta ttgtctcatg agcggataca tatttgaatg tatttagaaa 6960
aataaacaaa taggggttcc gcgcacattt ccccgaaaag tgccacctga cgtctaagaa 7020
accattatta tcatgacatt aacctataaa aataggcgta tcacgaggcc ctttcgtctc 7080
gcgcgtttcg gtgatgacgg tgaaaacctc tgacacatgc agctcccgga gacggtcaca 7140
gcttgtctgt aagcggatgc cgggagcaga caagcccgtc agggcgcgtc agcgggtgtt 7200
ggcgggtgtc ggggctggct taactatgcg gcatcagagc agattgtact gagagtgcac 7260
catatgcggt gtgaaatacc gcacagatgc gtaaggagaa aataccgcat caggcgccat 7320
tcgccattca ggctgcgcaa ctgttgggaa gggcgatcgg tgcgggcctc ttcgctatta 7380
cgccagctgg cgaaaggggg atgtgctgca aggcgattaa gttgggtaac gccagggttt 7440
tcccagtcac gacgttgtaa aacgacggcc agtgccaagc tttactcgta aagcgagttg 7500
aaggatcata tttagttgcg tttatgagat aagattgaaa gcacgtgtaa aatgtttccc 7560
gcgcgttggc acaactattt acaatgcggc caagttataa aagattctaa tctgatatgt 7620
tttaaaacac ctttgcggcc cgagttgttt gcgtacgtga ctagcgaaga agatgtgtgg 7680
accgcagaac agatagtaaa acaaaaccct agtattggag caataatcga tttaaccaac 7740
acgtctaaat attatgatgg tgtgcatttt ttgcgggcgg gcctgttata caaaaaaatt 7800
caagtacctg gccagacttt gccgcctgaa agcatagttc aagaatttat tgacacggta 7860
aaagaattta cagaaaagtg tcccggcatg ttggtgggcg tgcactgcac acacggtatt 7920
aatcgcaccg gttacatggt gtgcagatat ttaatgcaca ccctgggtat tgcgccgcag 7980
gaagccatag atagattcga aaaagccaga ggtcacaaaa ttgaaagaca aaattacgtt 8040
caagatttat taatttaatt aatattattt gcattcttta acaaatactt tatcctattt 8100
tcaaattgtt gcgcttcttc cagcgaacca aaactatgct tcgcttgctc cgtttagctt 8160
gtagccgatc agtggcgttg ttccaatcga cggtaggatt aggccggata ttctccacca 8220
caatgttggc aacgttgatg ttacgtttat gcttttggtt ttccacgtac gtcttttggc 8280
cggtaatagc cgtaaacgta gtgccgtcgc gcgtcacgca caacaccgga tgtttgcgct 8340
tgtccgcggg gtattgaacc gcgcgatccg acaaatccac cactttggca actaaatcgg 8400
tgacctgcgc gtctttttc tgcattattt cgtctttctt ttgcatggtt tcctggaagc 8460
cggtgtacat gcggtttaga tcagtcatga cgcgcgtgac ctgcaaatct ttggcctcga 8520
tctgcttgtc cttgatggca acgatgcgtt caataaactc ttgtttttta acaagttcct 8580
cggttttttg cgccaccacc gcttgcagcg cgtttgtgtg ctcggtgaat gtcgcaatca 8640
gcttagtcac caactgtttg ctctcctcct cccgttgttt gatcgcggga tcgtacttgc 8700

-continued

```
cggtgcagag cacttgagga attacttctt ctaaaagcca ttcttgtaat tctatggcgt   8760
aaggcaattt ggacttcata atcagctgaa tcacgccgga tttagtaatg agcactgtat   8820
gcggctgcaa atacagcggg tcgccccttt tcacgacgct gttagaggta gggcccccat   8880
tttggatggt ctgctcaaat aacgatttgt atttattgtc tacatgaaca cgtatagctt   8940
tatcacaaac tgtatatttt aaactgttag cgacgtcctt ggccacgaac cggacctgtt   9000
ggtcgcgctc tagcacgtac cgcaggttga acgtatcttc tccaaattta aattctccaa   9060
ttttaacgcg agccattttg atacacgtgt gtcgattttg caacaactat tgttttttaa   9120
cgcaaactaa acttattgtg gtaagcaata attaaatatg ggggaacatg cgccgctaca   9180
acactcgtcg ttatgaacgc agacggcgcc ggtctcggcg caagcggcta aaacgtgttg   9240
cgcgttcaac gcggcaaaca tcgcaaaagc caatagtaca gttttgattt gcatattaac   9300
ggcgattttt taaattatct tatttaataa atagttatga cgcctacaac tccccgcccg   9360
cgttgactcg ctgcacctcg agcagttcgt tgacgccttc ctccgtgtgg ccgaacacgt   9420
cgagcgggtg gtcgatgacc agcggcgtgc cgcacgcgac gcacaagtat ctgtacaccg   9480
aatgatcgtc gggcgaaggc acgtcggcct ccaagtggca atattggcaa attcgaaaat   9540
atatacagtt gggttgtttg cgcatatcta tcgtggcgtt gggcatgtac gtccgaacgt   9600
tgatttgcat gcaagccgaa attaaatcat tgcgattagt gcgattaaaa cgttgtacat   9660
cctcgctttt aatcatgccg tcgattaaat cgcgcaatcg agtcaagtga tcaaagtgtg   9720
gaataatgtt ttctttgtat tcccgagtca agcgcagcgc gtattttaac aaactagcca   9780
tcttgtaagt tagtttcatt taatgcaact ttatccaata atatattatg tatcgcacgt   9840
caagaattaa caatgcgccc gttgtcgcat ctcaacacga ctatgataga gatcaaataa   9900
agcgcgaatt aaatagcttg cgacgcaacg tgcacgatct gtgcacgcgt tccggcacga   9960
gctttgattg taataagttt ttacgaagcg atgacatgac cccgtagtg acaacgatca  10020
cgcccaaaag aactgccgac tacaaaatta ccgagtatgt cggtgacgtt aaaactatta  10080
agccatccaa tcgaccgtta gtcgaatcag gaccgctggt gcgagaagcc gcgaagtatg  10140
gcgaatgcat cgtataacgt gtggagtccg ctcattagag cgtcatgttt agacaagaaa  10200
gctacatatt taattgatcc cgatgatttt attgataaat tgaccctaac tccatacacg  10260
gtattctaca atggcggggt tttggtcaaa atttccggac tgcgattgta catgctgtta  10320
acggctccgc ccactattaa tgaaattaaa aattccaatt ttaaaaaacg cagcaagaga  10380
aacatttgta tgaaagaatg cgtagaagga aagaaaaatg tcgtcgacat gctgaacaac  10440
aagattaata tgcctccgtg tataaaaaaa atattgaacg atttgaaaga aaacaatgta  10500
ccgcgcggcg gtatgtacag gaagaggttt atactaaact gttacattgc aaacgtggtt  10560
tcgtgtgcca agtgtgaaaa ccgatgttta atcaaggctc tgacgcattt ctacaaccac  10620
gactccaagt gtgtgggtga agtcatgcat cttttaatca aatcccaaga tgtgtataaa  10680
ccaccaaact gccaaaaaat gaaaactgtc gacaagctct gtccgtttgc tggcaactgc  10740
aagggtctca atcctatttg taattattga ataataaaac aattataaat gctaaatttg  10800
tttttattta acgatacaaa ccaaacgcaa caagaacatt tgtagtatta tctataattg  10860
aaaacgcgta gttataatcg ctgaggtaat atttaaaatc attttcaaat gattcacagt  10920
taatttgcga caatataatt ttattttcac ataaactaga cgccttgtcg tcttcttctt  10980
cgtattcctt ctctttttca tttttctcct cataaaaatt aacatagtta ttatcgtatc  11040
catatatgta tctatcgtat agagtaaatt ttttgttgtc ataaatatat atgtcttttt  11100
```

taatggggtg tatagtaccg ctgcgcatag tttttctgta atttacaaca gtgctatttt 11160
ctggtagttc ttcggagtgt gttgctttaa ttattaaatt tatataatca atgaatttgg 11220
gatcgtcggt tttgtacaat atgttgccgg catagtacgc agcttcttct agttcaatta 11280
caccattttt tagcagcacc ggattaacat aactttccaa aatgttgtac gaaccgttaa 11340
acaaaaacag ttcacctccc ttttctatac tattgtctgc gagcagttgt ttgttgttaa 11400
aaataacagc cattgtaatg agacgcacaa actaatatca caaactggaa atgtctatca 11460
atatatagtt gctgatatct ccccagcatg cctgctattg tcttcccaat cctcccccttt 11520 gctgtcctgc cccaccccac cccccagaat agaatgacac ctactcagac aatgcgatgc 11580
aatttcctca ttttattagg aaaggacagt gggagtggca ccttccaggg tcaaggaagg 11640
cacgggggag gggcaaacaa cagatggctg gcaactagaa ggcacagtcg aggcgaattc 11700
ttagcactcg ccgcggttga aggacttggt caccgggctc gacaggccct ggtgggtcac 11760
ctcgcaggcg tacaccttgt gcttctcgta atcggccttg gacagggtca gggtggagct 11820
cagcgagtag gtgctatcct tggaatcctg ctcggtcacg ctctcctggg agttgccgga 11880
ctgcagggcg ttatccacct tccactgcac cttggcctcg cgggggtaga agttgttcag 11940
caggcacacc acggaggcgg tgccggactt cagctgctcg tccgacggcg ggaagatgaa 12000
cacggagggg gcggccacgg tgcgcttgat ctccagcttg gtgccgccgc cgaaggtcgg 12060
ggggttgctg gtccactgct ggcagtagta ggtggcggca tcctcggcct ccacgcggga 12120
gatggtcagg ctgtaggagg tgccgctgcc gctgccggag aagcgcaccg gcacgccgga 12180
ggccagattg gaggtggcgt agatccaggg cttcggggag ctgcctggct tctgctggaa 12240
ccagtgaatg tagctcacgc tggaggaggc gcggcaggtc atggtcacct tctcgcccgg 12300
cgaggcgctc aggatggcgg ggctctgcga cagcacgatc tggccgcggc tcatgatcac 12360
ggaggcgctg atcagcagga aggagatgat ctgcacctgg aaatccatgg tggcggccgc 12420

<210> SEQ ID NO 3
<211> LENGTH: 12812
<212> TYPE: DNA
<213> ORGANISM: Artificial Sequence
<220> FEATURE:
<223> OTHER INFORMATION: pVL1393-p6.9-antiCD20-IgG

<400> SEQUENCE: 3
tccatggtgg cggccgcgtt taaattgtgt aatttatgta gctgtaattt ttaccttatt 60
aatatttttt acgctttgca ttcgacgact gaactcccaa atatatgttt aactcgtctt 120
ggtcgtttga atttttgttg ctgtgtttcc taatattttc catcacctta aatatgttat 180
tgtaatcctc aatgttgaac ttgcaattgg acacggcata gttttccata gtcgtgtaaa 240
acatggtatt ggctgcattg taatacatcc gactgagcgg gtacggatct atgtgtttga 300
gcagcctgtt caaaaactct gcatcgtcgc aaaacggaat ttgctagctg agtttcaaat 360
tggtaattgg acccttcatt aagatttcac acagatcagc cgactgcgaa tagaaactca 420
cctaggcact agtctcgaga aattccgttt tgcgacgatg cagagttttt gaacaggctg 480
ctcaaacaca tagatccgta cccgctcagt cggatgtatt acaatgcagc caataccatg 540
ttttacacga ctatggaaaa ctatgccgtg tccaattgca agttcaacat tgaggattac 600
aataacatat ttaaggtgat ggaaaatatt aggaaacaca gcaacaaaaa ttcaaacgac 660
caagacgagt taaacatata tttgggagtt cagtcgtcga atgcaaagcg taaaaaatat 720

-continued

```
taataaggta aaaattacag ctacataaat tacacaattt aaacgtttaa acaccatggg    780
ctggtccctg atcctgctgt tcctggtggc cgtggccacc cgcgtgctga gccaggtgca    840
gctgcagcag cccggcgccg agctggtgaa gcccggcgcc tccgtgaaga tgagctgcaa    900
ggccagcggc tacaccttca cctcctacaa tatgcactgg gtgaagcaga ccccgggccg    960
cggcctggag tggatcggcg ccatctaccc gggcaacggc gatacctcct acaaccagaa   1020
gttcaagggc aaggccaccc tgaccgccga taagagctcc agcaccgcct acatgcagct   1080
gtcctcgctg accagcgagg acagcgccgt gtactactgc gcccgcagca cctactacgg   1140
cggcgattgg tacttcaacg tgtggggcgc cggcaccacc gtgaccgtga gcgccgccag   1200
caccaagggc ccctccgtgt tcccgctggc cccgtcgagc aagagcacca gcggcggcac   1260
cgccgccctg ggctgcctgg tgaaggatta cttcccggag cccgtgaccg tgtcgtggaa   1320
cagcggcgcc ctgaccagcg gcgtgcacac cttcccagcc gtgctgcaga gctcgggcct   1380
gtactcgctg agcagcgtgg tgaccgtgcc gtcgagctcg ctgggcaccc agacctacat   1440
ctgcaacgtg aaccacaagc catccaatac caaggtggat aagaaggccg agcccaagag   1500
ctgcgacaag acccacacct gccccccctg cccggcccca gagctgctgg gcggcccatc   1560
cgtgttcctg ttcccccgga agccgaagga caccctgatg atcagccgca cccccgaggt   1620
gacctgcgtg gtggtggatg tgagccacga ggaccccgag gtgaagttca actggtacgt   1680
ggatggcgtg gaggtgcaca acgccaagac caagccccgc gaggagcagt acaacagcac   1740
ctaccgcgtg gtgtcggtgc tgaccgtgct gcaccaggat tggctgaacg gcaaggagta   1800
caagtgcaag gtgtccaaca aggccctgcc cgccccgatc gagaagacca tctccaaggc   1860
caagggccag ccacgcgagc cgcaggtgta caccctgcca ccctcccgcg atgagctgac   1920
caagaaccag gtgagcctga cctgcctggt gaagggcttc taccccctcgg atatcgccgt   1980
ggagtgggag agcaacggcc agccggagaa caactacaag accacccccac ccgtgctgga   2040
cagcgacggc agcttcttcc tgtacagcaa gctgaccgtg gacaagtcgc gctggcagca   2100
gggcaacgtg ttctcctgca gcgtgatgca cgaggccctg cacaaccact acacccagaa   2160
gagcctgagc ctgagccccg gcaagtaacc tgcagatctg cctcgactgt gccttctagt   2220
tgccagccat ctgttgtttg cccctccccc gtgccttcct tgaccctgga aggtgccact   2280
cccactgtcc tttcctaata aaatgaggaa attgcatcgc attgtctgag taggtgtcat   2340
tctattctgg ggggtggggt ggggcaggac agcaaggggg aggattggga agacaatagc   2400
aggcatgctg gggaggatct gatcctttcc tgggacccgg caagaaccaa aaactcactc   2460
tcttcaagga aatccgtaat gttaaacccg acacgatgaa gcttgtcgtt ggatggaaag   2520
gaaaagagtt ctacagggaa acttggaccc gcttcatgga agacagcttc cccattgtta   2580
acgaccaaga agtgatggat gttttccttg ttgtcaacat gcgtcccact agacccaacc   2640
gttgttacaa attcctggcc caacacgctc tgcgttgcga ccccgactat gtacctcatg   2700
acgtgattag gatcgtcgag ccttcatggg tgggcagcaa caacgagtac cgcatcagcc   2760
tggctaagaa gggcggcggc tgcccaataa tgaaccttca ctctgagtac accaactcgt   2820
tcgaacagtt catcgatcgt gtcatctggg agaacttcta caagcccatc gtttacatcg   2880
gtaccgactc tgctgaagag gaggaaattc tccttgaagt ttccctggtg ttcaaagtaa   2940
aggagtttgc accagacgca cctctgttca ctggtccggc gtattaaaac acgatacatt   3000
gttattagta catttattaa gcgctagatt ctgtgcgttg ttgatttaca gacaattgtt   3060
gtacgtattt taataattca ttaaatttat aatctttagg gtggtatgtt agagcgaaaa   3120
```

-continued

```
tcaaatgatt ttcagcgtct ttatatctga atttaaatat taaatcctca atagatttgt   3180
aaaataggtt tcgattagtt tcaaacaagg gttgtttttc cgaaccgatg gctggactat   3240
ctaatggatt ttcgctcaac gccacaaaac ttgccaaatc ttgtagcagc aatctagctt   3300
tgtcgatatt cgtttgtgtt ttgttttgta ataaaggttc gacgtcgttc aaaatattat   3360
gcgcttttgt atttctttca tcactgtcgt tagtgtacaa ttgactcgac gtaaacacgt   3420
taaataaagc ttggacatat ttaacatcgg gcgtgttagc tttattaggc cgattatcgt   3480
cgtcgtccca accctcgtcg ttagaagttg cttccgaaga cgattttgcc atagccacac   3540
gacgcctatt aattgtgtcg gctaacacgt ccgcgatcaa atttgtagtt gagctttttg   3600
gaattatttc tgattgcggg cgtttttggg cgggtttcaa tctaactgtg cccgatttta   3660
attcagacaa cacgttagaa agcgatggtg caggcggtgg taacatttca gacggcaaat   3720
ctactaatgg cggcggtggt ggagctgatg ataaatctac catcggtgga ggcgcaggcg   3780
gggctggcgg cggaggcgga ggcggaggtg gtggcggtga tgcagacggc ggtttaggct   3840
caaatgtctc tttaggcaac acagtcggca cctcaactat tgtactggtt tcgggcgccg   3900
tttttggttt gaccggtctg agacgagtgc gattttttc gtttctaata gcttccaaca   3960
attgttgtct gtcgtctaaa ggtgcagcgg gttgaggttc cgtcggcatt ggtggagcgg   4020
gcggcaattc agacatcgat ggtggtggtg gtggtggagg cgctggaatg ttaggcacgg   4080
gagaaggtgg tggcggcggt gccgccggta taatttgttc tggtttagtt tgttcgcgca   4140
cgattgtggg caccggcgca ggcgccgctg gctgcacaac ggaaggtcgt ctgcttcgag   4200
gcagcgcttg ggtggtggc aattcaatat tataattgga atacaaatcg taaaaatctg   4260
ctataagcat tgtaatttcg ctatcgttta ccgtgccgat atttaacaac cgctcaatgt   4320
aagcaattgt attgtaaaga gattgtctca agctccgcac gccgataaca agcctttca    4380
tttttactac agcattgtag tggcgagaca cttcgctgtc gtcgacgtac atgtatgctt   4440
tgttgtcaaa aacgtcgttg gcaagcttta aaatatttaa aagaacatct ctgttcagca   4500
ccactgtgtt gtcgtaaatg ttgtttttga taatttgcgc ttccgcagta tcgacacgtt   4560
caaaaaattg atgcgcatca attttgttgt tcctattatt gaataaataa gattgtacag   4620
attcatatct acgattcgtc atggccacca caaatgctac gctgcaaacg ctggtacaat   4680
tttacgaaaa ctgcaaaaac gtcaaaactc ggtataaaat aatcaacggg cgctttggca   4740
aaatatctat tttatcgcac aagcccacta gcaaattgta tttgcagaaa acaatttcgg   4800
cgcacaattt taacgctgac gaaataaaag ttcaccagtt aatgagcgac cacccaaatt   4860
ttataaaaat ctattttaat cacggttcca tcaacaacca agtgatcgtg atggactaca   4920
ttgactgtcc cgatttattt gaaacactac aaattaaagg cgagctttcg taccaacttg   4980
ttagcaatat tattagacag ctgtgtgaag cgctcaacga tttgcacaag cacaatttca   5040
tacacaacga cataaaactc gaaaatgtct tatatttcga agcacttgat cgcgtgtatg   5100
tttgcgatta cggattgtgc aaacacgaaa actcacttag cgtgcacgac ggcacgttgg   5160
agtattttag tccggaaaaa attcgacaca caactatgca cgtttcgttt gactggtacg   5220
cggcgtgtta acatacaagt tgctaaccgg cggttcgtaa tcatggtcat agctgtttcc   5280
tgtgtgaaat tgttatccgc tcacaattcc acacaacata cgagccggaa gcataaagtg   5340
taaagcctgg ggtgcctaat gagtgagcta actcacatta attgcgttgc gctcactgcc   5400
cgctttccag tcgggaaacc tgtcgtgcca gctgcattaa tgaatcggcc aacgcgcggg   5460
```

gagaggcggt ttgcgtattg ggcgctcttc cgcttcctcg ctcactgact cgctgcgctc 5520
ggtcgttcgg ctgcggcgag cggtatcagc tcactcaaag gcggtaatac ggttatccac 5580
agaatcaggg gataacgcag gaaagaacat gtgagcaaaa ggccagcaaa aggccaggaa 5640
ccgtaaaaag gccgcgttgc tggcgttttt ccataggctc cgcccccctg acgagcatca 5700
caaaaatcga cgctcaagtc agaggtggcg aaacccgaca ggactataaa gataccaggc 5760
gtttccccct ggaagctccc tcgtgcgctc tcctgttccg accctgccgc ttaccggata 5820
cctgtccgcc tttctccctt cgggaagcgt ggcgctttct catagctcac gctgtaggta 5880
tctcagttcg gtgtaggtcg ttcgctccaa gctgggctgt gtgcacgaac cccccgttca 5940
gcccgaccgc tgcgccttat ccggtaacta tcgtcttgag tccaacccgg taagacacga 6000
cttatcgcca ctggcagcag ccactggtaa caggattagc agagcgaggt atgtaggcgg 6060
tgctacagag ttcttgaagt ggtggcctaa ctacggctac actagaagga cagtatttgg 6120
tatctgcgct ctgctgaagc cagttacctt cggaaaaaga gttggtagct cttgatccgg 6180
caaacaaacc accgctggta gcggtggttt ttttgtttgc aagcagcaga ttacgcgcag 6240
aaaaaaagga tctcaagaag atcctttgat cttttctacg gggtctgacg ctcagtggaa 6300
cgaaaactca cgttaaggga ttttggtcat gagattatca aaaaggatct tcacctagat 6360
ccttttaaat taaaaatgaa gttttaaatc aatctaaagt atatatgagt aaacttggtc 6420
tgacagttac caatgcttaa tcagtgaggc acctatctca gcgatctgtc tatttcgttc 6480
atccatagtt gcctgactcc ccgtcgtgta gataactacg atacgggagg gcttaccatc 6540
tggccccagt gctgcaatga taccgcgaga cccacgctca ccggctccag atttatcagc 6600
aataaaccag ccagccggaa gggccgagcg cagaagtggt cctgcaactt tatccgcctc 6660
catccagtct attaattgtt gccgggaagc tagagtaagt agttcgccag ttaatagttt 6720
gcgcaacgtt gttgccattg ctacaggcat cgtggtgtca cgctcgtcgt ttggtatggc 6780
ttcattcagc tccggttccc aacgatcaag gcgagttaca tgatccccca tgttgtgcaa 6840
aaaagcggtt agctccttcg gtcctccgat cgttgtcaga agtaagttgg ccgcagtgtt 6900
atcactcatg gttatggcag cactgcataa ttctcttact gtcatgccat ccgtaagatg 6960
cttttctgtg actggtgagt actcaaccaa gtcattctga gaatagtgta tgcggcgacc 7020
gagttgctct tgcccggcgt caatacggga taataccgcg ccacatagca gaactttaaa 7080
agtgctcatc attggaaaac gttcttcggg gcgaaaactc tcaaggatct taccgctgtt 7140
gagatccagt tcgatgtaac ccactcgtgc acccaactga tcttcagcat cttttacttt 7200
caccagcgtt tctgggtgag caaaaacagg aaggcaaaat gccgcaaaaa agggaataag 7260
ggcgacacgg aaatgttgaa tactcatact cttccttttt caatattatt gaagcattta 7320
tcagggttat tgtctcatga gcggatacat atttgaatgt atttagaaaa ataaacaaat 7380
aggggttccg cgcacatttc cccgaaaagt gccacctgac gtctaagaaa ccattattat 7440
catgacatta acctataaaa ataggcgtat cacgaggccc tttcgtctcg cgcgtttcgg 7500
tgatgacggt gaaaacctct gacacatgca gctcccggag acggtcacag cttgtctgta 7560
agcggatgcc gggagcagac aagcccgtca gggcgcgtca gcgggtgttg gcgggtgtcg 7620
gggctggctt aactatgcgg catcagagca gattgtactg agagtgcacc atatgcggtg 7680
tgaaataccg cacagatgcg taaggagaaa ataccgcatc aggcgccatt cgccattcag 7740
gctgcgcaac tgttgggaag ggcgatcggt gcgggcctct tcgctattac gccagctggc 7800
gaaaggggga tgtgctgcaa ggcgattaag ttgggtaacg ccagggtttt cccagtcacg 7860

-continued

```
acgttgtaaa acgacggcca gtgccaagct ttactcgtaa agcgagttga aggatcatat   7920
ttagttgcgt ttatgagata agattgaaag cacgtgtaaa atgtttcccg cgcgttggca   7980
caactattta caatgcggcc aagttataaa agattctaat ctgatatgtt ttaaaacacc   8040
tttgcggccc gagttgtttg cgtacgtgac tagcgaagaa gatgtgtgga ccgcagaaca   8100
gatagtaaaa caaaacccta gtattggagc aataatcgat ttaaccaaca cgtctaaata   8160
ttatgatggt gtgcattttt tgcgggcggg cctgttatac aaaaaaattc aagtacctgg   8220
ccagactttg ccgcctgaaa gcatagttca agaatttatt gacacggtaa aagaatttac   8280
agaaaagtgt cccggcatgt tggtgggcgt gcactgcaca cacggtatta atcgcaccgg   8340
ttacatggtg tgcagatatt taatgcacac cctgggtatt gcgccgcagg aagccataga   8400
tagattcgaa aaagccagag gtcacaaaat tgaaagacaa aattacgttc aagatttatt   8460
aatttaatta atattatttg cattctttaa caaatacttt atcctatttt caaattgttg   8520
cgcttcttcc agcgaaccaa aactatgctt cgcttgctcc gtttagcttg tagccgatca   8580
gtggcgttgt tccaatcgac ggtaggatta ggccggatat tctccaccac aatgttggca   8640
acgttgatgt tacgtttatg cttttggttt tccacgtacg tcttttggcc ggtaatagcc   8700
gtaaacgtag tgccgtcgcg cgtcacgcac aacaccggat gtttgcgctt gtccgcgggg   8760
tattgaaccg cgcgatccga caaatccacc actttggcaa ctaaatcggt gacctgcgcg   8820
tctttttct gcattatttc gtctttcttt tgcatggttt cctggaagcc ggtgtacatg   8880
cggtttagat cagtcatgac gcgcgtgacc tgcaaatctt tggcctcgat ctgcttgtcc   8940
ttgatggcaa cgatgcgttc aataaactct tgttttttaa caagttcctc ggtttttttgc   9000
gccaccaccg cttgcagcgc gtttgtgtgc tcggtgaatg tcgcaatcag cttagtcacc   9060
aactgtttgc tctcctcctc ccgttgtttg atcgcgggat cgtacttgcc ggtgcagagc   9120
acttgaggaa ttacttcttc taaaagccat tcttgtaatt ctatggcgta aggcaatttg   9180
gacttcataa tcagctgaat cacgccggat ttagtaatga gcactgtatg cggctgcaaa   9240
tacagcgggt cgcccctttt cacgacgctg ttagaggtag ggcccccatt ttggatggtc   9300
tgctcaaata acgatttgta tttattgtct acatgaacac gtatagcttt atcacaaact   9360
gtatatttta aactgttagc gacgtccttg gccacgaacc ggacctgttg gtcgcgctct   9420
agcacgtacc gcaggttgaa cgtatcttct ccaaatttaa attctccaat tttaacgcga   9480
gccattttga tacacgtgtg tcgattttgc aacaactatt gtttttttaac gcaaactaaa   9540
cttattgtgg taagcaataa ttaaatatgg gggaacatgc gccgctacaa cactcgtcgt   9600
tatgaacgca gacggcgccg gtctcggcgc aagcggctaa aacgtgttgc gcgttcaacg   9660
cggcaaacat cgcaaaagcc aatagtacag ttttgatttg catattaacg gcgatttttt   9720
aaattatctt atttaataaa tagttatgac gcctacaact ccccgcccgc gttgactcgc   9780
tgcacctcga gcagttcgtt gacgccttcc tccgtgtggc cgaacacgtc gagcgggtgg   9840
tcgatgacca gcggcgtgcc gcacgcgacg cacaagtatc tgtacaccga atgatcgtcg   9900
ggcgaaggca cgtcggcctc caagtggcaa tattggcaaa ttcgaaaata tatacagttg   9960
ggttgtttgc gcatatctat cgtggcgttg ggcatgtacg tccgaacgtt gatttgcatg  10020
caagccgaaa ttaaatcatt gcgattagtg cgattaaaac gttgtacatc ctcgctttta  10080
atcatgccgt cgattaaatc gcgcaatcga gtcaagtgat caaagtgtgg aataatgttt  10140
tctttgtatt cccgagtcaa gcgcagcgcg tattttaaca aactagccat cttgtaagtt  10200
```

-continued agtttcattt aatgcaactt tatccaataa tatattatgt atcgcacgtc aagaattaac 10260
aatgcgcccg ttgtcgcatc tcaacacgac tatgatagag atcaaataaa gcgcgaatta 10320
aatagcttgc gacgcaacgt gcacgatctg tgcacgcgtt ccggcacgag ctttgattgt 10380
aataagtttt tacgaagcga tgacatgacc cccgtagtga caacgatcac gcccaaaaga 10440
actgccgact acaaaattac cgagtatgtc ggtgacgtta aaactattaa gccatccaat 10500
cgaccgttag tcgaatcagg accgctggtg cgagaagccg cgaagtatgg cgaatgcatc 10560
gtataacgtg tggagtccgc tcattagagc gtcatgttta gacaagaaag ctacatattt 10620
aattgatccc gatgatttta ttgataaatt gaccctaact ccatacacgg tattctacaa 10680
tggcggggtt ttggtcaaaa tttccggact gcgattgtac atgctgttaa cggctccgcc 10740
cactattaat gaaattaaaa attccaattt taaaaaacgc agcaagagaa acatttgtat 10800
gaaagaatgc gtagaaggaa agaaaaatgt cgtcgacatg ctgaacaaca agattaatat 10860
gcctccgtgt ataaaaaaaa tattgaacga tttgaaagaa aacaatgtac cgcgcggcgg 10920
tatgtacagg aagaggttta tactaaactg ttacattgca aacgtggttt cgtgtgccaa 10980
gtgtgaaaac cgatgtttaa tcaaggctct gacgcatttc tacaaccacg actccaagtg 11040
tgtgggtgaa gtcatgcatc ttttaatcaa atcccaagat gtgtataaac caccaaactg 11100
ccaaaaaatg aaaactgtcg acaagctctg tccgtttgct ggcaactgca agggtctcaa 11160
tcctatttgt aattattgaa taataaaaca attataaatg ctaaatttgt tttttattaa 11220
cgatacaaac caaacgcaac aagaacattt gtagtattat ctataattga aaacgcgtag 11280
ttataatcgc tgaggtaata tttaaaatca ttttcaaatg attcacagtt aatttgcgac 11340
aatataattt tattttcaca taaactagac gccttgtcgt cttcttcttc gtattccttc 11400
tctttttcat tttctcctc ataaaaatta acatagttat tatcgtatcc atatatgtat 11460
ctatcgtata gagtaaattt tttgttgtca taaatatata tgtctttttt aatggggtgt 11520
atagtaccgc tgcgcatagt ttttctgtaa tttacaacag tgctattttc tggtagttct 11580
tcggagtgtg ttgctttaat tattaaattt atataatcaa tgaatttggg atcgtcggtt 11640
ttgtacaata tgttgccggc atagtacgca gcttcttcta gttcaattac accatttttt 11700
agcagcaccg gattaacata actttccaaa atgttgtacg aaccgttaaa caaaaacagt 11760
tcacctccct tttctatact attgtctgcg agcagttgtt tgttgttaaa aataacagcc 11820
attgtaatga gacgcacaaa ctaatatcac aaactggaaa tgtctatcaa tatatagttg 11880
ctgatatctc cccagcatgc ctgctattgt cttcccaatc ctcccccttg ctgtcctgcc 11940
ccaccccacc ccccagaata gaatgacacc tactcagaca atgcgatgca atttcctcat 12000
tttattagga aaggacagtg ggagtggcac cttccagggt caaggaaggc acgggggagg 12060
ggcaaacaac agatggctgg caactagaag gcacagtcga ggcgaattct tagcactcgc 12120
cgcggttgaa ggacttggtc accgggctcg acaggccctg gtgggtcacc tcgcaggcgt 12180
acaccttgtg cttctcgtaa tcggccttgg acagggtcag ggtggagctc agcgagtagg 12240
tgctatcctt ggaatcctgc tcggtcacgc tctcctggga gttgccggac tgcagggcgt 12300
tatccacctt ccactgcacc ttggcctcgc gggggtagaa gttgttcagc aggcacacca 12360
cggaggcggt gccggacttc agctgctcgt ccgacggcgg gaagatgaac acggaggggg 12420
cggccacggt gcgcttgatc tccagcttgg tgccgccgcc gaaggtcggg gggttgctgg 12480
tccactgctg gcagtagtag gtggcggcat cctcggcctc cacgcgggag atggtcaggc 12540
tgtaggaggt gccgctgccg ctgccggaga agcgcaccgg cacgccggag gccagattgg 12600

-continued aggtggcgta gatccagggc ttcggggagc tgcctggctt ctgctggaac cagtgaatgt 12660
agctcacgct ggaggaggcg cggcaggtca tggtcacctt ctcgcccggc gaggcgctca 12720
ggatggcggg gctctgcgac agcacgatct ggccgcggct catgatcacg gaggcgctga 12780
tcagcaggaa ggagatgatc tgcacctgga aa 12812

<210> SEQ ID NO 4
<211> LENGTH: 31
<212> TYPE: DNA
<213> ORGANISM: Artificial Sequence
<220> FEATURE:
<223> OTHER INFORMATION: primer

<400> SEQUENCE: 4
gtttaaacgc ctcgactgtg ccttctagtt g 31

<210> SEQ ID NO 5
<211> LENGTH: 26
<212> TYPE: DNA
<213> ORGANISM: Artificial Sequence
<220> FEATURE:
<223> OTHER INFORMATION: primer

<400> SEQUENCE: 5
actagttccc cagcatgcct gctatt 26

<210> SEQ ID NO 6
<211> LENGTH: 34
<212> TYPE: DNA
<213> ORGANISM: Artificial Sequence
<220> FEATURE:
<223> OTHER INFORMATION: primer

<400> SEQUENCE: 6
aatggatccg gtaccaccat ggtgagcaag ggcg 34

<210> SEQ ID NO 7
<211> LENGTH: 36
<212> TYPE: DNA
<213> ORGANISM: Artificial Sequence
<220> FEATURE:
<223> OTHER INFORMATION: primer

<400> SEQUENCE: 7
ggcacttcgc gattacttgt acagctcgtc catgcc 36

<210> SEQ ID NO 8
<211> LENGTH: 33
<212> TYPE: DNA
<213> ORGANISM: Artificial Sequence
<220> FEATURE:
<223> OTHER INFORMATION: primer

<400> SEQUENCE: 8
ttatctcgcg aaccatgact caacgcttgt tcg 33

<210> SEQ ID NO 9
<211> LENGTH: 26
<212> TYPE: DNA
<213> ORGANISM: Artificial Sequence
<220> FEATURE:
<223> OTHER INFORMATION: primer

<400> SEQUENCE: 9
atcacggaat gcctcgggta cgtatg 26

<210> SEQ ID NO 10
<211> LENGTH: 26
<212> TYPE: DNA
<213> ORGANISM: Artificial Sequence
<220> FEATURE:
<223> OTHER INFORMATION: primer

<400> SEQUENCE: 10
gctggtcaaa catacgtacc cgaggc 26

<210> SEQ ID NO 11
<211> LENGTH: 34
<212> TYPE: DNA
<213> ORGANISM: Artificial Sequence
<220> FEATURE:
<223> OTHER INFORMATION: primer

<400> SEQUENCE: 11
tgggccctta ctcctctcta acacgagatt ccca 34

<210> SEQ ID NO 12
<211> LENGTH: 35
<212> TYPE: DNA
<213> ORGANISM: Artificial Sequence
<220> FEATURE:
<223> OTHER INFORMATION: primer

<400> SEQUENCE: 12
attgtgaatt cgcctcgact gtgccttcta gttgc 35

<210> SEQ ID NO 13
<211> LENGTH: 32
<212> TYPE: DNA
<213> ORGANISM: Artificial Sequence
<220> FEATURE:
<223> OTHER INFORMATION: primer

<400> SEQUENCE: 13
taattgatat ctccccagca tgcctgctat tg 32

<210> SEQ ID NO 14
<211> LENGTH: 51
<212> TYPE: DNA
<213> ORGANISM: Artificial Sequence
<220> FEATURE:
<223> OTHER INFORMATION: primer

<400> SEQUENCE: 14
gccgcgctag catcatggag ataattaaaa tgataaccat ctcgcaaata a 51

<210> SEQ ID NO 15
<211> LENGTH: 32
<212> TYPE: DNA
<213> ORGANISM: Artificial Sequence
<220> FEATURE:
<223> OTHER INFORMATION: primer

<400> SEQUENCE: 15
aatttgcggc cgcagcgccc gatggtggga cg 32

<210> SEQ ID NO 16
<211> LENGTH: 50
<212> TYPE: DNA
<213> ORGANISM: Artificial Sequence
<220> FEATURE:
<223> OTHER INFORMATION: primer

<400> SEQUENCE: 16
gggcctcgag atcatggaga taattaaaat gataaccatc tcgcaaataa 50

<210> SEQ ID NO 17
<211> LENGTH: 37
<212> TYPE: DNA
<213> ORGANISM: Artificial Sequence
<220> FEATURE:
<223> OTHER INFORMATION: primer

<400> SEQUENCE: 17
atttgcatgc gtttaaacag cgcccgatgg tgggacg 37

<210> SEQ ID NO 18
<211> LENGTH: 32
<212> TYPE: DNA
<213> ORGANISM: Artificial Sequence
<220> FEATURE:
<223> OTHER INFORMATION: primer

<400> SEQUENCE: 18
gccgcgctag caaattccgt tttgcgacga tg 32

<210> SEQ ID NO 19
<211> LENGTH: 51
<212> TYPE: DNA
<213> ORGANISM: Artificial Sequence
<220> FEATURE:
<223> OTHER INFORMATION: primer

<400> SEQUENCE: 19
aatttgcggc cgcgtttaaa ttgtgtaatt tatgtagctg taatttttac c 51

<210> SEQ ID NO 20
<211> LENGTH: 31
<212> TYPE: DNA
<213> ORGANISM: Artificial Sequence
<220> FEATURE:
<223> OTHER INFORMATION: primer

<400> SEQUENCE: 20
gggcctcgag aaattccgtt ttgcgacgat g 31

<210> SEQ ID NO 21
<211> LENGTH: 56
<212> TYPE: DNA
<213> ORGANISM: Artificial Sequence
<220> FEATURE:
<223> OTHER INFORMATION: primer

<400> SEQUENCE: 21
atttgcatgc gtttaaacgt ttaaattgtg taatttatgt agctgtaatt tttacc 56

<210> SEQ ID NO 22
<211> LENGTH: 29
<212> TYPE: DNA
<213> ORGANISM: Artificial Sequence
<220> FEATURE:
<223> OTHER INFORMATION: primer

<400> SEQUENCE: 22
atttgtattt aatcaatcga accgtgcac 29

-continued

```
<210> SEQ ID NO 23
<211> LENGTH: 30
<212> TYPE: DNA
<213> ORGANISM: Artificial Sequence
<220> FEATURE:
<223> OTHER INFORMATION: primer

<400> SEQUENCE: 23

gattgggaat ctcgtgttag agaggagtaa                                    30


<210> SEQ ID NO 24
<211> LENGTH: 24
<212> TYPE: DNA
<213> ORGANISM: Artificial Sequence
<220> FEATURE:
<223> OTHER INFORMATION: primer

<400> SEQUENCE: 24

atcttcttca aggacgacgg caac                                          24


<210> SEQ ID NO 25
<211> LENGTH: 34
<212> TYPE: DNA
<213> ORGANISM: Artificial Sequence
<220> FEATURE:
<223> OTHER INFORMATION: primer

<400> SEQUENCE: 25

agcaagatgg taagcgctat tgttttatat gtgc                               34


<210> SEQ ID NO 26
<211> LENGTH: 30
<212> TYPE: DNA
<213> ORGANISM: Artificial Sequence
<220> FEATURE:
<223> OTHER INFORMATION: primer

<400> SEQUENCE: 26

agatgggtat gaaaccatac aacaagtgtg                                    30


<210> SEQ ID NO 27
<211> LENGTH: 28
<212> TYPE: DNA
<213> ORGANISM: Artificial Sequence
<220> FEATURE:
<223> OTHER INFORMATION: primer

<400> SEQUENCE: 27

cgctaccata atctttgttg aatcgatg                                      28
```

COMPOSITIONS AND METHODS FOR REDUCING FUCOSYLATION OF GLYCOPROTEINS IN INSECT CELLS AND METHODS OF USE THEREOF FOR PRODUCTION OF RECOMBINANT GLYCOPROTEINS

PRIORITY CLAIM

This application is a continuation application of U.S. patent application Ser. No. 14/504,195, filed Oct. 1, 2014, which claims priority to U.S. Provisional Application No. 61/885,294 filed Oct. 1, 2013. These applications are incorporated herein by reference as though set forth in full.

STATEMENT OF RIGHTS TO INVENTIONS MADE UNDER FEDERALLY SPONSORED RESEARCH

This invention was made with government support under Grant No. GM049734 awarded by the National Institutes of Health. The government has certain rights in the invention.

FIELD OF THE INVENTION

This invention relates to the fields of molecular biology and production of glycoproteins lacking fucosylation. More specifically, the invention provides compositions and methods for expressing a GDP-4-dehydro-6-deoxy-D-mannose reductase enzyme encoded by a recombinant baculovirus vector that blocks the production of GDP-L-fucose and generates a molecule lacking or having a reduced amount of fucose.

BACKGROUND OF THE INVENTION

Numerous publications and patent documents, including both published applications and issued patents, are cited throughout the specification in order to describe the state of the art to which this invention pertains. Each of these citations is incorporated herein by reference as though set forth in full.

In view of bioinformatic analyses suggesting that well over half of all human proteins are glycosylated, the ability to support glycosylation is an increasingly significant attribute of recombinant protein production systems, including insect-based systems, such as the baculovirus-insect cell system (reviewed by Jarvis 2009; Usami et al. 2010). The native human protein glycosylation process often results in the addition of terminally sialylated N-glycans that dramatically influence key properties, such as the in vivo half-lives, of glycoproteins in the human body (Ngantung et al. 2006; reviewed by Varki and Gagneux 2012). Most investigators know that insect-based systems, including the baculovirus-insect cell expression system, support recombinant protein glycosylation, but it is also important to recognize that these systems cannot produce human-type, terminally sialylated N-glycans (Marchal et al. 2001; Hillar and Jarvis 2010). This limitation has been addressed by glycoengineering baculovirus vectors and/or insect cell lines to encode and express mammalian glycogenes that extend endogenous insect cell N-glycan processing capabilities (Jarvis and Finn 1996; Wagner et al. 1996; Hollister et al. 1998; Ailor et al. 2000; Seo et al. 2001; Jarvis et al. 2001; Hollister and Jarvis 2001; Hollister et al. 2002; Aumiller et al. 2003; Tomiya et al. 2003; Chang et al. 2003; Yun et al. 2005; Hill et al. 2006; Okada et al. 2010; Aumiller et al. 2012; Geisler and Jarvis 2012; Palmberger et al. 2012; Mabashi-Asazuma et al. 2013). These efforts ultimately yielded new baculovirus-insect systems that can produce recombinant glycoproteins with human-type, terminally sialylated N-glycans. This was an important step towards the broader goal of extending the utility of the baculovirus-insect cell system to include therapeutic glycoprotein production, which is not currently considered to be a legitimate application of this system. In order to finally achieve this goal, however, it also will be necessary to eliminate core α1,3-fucosylation of recombinant glycoproteins in certain insect cell lines, including some that are commonly used as hosts for baculovirus vectors, as this modification generates a highly immunogenic carbohydrate epitope (reviewed by Fotisch and Vieths 2001; Altmann et al. 2007).

There are two distinct types of N-glycan core fucosylation involving the addition of either α1,6- or α1,3-linked fucose residues to the core N-acetylglucosamine. Humans encode a single core fucosyltransferase, FUT8, which can only add α1,6-linked fucose residues, but many insects encode two core fucosyltransferases, FucT6 and FucTA, which can add α1,6- or α1,3-linked fucose residues, respectively, to the core N-acetylglucosamine (FIG. 1A; Fabini et al. 2001; Paschinger et al. 2005; Rendić et al. 2007). Because humans have no FucTA counterpart, we cannot produce core α1,3-fucosylated N-glycoproteins and, as a result, the core α1,3-fucosylated sugar epitope is immunogenic for many people. In fact, the presence of this epitope on bee venom glycoproteins accounts for the life-threatening allergic responses, such as anaphylactic shock, induced by bee stings in some humans (King et al. 1976; Prenner et al. 1992; Kubelka et al. 1995; reviewed by Altmann et al. 2007). In addition, pre-existing human antibodies against the immunogenic sugar epitope can give false positive results in diagnostic tests that use α1,3-fucosylated recombinant glycoproteins produced in the baculovirus-insect cell system (Hancock et al. 2008; Seismann et al. 2010).

Among the insect cell lines commonly used as hosts for baculovirus-mediated recombinant protein production, BTI-Tn-5B1-4 (Wickham et al. 1992; commercialized as High Five™ by Life Technologies Inc., Carlsbad, Calif.), which is derived from *Trichoplusia ni*, produces high levels of the core α1,3-fucosylated N-glycan epitope, whereas Sf9 (Summers and Smith 1987), derived from *Spodoptera frugiperda*, and BmN (Maeda 1989), derived from *Bombyx mori*, do not (Rudd et al. 2000; Hancock et al. 2008; Seismann et al. 2010; Blank et al. 2011; Palmberger et al. 2011). Importantly, the capacity to produce immunogenic, core α1,3-fucosylated N-glycans trumps the opportunity to exploit the potentially higher recombinant glycoprotein production capacity of insect cell lines derived from *Trichoplusia ni*, such as High Five™ (Davis et al. 1992; Krammer et al. 2010).

While core α1,3-fucosylation is a relatively host-specific modification, core α1,6-fucosylation is a common feature of recombinant glycoproteins produced by all insect cell lines, including those used as hosts for baculovirus vectors. As noted above, core α1,6-fucosylation also occurs in humans and, therefore, does not produce an immunogenic sugar epitope. Nevertheless, this form of core fucosylation is also biotechnologically significant because it inhibits the effector functions of certain types of therapeutic antibodies (Shields et al. 2002; Shinkawa et al. 2003; reviewed by Satoh et al. 2006; Jefferis 2009), which comprise a large and growing share of the human biologics market (reviewed by Elvin et al. 2013). The inhibition of antibody effector functions by core fucosylation stimulated efforts to block pathways responsible for this modification and enable production of non-fucosylated antibodies in mammalian cell expression systems (FIG. 1B). Various approaches included repressing or eliminating FUT8 gene expression (Yamane-Ohnuki et al. 2004; Imai-Nishiya et al. 2007; Malphettes et al. 2010), overexpressing upstream processing enzymes to produce N-glycan structures that are not recognized as acceptor substrates (Ferrara et al. 2006; Zhong et al. 2012), and blocking production of GDP-L-fucose, which is required as the donor substrate for fucosylation by FUT8 (Imai-Nishiya et al. 2007; Kanda et al. 2007; von Horsten et al. 2010). To date, however, there have been no reported efforts to block recombinant glycoprotein fucosylation in any insect-based system, including the baculovirus-insect cell system, despite the arguably more serious problem of immunogenicity associated with core α1,3-fucosylation mediated by some insect and insect cell types.

SUMMARY OF THE INVENTION

In accordance with the present invention, a recombinant baculovirus expression vector for transient expression of GDP-4-dehydro-6-deoxy-D-mannose reductase (RMD) in an insect cell is disclosed. In one embodiment, the vector comprises the following operably linked components, i) an expression control sequence functional early in infection operably linked to a codon optimized RMD encoding nucleic acid; and ii) an insertion site suitable for insertion of one or more nucleic acids encoding at least one heterologous protein of interest. In a particularly preferred embodiment, the vector is AcRMD shown in FIG. 14. In another embodiment, the vector further comprises a nucleic acid sequence encoding at least one heterologous protein of interest operably linked to a promoter which is active later in infection, e.g., a p6.9 or polyhedrin promoter inserted at said insertion site.

In certain embodiments, the expression control sequence includes a promoter selected from the group consisting of baculovirus immediate early and delayed early promoters and an inducible promoter. In a preferred embodiment, the expression control sequence also includes an enhancer element.

The vectors of the invention have utility in the production of non-fucosylated therapeutic proteins. Such therapeutic proteins include, without limitation, an antibody, a subunit vaccine, an antibiotic, a cytokine, an anticoagulant, a viral antigen, an enzyme, a hormone, or a blood clotting factor. Cells useful in the methods disclosed herein include, for example, Sf9, Sf21, expresSF+®, Tn368, High Five®, Tni PRO®, Ea4, Ao38, BmN, S2, and S2R+ cells.

Also provided is a method for producing at least one molecule of interest (e.g., a therapeutic protein) lacking fucose, comprising providing insect cells and introducing a baculovirus comprising at least one nucleic acid molecule encoding a codon optimized enzyme GDP-4-dehydro-6-deoxy-D-mannose reductase (RMD) operably driven by an immediate early expression control sequence for expression immediately after infection or an inducible promoter, and at least one additional nucleic acid encoding a protein of interest driven by a promoter active later in infection that may or may not be on the same vector encoding RMD. Using this approach, inhibition of fucosylation is stabilized permitting production of a non-fucosylated protein of interest. The infected cells are incubated under conditions wherein GDP-4-dehydro-6-deoxy-D-mannose reductase blocks the production of GDP-L-fucose, and said at least one protein of interest is produced lacking fucose. Following production, the non-fucosylated protein of interest is isolated.

In yet another aspect, a kit for the production of at least one protein of interest lacking fucose is provided comprising at least one recombinant baculovirus comprising at least one nucleic acid molecule encoding the codon optimized enzyme GDP-4-dehydro-6-deoxy-D-mannose reductase (RMD) operably driven by an immediate early expression control sequence for expression immediately after infection, thereby stabilizing inhibition of fucosylation, and an insertion site for at least one additional nucleic acid molecule encoding at least one protein of interest, for production of non-fucosylated proteins of interest. The kit may also contain insect cells and at least one additional baculoviral vector comprising a promoter suitable to drive expression of the protein of interest and an insertion site for the at least one nucleic acid encoding the protein of interest.

In a further embodiment, the invention provides a method for production of a non-fucosylated protein in insect larvae. An exemplary method entails providing insect larvae and introducing therein a baculovirus comprising at least one nucleic acid molecule encoding a codon optimized enzyme GDP-4-dehydro-6-deoxy-D-mannose reductase (RMD) operably driven by an immediate early expression control sequence for expression immediately after infection or an inducible promoter, thereby stabilizing inhibition of fucosylation, and at least one additional nucleic acid molecule encoding at least one protein of interest driven by an promoter active later in infection, thereby producing non-fucosylated proteins wherein said additional nucleic acid is present on the same baculovirus encoding RMD or is present on a second baculovirus vector. The infected larvae are then incubated under conditions wherein GDP-4-dehydro-6-deoxy-D-mannose reductase blocks the production of GDP-L-fucose, and said at least one protein of interest is produced lacking fucose. The method further includes the step of isolating the protein of interest.

The bars indicate the number of substitutions per site. Abbreviations: Hs, *Homo sapiens*; Mm, *Mus musculus*; Bt, *Bos taurus*; Gg, *Gallus gallus*; Xl, *Xenopus laevis*; Dr, *Danio rerio*; Dp, *Daphnia pulex*; Ce, *Caenorhabditis elegans*; At, *Arabidopsis thaliana.*

Figure 4B:
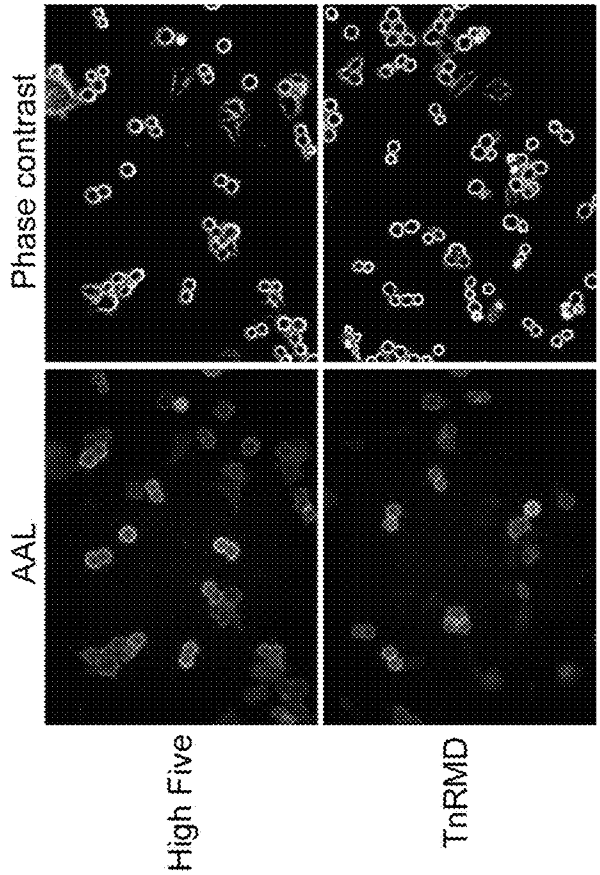
Figure 4A:
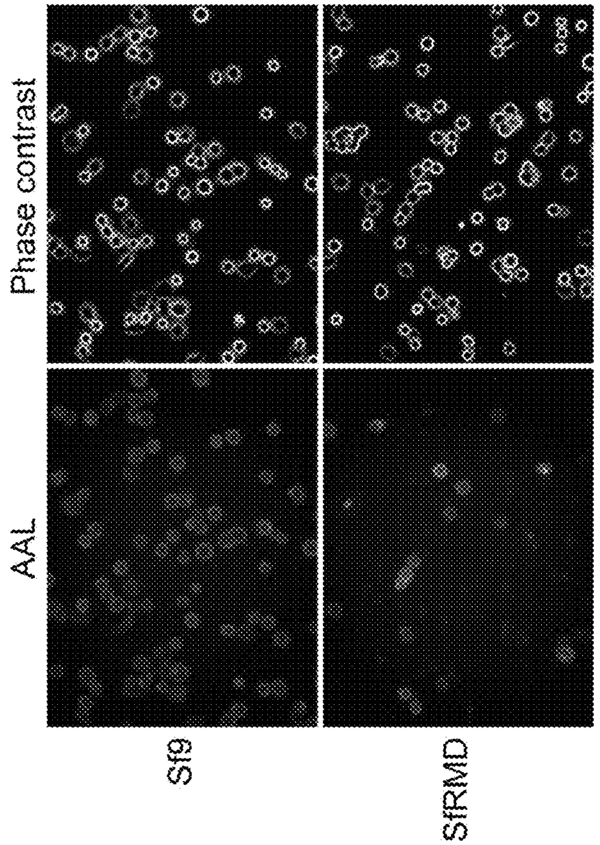

FIGS. 4A-4B. Cell surface fucosylation. Sf9 and polyclonal SfRMD (FIG. 4A) or High Five™ and polyclonal TnRMD (FIG. 4B) cells were seeded into culture plates, and then stained with AAL, as described in Materials and methods. The cell surface staining patterns are shown alongside corresponding phase contrast micrographs, as indicated.

Figure 5:
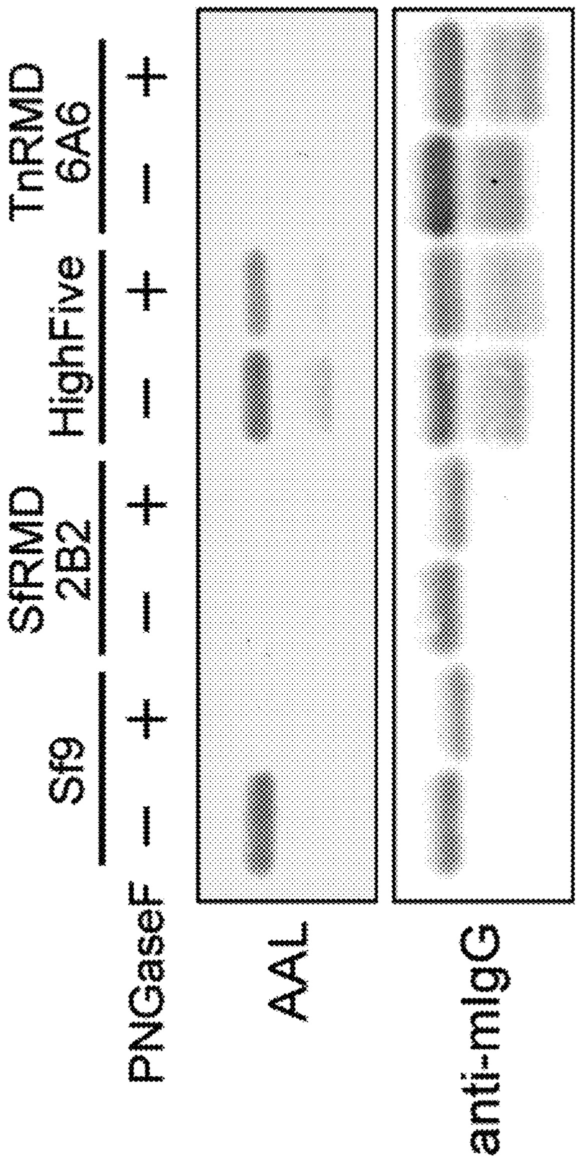

FIG. 5. Sf9, SfRMD 2B2, High Five™ and TnRMD 6A6 cells were infected with a baculovirus vector encoding a 6×HIS-tagged Fc domain of mouse IgG2a (mIgG2a-Fc) under the control of the baculovirus p6.9 promoter and the mIgG2a-Fc was affinity-purified from the extracellular fractions, as described in Materials and methods. Samples were then treated with peptide-$N^4$-(N-acetyl-β-glucosaminyl) asparagine amidase (PNGase)-F or reaction buffer alone, resolved by SDS-PAGE, transferred to a PVDF membrane, and probed with AAL to detect fucose or with anti-mouse IgG to detect the protein.

Figure 6:
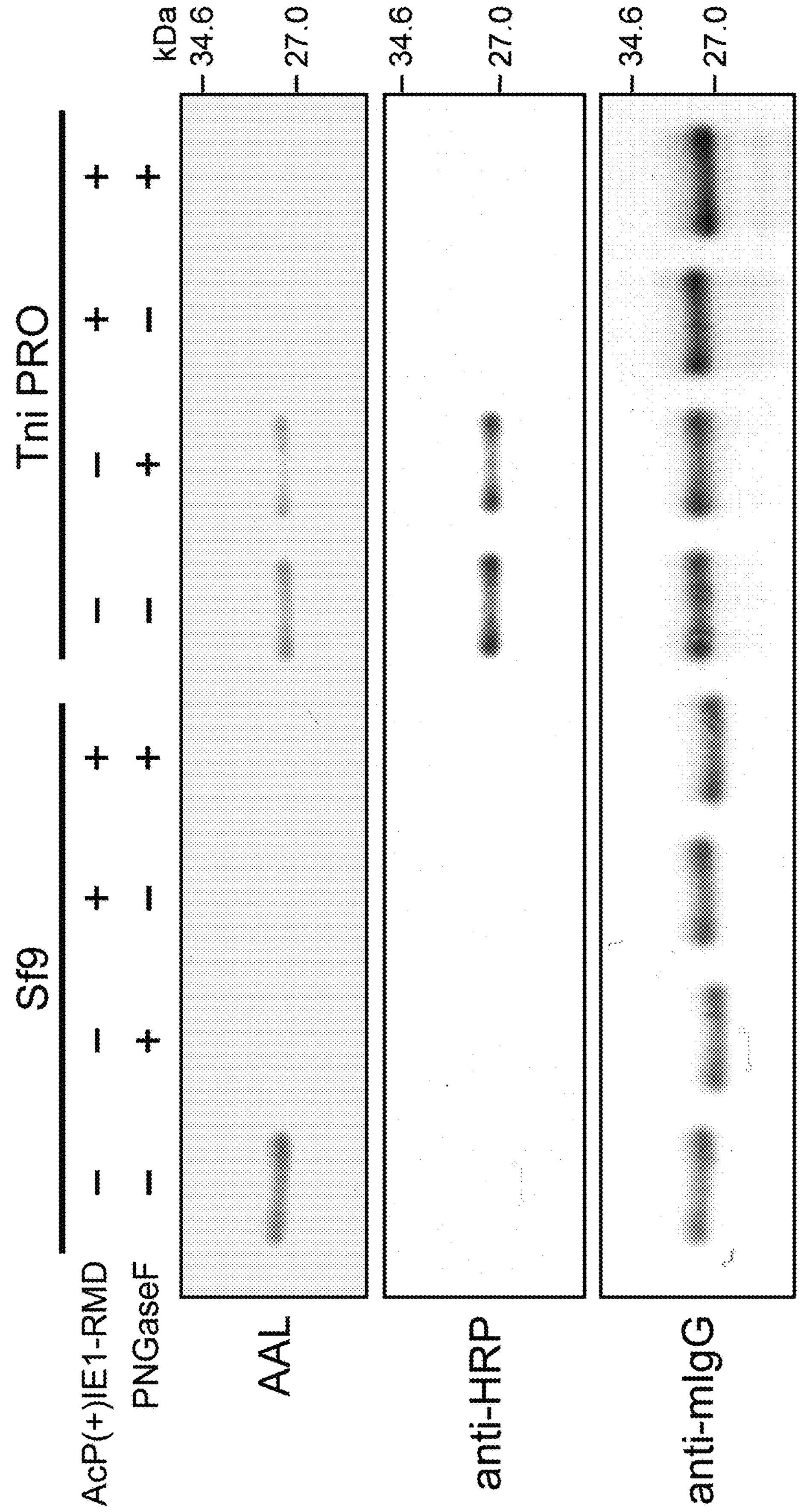

FIG. 6. Impact of AcP(+)IE1-RMD co-infection on mIgG2a-Fc fucosylation. Sf9 or Tni PRO™ cells were infected with Acp6.9-mIgG2a-Fc, a recombinant baculovirus encoding mIgG2a-Fc, or with equal doses of Acp6.9-mIgG2a-Fc and AcP(+)IE1-RMD, a recombinant baculovirus encoding Rmd. The cell-free media were harvested at 48 hours post-infection and used to affinity purify each mIgG2a-Fc preparation for lectin blotting analysis with AAL (specific for fucose) or western blotting analysis with anti-HRP (specific for core α1,3 fucose) or anti-mouse IgG with (+) or without (−) PNGase-F pre-treatment, as indicated.

Figure 7A:
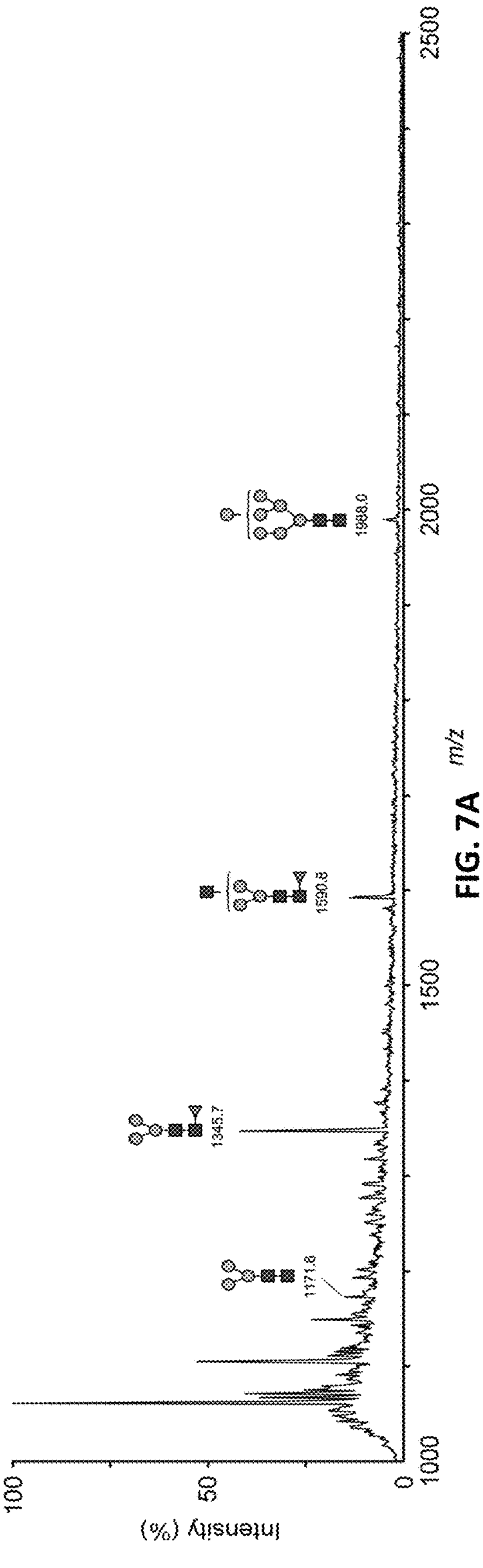
Figure 7B:
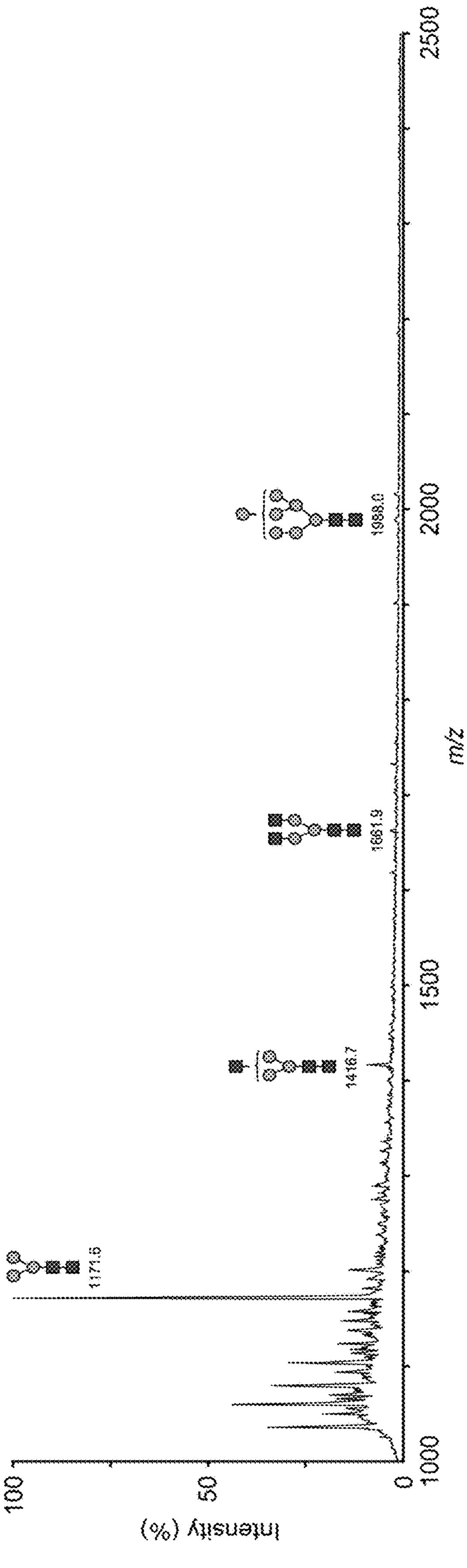
Figure 7C:
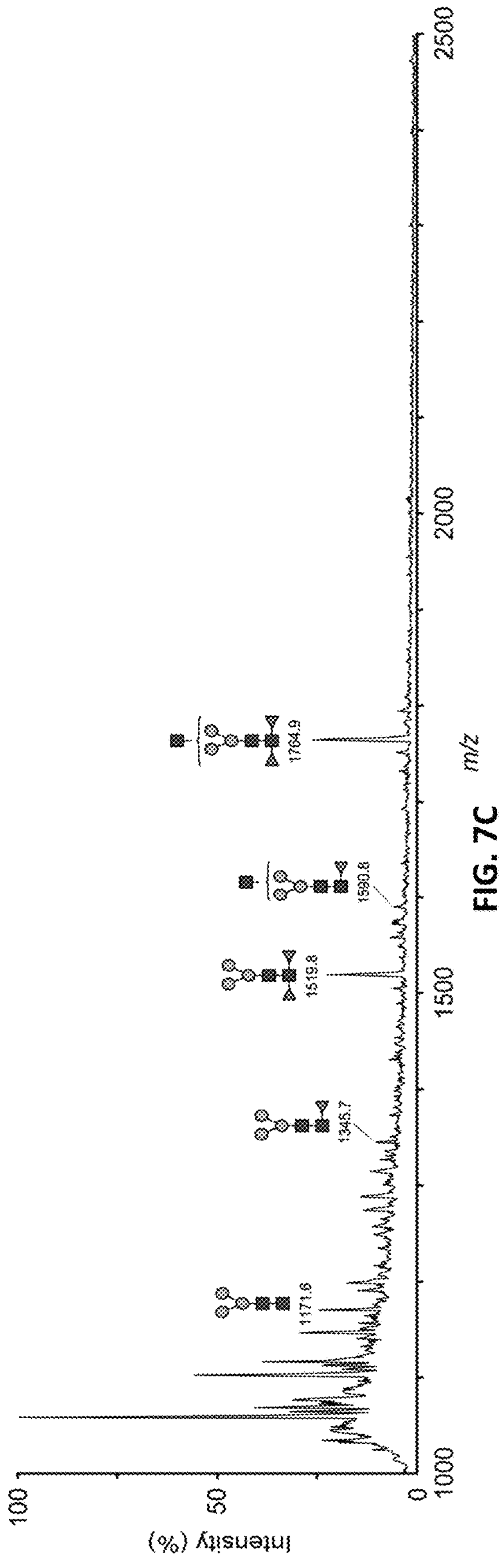
Figure 7D:
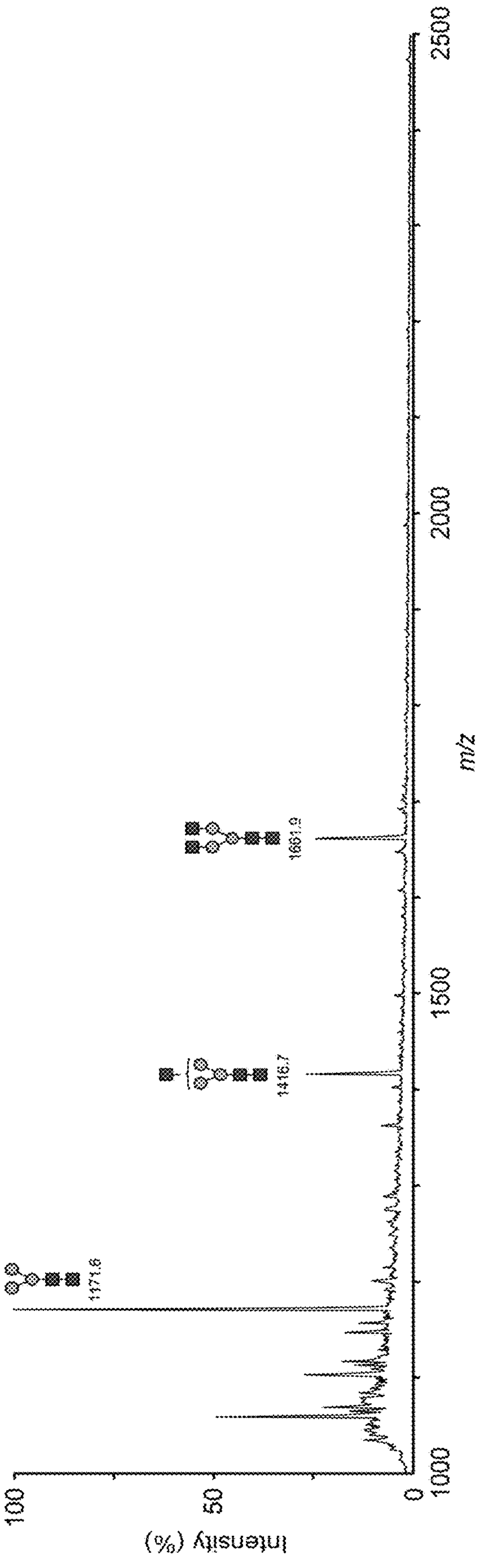

FIGS. 7A-7D. N-glycan profiling of various mIgG2a-Fc preparations by MALDI-TOF MS. mIgG2a-Fc preparations were produced and purified from Sf9 and Tni PRO™ cells infected with Acp6.9-mIgG2a-Fc alone or Acp6.9-mIgG2a-Fc and AcP(+)IE1-RMD, as described in the legend to FIG. 6. PNGaseAr was used to remove the N-glycans, which were then recovered, permethylated, and analyzed by MALDI-TOF MS, as described in Materials and methods. mIgG2a-Fc from Sf9 cells infected with Acp6.9-mIgG2a-Fc alone (FIG. 7A), Sf9 cells co-infected with Acp6.9-mIgG2a-Fc and AcP(+)IE1-RMD (FIG. 7B), Tni PRO™ cells infected with Acp6.9-mIgG2a-Fc alone (FIG. 7C), or Tni PRO™ cells co-infected with Acp6.9-mIgG2a-Fc and AcP (+)IE1-RMD (FIG. 7D). All molecular ions were detected as $[M+Na]^+$, assigned, and annotated using the standard cartoon symbolic representations.

Figure 8:
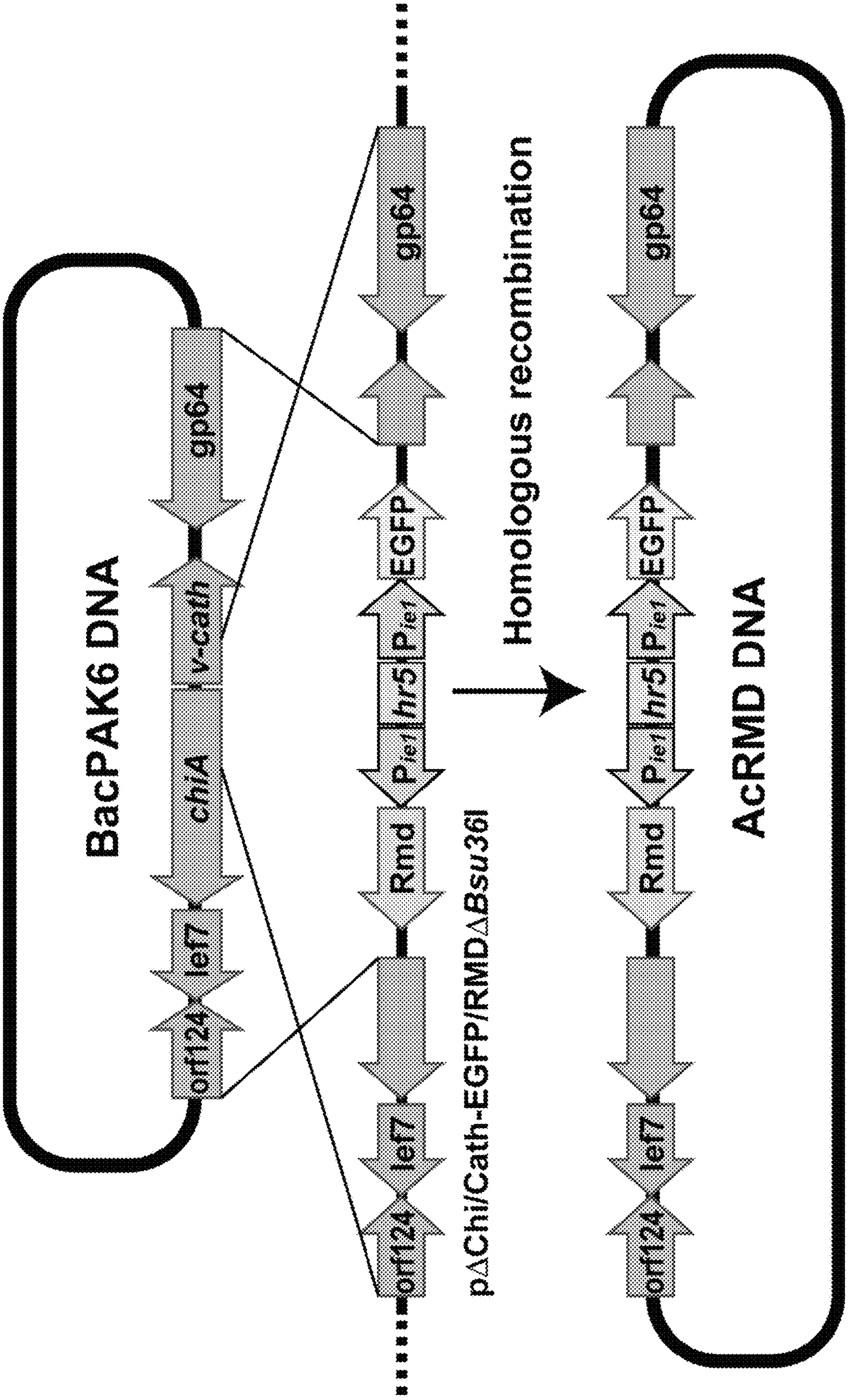

FIG. 8. Genetic maps of parental baculoviral vector, baculovirus transfer plasmid, and AcRMD. The new baculovirus vector designated AcRMD was isolated by replacing the 5' regions of the AcMNPV chiA and v-cath genes in BacPAK6 (Kitts and Possee 1993) baculoviral DNA with an expression cassette encoding EGFP and Rmd under the control of dual, back-to-back ie1 promoters separated by the AcMNPV hr5 enhancer, as described in Materials and methods.

Figure 9:
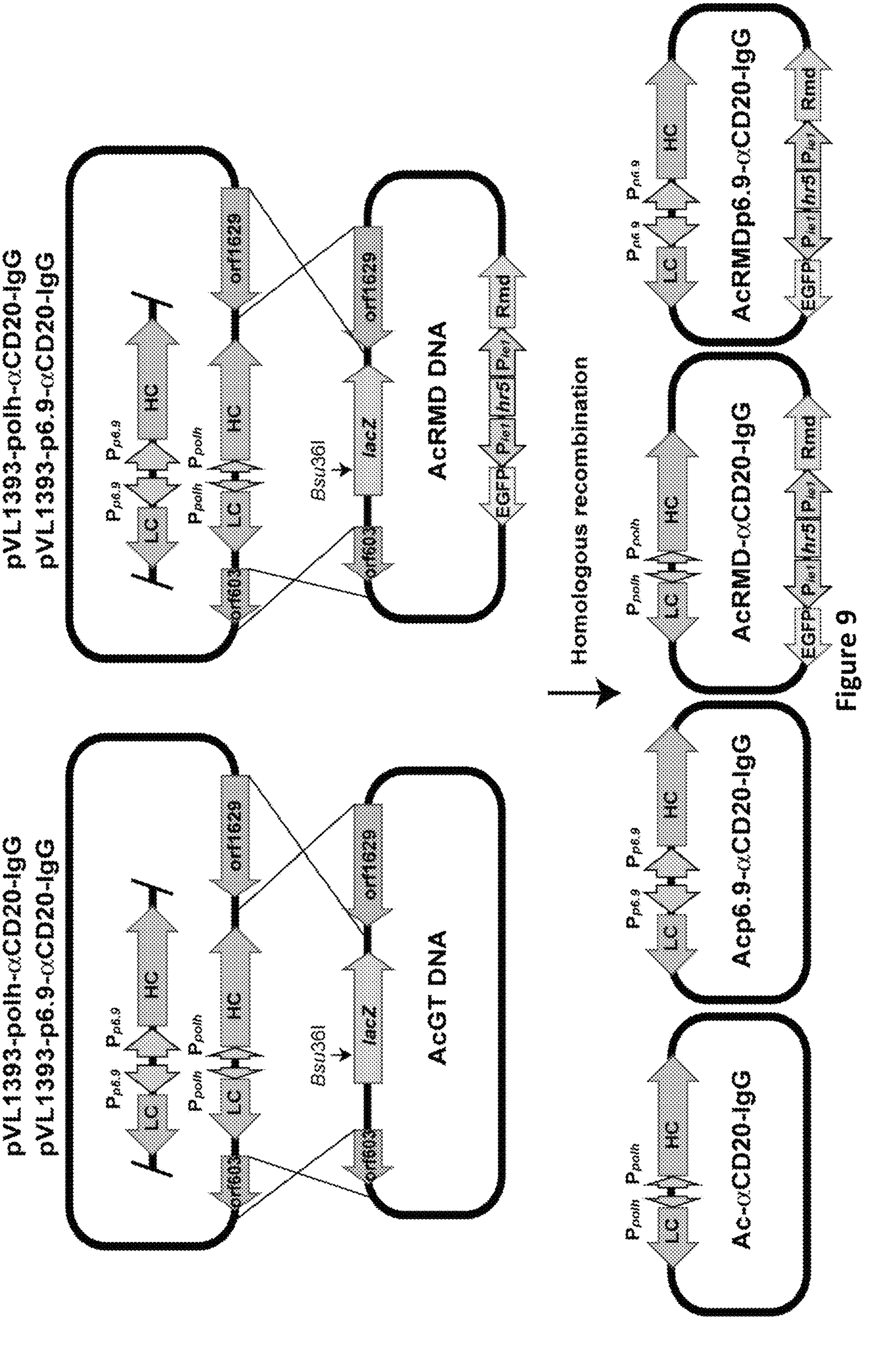

FIG. 9. Genetic maps of recombinant baculoviruses encoding anti-CD20-IgG. The recombinant baculoviruses designated Ac-αCD20-IgG and Acp6.9-αCD20-IgG were isolated by using homologous recombination to replace the lacZ sequence in the parental baculovirus, AcGT (Toth et al, 2011), with expression cassettes encoding the anti-CD20-IgG heavy and light chains under the control of dual, back-to-back polyhedrin or p6.9 promoters separated by the second intron of the *Drosophila melanogaster* white gene, respectively. Similarly, the recombinant baculoviruses designated AcRMD-αCD20-IgG and AcRMDp6.9-αCD20-IgG were isolated by using homologous recombination to replace the lacZ sequence of the parental baculovirus, AcRMD (this study), with the same expression cassettes used to isolate Ac-αCD20-IgG and Acp6.9-αCD20-IgG.

Figure 10:
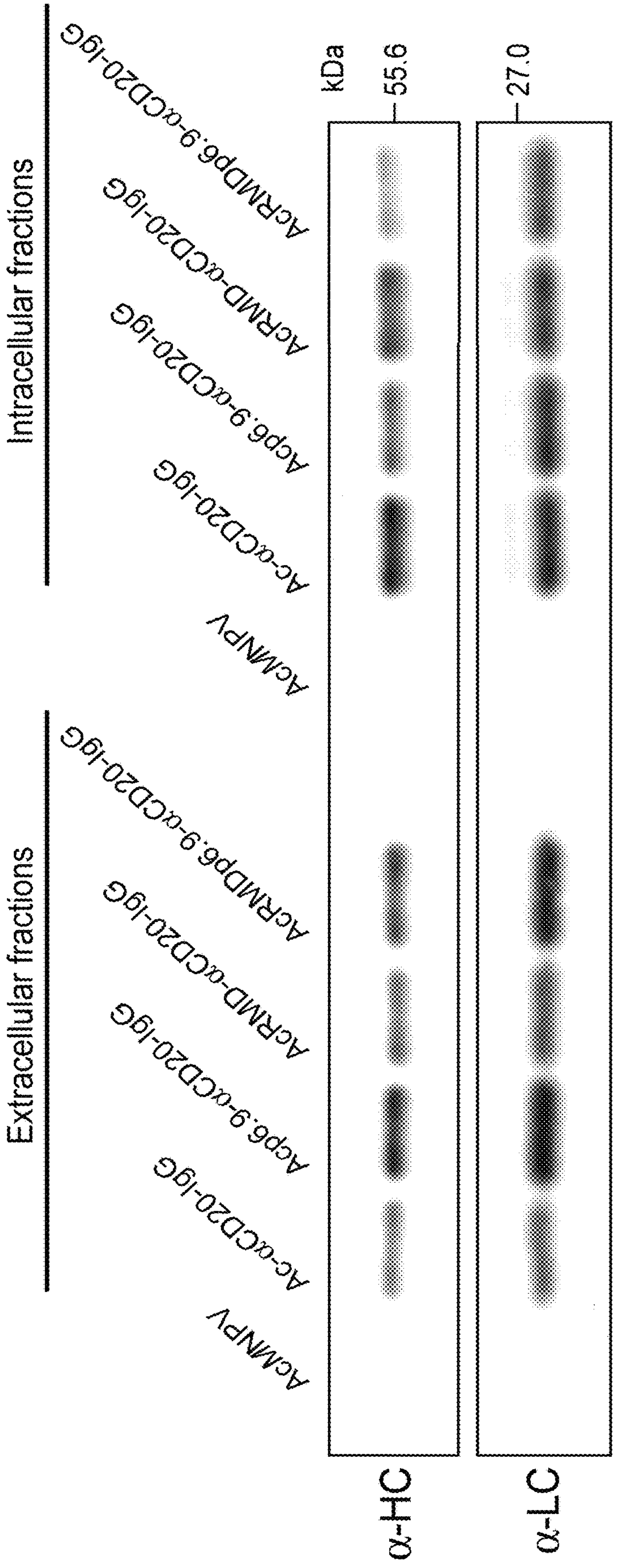

FIG. 10. Expression and secretion of anti-CD20-IgG under the control of late or very late baculoviral promoters. Sf9 cells were infected with AcMNPV, Ac-CD20-IgG, Acp6.9-αCD20-IgG, AcRMD-αCD20-IgG, or AcRMDp6.9-αCD20-IgG. At 48 hours post-infection, the cell-free culture media were collected as the extracellular fraction, the cells were lysed, and the clarified supernatants were collected as the intracellular fraction. Proteins were resolved by SDS-PAGE, transferred to a PVDF membrane, and probed with anti-human IgG Fc-specific (α-HC) or anti-human IgG κ chain-specific antibodies (α-LC).

Figure 11B:
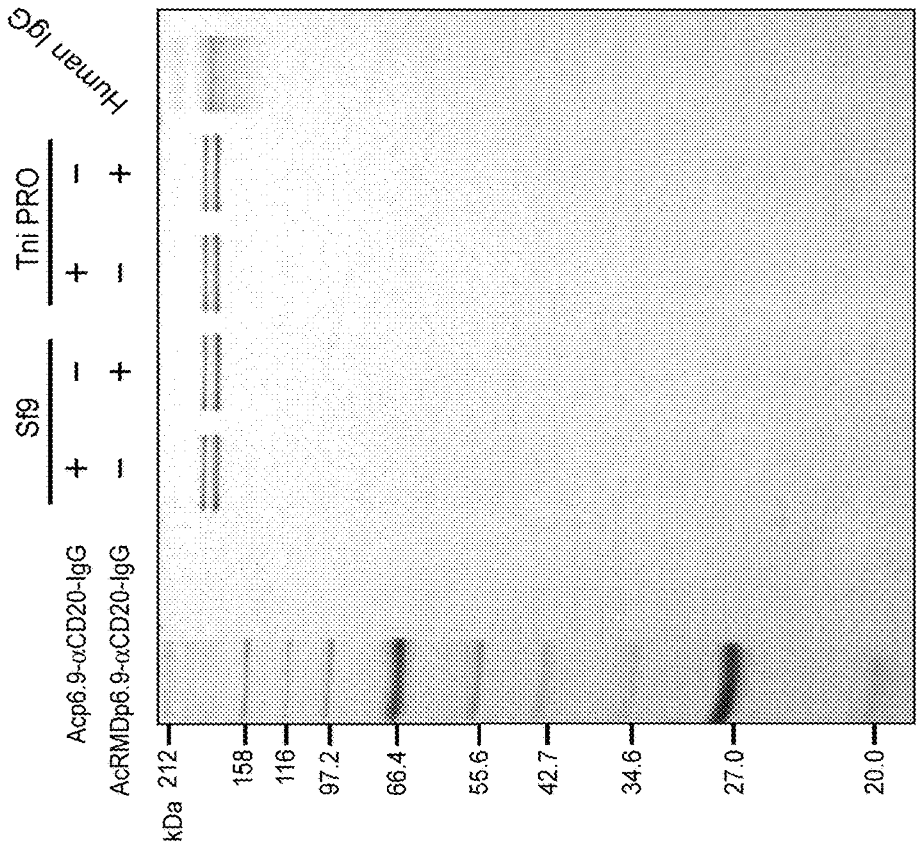
Figure 11A:
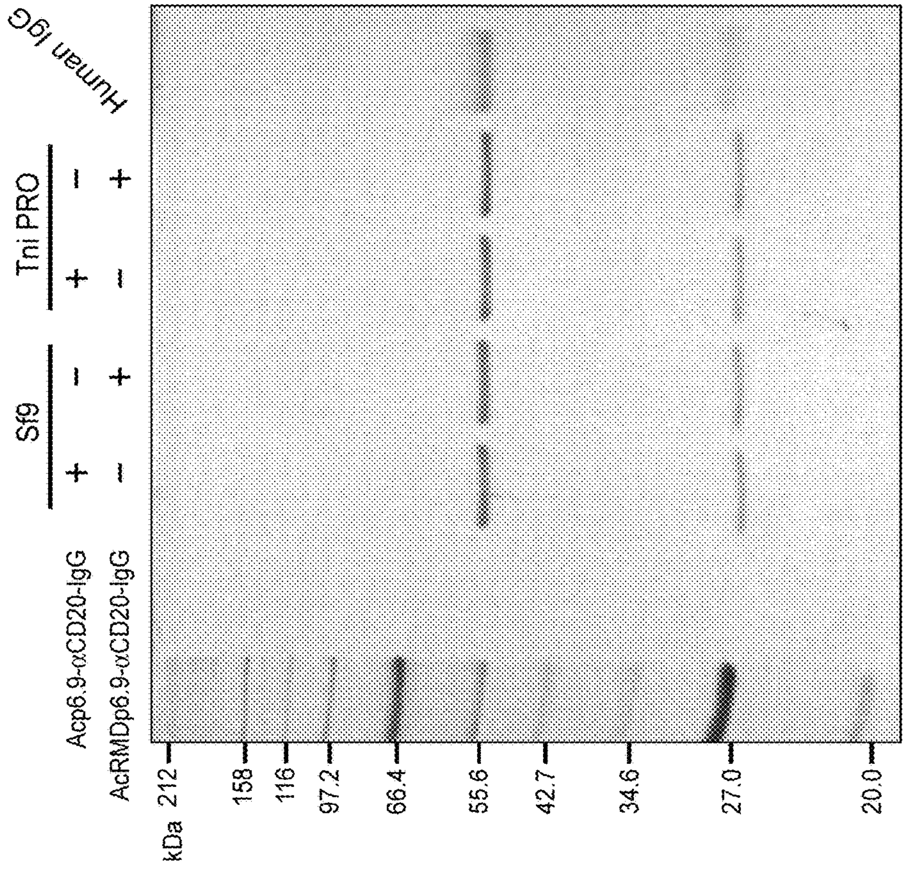

FIGS. 11A-11B. Analysis of purified anti-CD20-IgG preparations from Sf9 and Tni PRO™. The anti-CD20-IgG preparations produced by Sf9 or Tni PRO™ cells infected with Acp6.9-αCD20-IgG or AcRMDp6.9-αCD20-IgG were affinity purified using protein A, as described in Materials and methods, resolved by SDS-PAGE under reducing (FIG. 11A) or non-reducing (FIG. 11B) conditions, and stained with Coomassie Brilliant Blue.

Figure 12A:
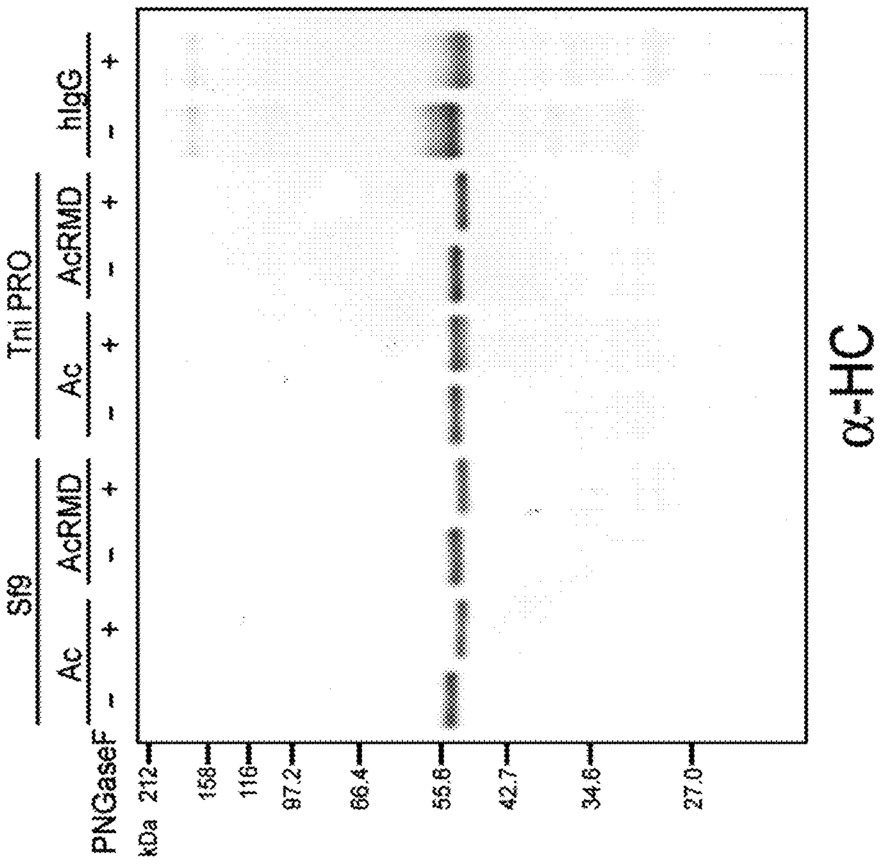
Figure 12B:
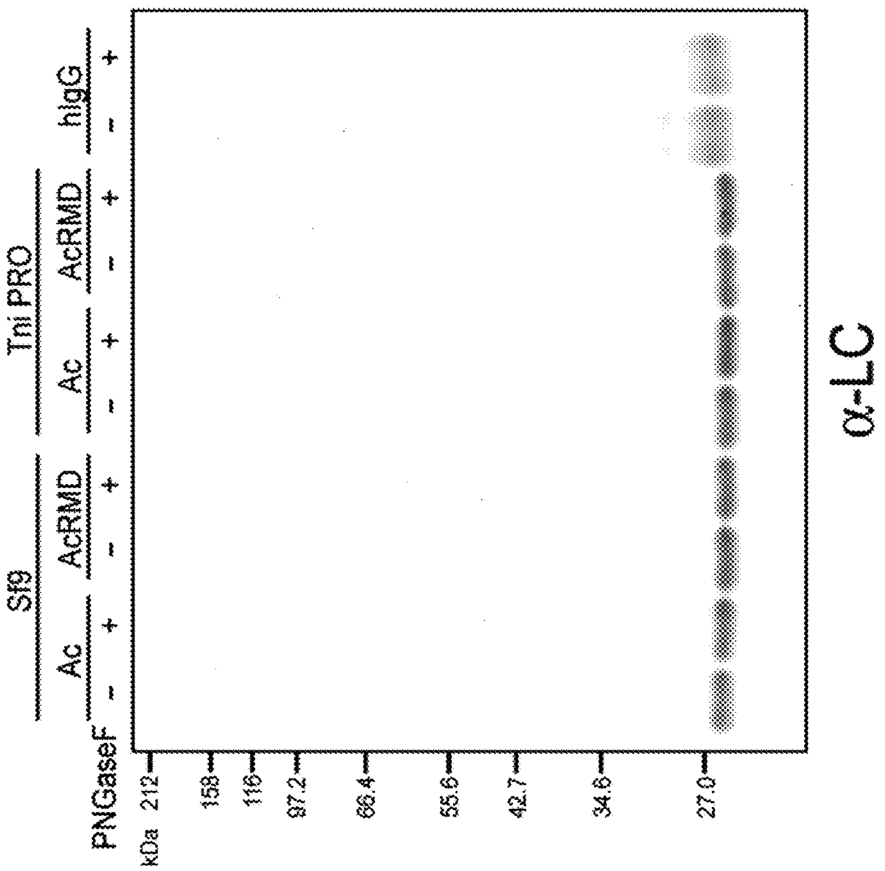
Figure 12C:
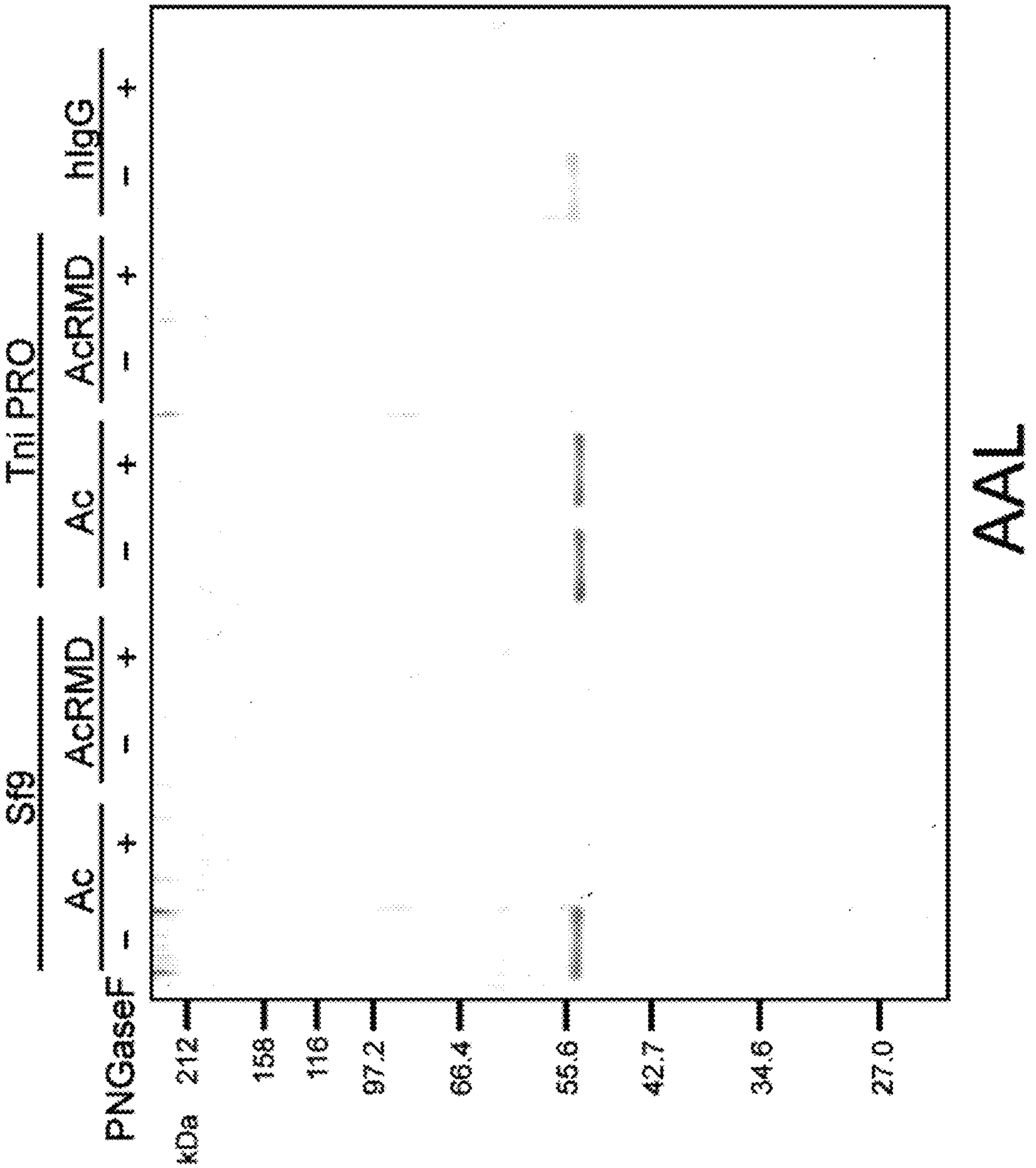

FIGS. 12A-12C. Fucosylation of an anti-CD20-IgG (rituximab) produced using baculovirus or AcRMD baculovirus vectors. Sf9 and Tni PRO™ cells were infected with either Acp6.9-αCD20-IgG or AcRMDp6.9-αCD20-IgG, and the cell-free media were harvested and used to affinity purify anti-CD20-IgG at 48 hours post-infection. The results of western blotting assays with anti-human IgG Fc (FIG. 12A, α-HC) or anti-human IgG κ chain (FIG. 12B, α-LC) and lectin blotting assays with AAL (FIG. 12C) with (+) or without (−) PNGase-F pre-treatment are shown.

Figure 13A:
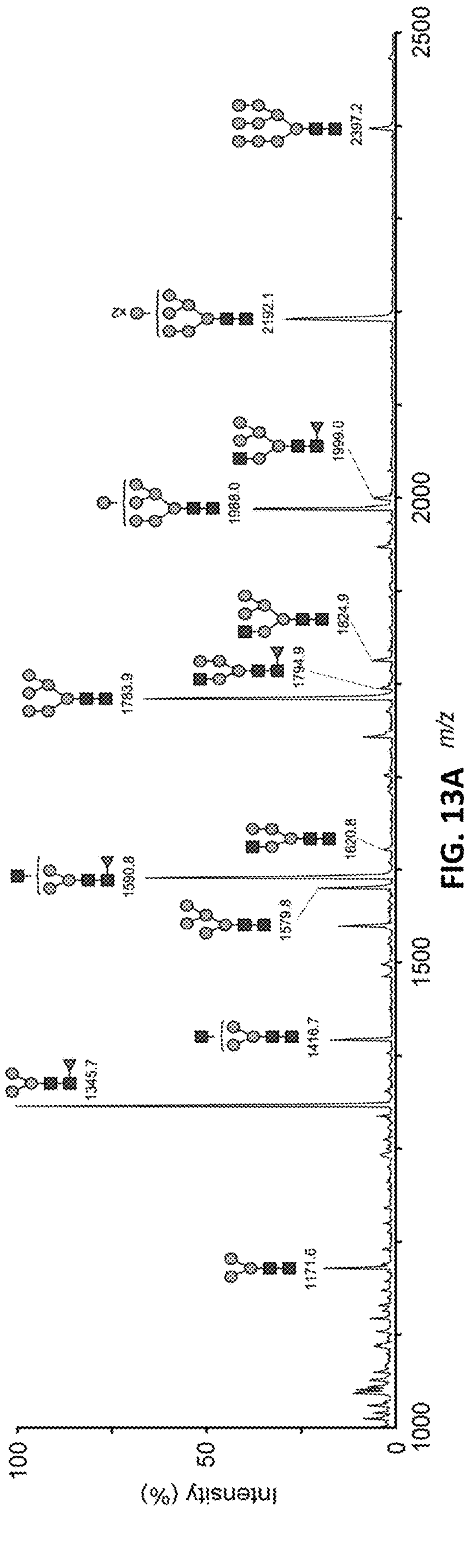
Figure 13B:
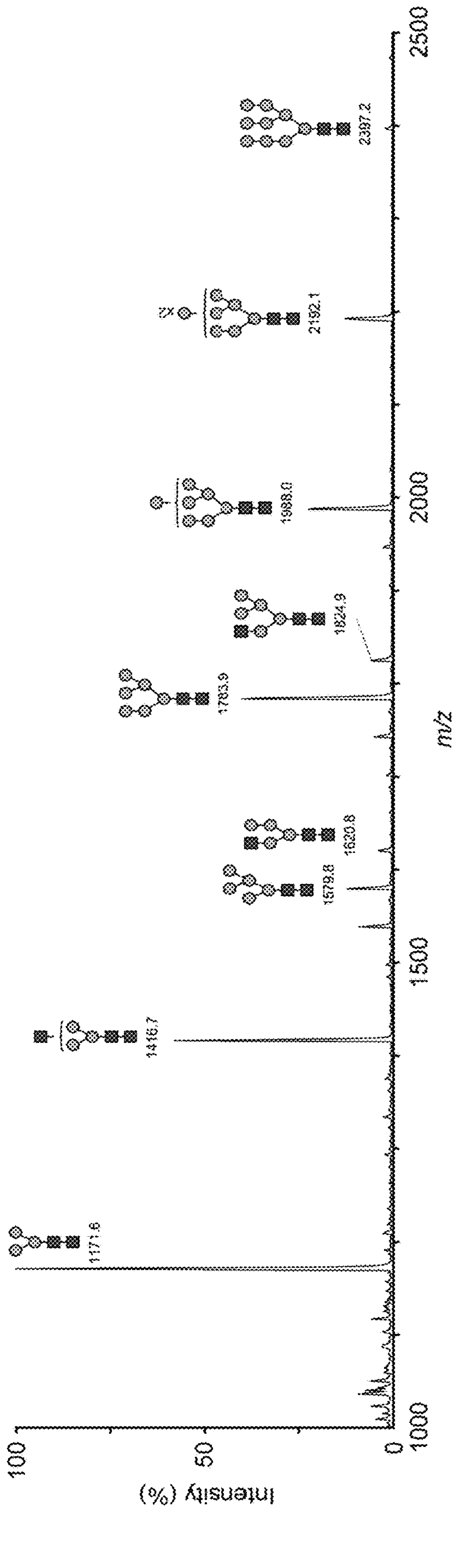
Figure 13C:
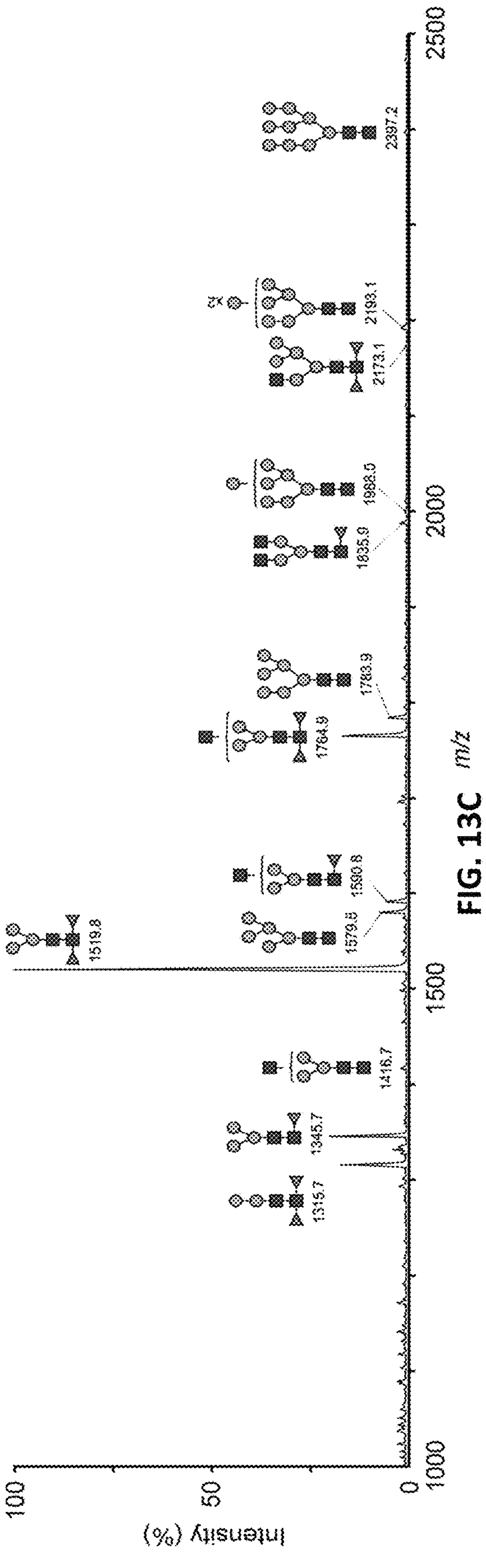
Figure 13D:
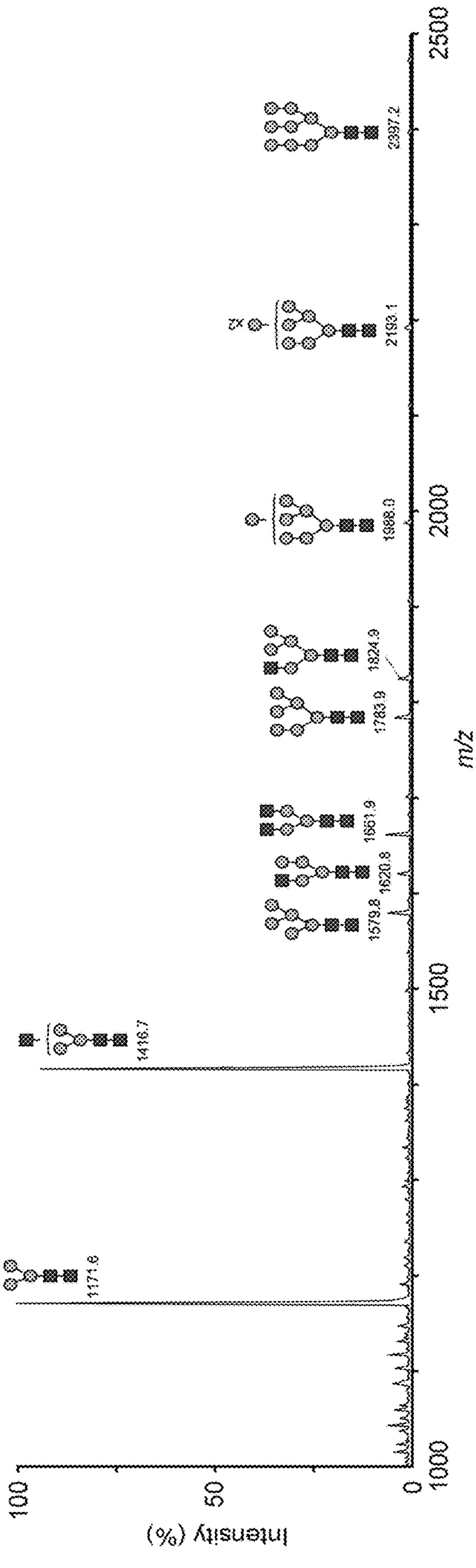
Figure 14A:
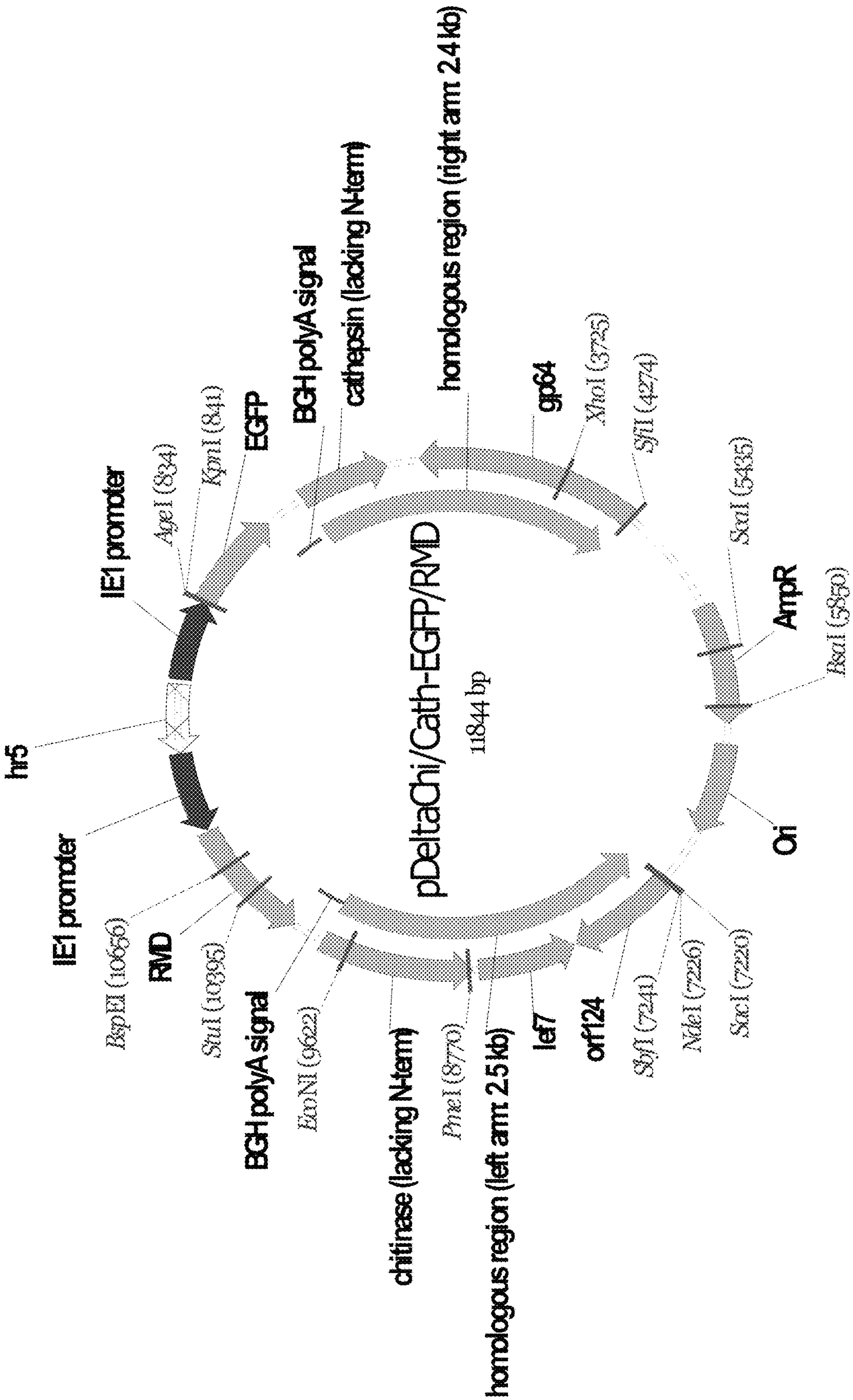

FIGS. 13A-13D. N-glycan profiling of various anti-CD20-IgG preparations by MALDI-TOF MS. Anti-CD20-IgG was isolated from Sf9 or Tni PRO™ cells infected with Acp6.9-αCD20-IgG or AcRMDp6.9-αCD20-IgG, as described in the legend of FIG. 12. The N-glycans were removed by PNGaseAr treatment, recovered, permethylated, and analyzed by MALDI-TOF MS, as described in Materials and methods. Anti-CD20-IgG from Sf9 cells infected with Acp6.9-αCD20-IgG (FIG. 13A), Sf9 cells infected with AcRMDp6.9-αCD20-IgG (FIG. 13B), Tni PRO™ cells infected with Acp6.9-αCD20-IgG (FIG. 13C), or Tni PRO™ cells infected with AcRMDp6.9-αCD20-IgG (FIG. 13D). All molecular ions were detected as $[M+Na]^+$, assigned, and annotated using the standard cartoon symbolic representations.

FIGS. 14A-14E. A plasmid map (FIG. 14A) showing the major genetic elements and text files (FIGS. 14B to 14E) of the hr5 enhancer, AcMNPV ie1 promoter, codon-optimized RMD encoding sequence and the optional EGFP encoding sequences in the transfer plasmid pΔChi/Cath-EGFP/RMD, which was used to isolate AcRMD (SEQ ID NO: 1). In certain embodiments the EGFP encoding sequences are removed from SEQ ID NO: 1.

FIGS. 15A-15D. FIGS. 15A-15D show the pVL1393-polh-antiCD20-IgG sequence containing the AcMNPV polyhedrin promoter, anti-CD20-IgG heavy chain coding sequence, and anti-CD20-IgG light chain coding sequence (SEQ ID NO: 2), which was used to isolate a daughter of AcRMD encoding anti-CD20 under the control of the polyhedrin promoter.

FIGS. 16A-16D. FIGS. 16A-16D show text files of pVL1393-p6.9-antiCD20-IgG sequence containing the AcMNPV p6.9 promoter, anti-CD20-IgG heavy chain coding sequence, and anti-CD20-IgG light chain coding sequence (SEQ ID NO: 3), which was used to isolate a daughter of AcRMD encoding anti-CD20 under the control of the p6.9 promoter.

DETAILED DESCRIPTION OF THE INVENTION

The ability to glycosylate recombinant proteins is an important attribute of insect-based, including baculovirus-insect cell expression systems, but some insect cell lines produce recombinant glycoproteins with core $\alpha 1,3$-fucosylated N-glycans, which are highly immunogenic and render products unsuitable for human use. To address this problem, we exploited a bacterial enzyme, GDP-4-dehydro-6-deoxy-D-mannose reductase (Rmd), which consumes the precursor to GDP-L-fucose. We expected this enzyme to indirectly block glycoprotein fucosylation by blocking the production of GDP-L-fucose, which is required as the donor substrate for this process. Initially, we genetically transformed two different insect cell lines to constitutively express Rmd and successfully isolated subclones with fucosylation-negative phenotypes. Surprisingly, however, we found that the fucosylation-negative phenotypes induced by Rmd expression were unstable, indicating that the prior art involving host cell engineering is ineffective in insect systems. Thus, we constructed a novel baculovirus vector designed to express Rmd immediately after infection and to facilitate the insertion of genes encoding any glycoprotein of interest for expression at a later time after infection. We used this vector to produce a daughter encoding a therapeutic anti-CD20-IgG (rituximab) and found, in contrast to an Rmd-negative control, that insect cells infected with this virus produced a non-fucosylated form of this antibody. These results indicate that the novel $Rmd^+$ baculoviral vector we produced can be used to solve the problem of immunogenic core α1,3-fucosylated N-glycan production associated with insect cell systems, including the baculovirus-insect cell system. These results extend the utility of such systems, which, when used in conjunction with existing glycoengineered insect cell lines, now include therapeutic glycoprotein production, in particular, production of recombinant antibodies lacking fucose with enhanced effector functions.

Definitions

A "cell line" refers to cells that can be cultured in the lab for an indefinite period and are useful for producing large amounts of a protein of interest.

As used herein, the term "insect" includes an insect in any stage of development, including first through fifth instar larvae. For the production of non-fucosylated polypeptides of interest, a large larva, such as a third, fourth, or fifth instar larva is preferred. It will be evident to a skilled worker which insect stage is suitable for a particular purpose, such as for direct production of a glycosylated polypeptide of interest, for storage or transport of an insect to a different location, for generation of progeny, for further genetic crosses, or the like.

With reference to nucleic acids of the invention, the term "isolated nucleic acid" is sometimes used. This term, when applied to DNA, refers to a DNA molecule that is separated from sequences with which it is immediately contiguous (in the 5' and 3' direction) in the naturally occurring genome of the organism from which it originates. For example, the "isolated nucleic acid" may comprise a DNA or cDNA molecule inserted into a vector, such as a plasmid or virus vector, or integrated into the DNA of a prokaryote or eukaryote. Isolated nucleic acids refers to those suitable for insertion in the recombinant baculoviral vectors described herein, e.g., RMD encoding nucleic acids and those encoding the desired protein of interest.

With respect to protein, the term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form.

The term "protein of interest" is sometimes used herein. The term refers to any protein and includes, without limitation, therapeutic proteins, antibodies, a subunit vaccine, an antibiotic, a cytokine, an anticoagulant, a viral antigen, an enzyme, a hormone, or a blood clotting factor.

The term "promoter region or expression control sequence" refers to the transcriptional regulatory regions of a gene, which may be found at the 5' or 3' side of the coding region, or within the coding region, or within introns. Such sequences regulate expression of a polypeptide coded for by a polynucleotide to which it is functionally ("operably") linked. Expression can be regulated at the level of the mRNA or polypeptide. Thus, the term expression control sequence includes mRNA-related elements and protein-related elements. Such elements include promoters, domains within promoters, upstream elements, enhancers, elements that confer tissue or cell specificity, response elements, ribosome binding sequences, transcriptional terminators, etc.

Suitable expression control sequences that can function in insect cells will be evident to the skilled worker. In some embodiments, the coding sequences described herein may be operably linked to an expression control sequence from the virus, itself, or to another suitable expression control sequence. Suitable baculovirus vectors include those based on *Autographa californica* NPV, *Orgyia pseudotsugata* NPV, *Lymantria dispar* NPV, *Bombyx mori* NPV, *Rachoplusia ou* NPV, *Spodoptera exigua* NPV, *Heliothis zea* NPV, *Galleria mellonella* NPV, *Anagrapha falcifera* nucleopolyhedrovirus (AfNPV), *Trichoplusia ni* singlenuclepolyhedrovirus (TnSNPV). As discussed above, baculovirus-based vectors have been generated (or can be generated without undue experimentation) that allow the cloning of large numbers of inserts, at any of a variety of cloning sites in the viral vector. Thus, more than one heterologous polypeptide may be introduced together into a transgenic insect cell or insect of the invention. The viral vector can be introduced into an insect cell or insect by known methods, such as by in vitro inoculation (insect cells) or injection or oral ingestion (insect larvae). Among the many suitable "strong" promoters that can be used are the baculovirus p10, polyhedrin (polh), p6.9, capsid, and v-cath promoters. Among the many suitable "weak" promoters are the baculovirus ie1, ie2, ie0, etl, 39K (aka pp31), and gp64 promoters. Other suitable constitutive promoters include insect actin hsp70, α1-tubulin, and ubiquitin gene promoters; RSV and MMTV promoters, copia promoter, gypsy promoter, and the cytomegalovirus IE promoter. If it is desired to increase the amount of gene expression from a weak promoter, enhancer elements, such as the baculovirus enhancer elements, hr5 or hr2, among others, may be used in conjunction with the promoter.

In some embodiments of the invention, as is discussed in more detail elsewhere herein, it is desirable that an expression control sequence is regulatable (e. g., comprises an inducible promoter and/or enhancer element). Suitable regulatable promoters include, e.g., hsp70 promoters, the *Drosophila* metallothionein promoter, an insect ecdysone-regulated promoter, the *Saccharomyces cerevisiae* Gal4/UAS system, and other well-known inducible promoter systems. A Tet-regulatable molecular switch may be used in conjunction with any constitutive promoter, such as those described elsewhere herein (e. g, in conjunction with the CMV-IE promoter, or baculovirus promoters). Another type of inducible promoter is a baculovirus delayed early, late or very late promoter that is only activated following infection by a baculovirus.

In some embodiments, the expression control sequence comprises a tissue- or organ-specific promoter. Many such expression control sequences will be evident to the skilled worker.

The term "vector" refers to a small carrier DNA molecule into which a DNA sequence can be inserted for introduction into a host cell where it will be replicated. An "expression vector" is a specialized vector that contains a gene or nucleic acid sequence with the necessary regulatory regions needed for expression in a host cell. A "baculovirus expression vector" is an expression vector consisting of a recombinant baculovirus that contains a gene or nucleic acid sequence with the necessary regulatory regions needed for expression in a host cell.

The term "operably linked" means that the regulatory sequences necessary for expression of a coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The phrase "consisting essentially of" when referring to a particular nucleotide sequence or amino acid sequence means a sequence having the properties of a given SEQ ID NO: For example, when used in reference to an amino acid sequence, the phrase includes the sequence per se and molecular modifications that would not affect the basic and novel characteristics of the sequence.

Methods for designing and preparing constructs suitable for generating recombinant baculovirus vectors for infection of insect cells or insects are known to one of ordinary skill in the art. For these methods, as well as other molecular biology procedures related to the invention, see, e. g., Sambrook et al. 1989; Wu et al. 1997; and Ausabel et al. 1994-1999.

In a preferred embodiment, the baculovirus replicates until the host insect cell is killed. The insect cell or insect lives long enough to produce large amounts of the non-fucosylated polypeptide of interest. In another embodiment, a baculovirus is used that is attenuated or non-permissive for the host. In this case, the host is not killed by replication of the baculovirus, itself (although the host may be damaged by expression of the heterologous protein of interest).

The following materials and methods are provided to facilitate the practice of the present invention.

Plasmid Constructions

The *Pseudomonas aeruginosa* Rmd (GenBank: AAG08839.1) coding sequence was optimized for *Spodoptera frugiperda*, synthesized by GeneArt® (Life Technologies, Gaithersburg, Md.), and cloned into pMK-T to produce a plasmid designated pKan-RMD.

pIE1-RMD, a plasmid designed to express Rmd under the control of the AcMNPV ie1 promoter, was constructed by subcloning the BamHI-NotI fragment of pKan-RMD into the BamHI and NotI sites of pIE1TV4 (Jarvis et al. 1996).

pAcP(+)IE1-RMD, a baculovirus transfer plasmid, was constructed by subcloning the BamHI-NotI fragment of pIE1-RMD into the BglII and NotI sites of pAcP(+)IE1TV3 (Jarvis et al. 1996).

pDIE1-EGFP/RMDΔBsu36I, a plasmid designed to express both EGFP and Rmd under the control of dual, back-to-back AcMNPV ie1 promoters, was constructed in four sequential steps. First, the bovine growth hormone (BGH) polyadenylation (poly A) signal was amplified by polymerase chain reaction (PCR) with pcDNA3.1 (Life Technologies) as the template and PmeI-BGHpolyA-Fw and SpeI-BGHpolyA-Rv as the primers. The resulting amplimer was digested with PmeI and SpeI and cloned into the corresponding sites of pIE1TV4 to produce a plasmid designated pIE1-BR. Second, the EGFP coding sequence was amplified by PCR with pIE1-EGFP as the template and BamHI/KpnI-EGFP-Fw and NruI-EGFPstop-Rv as the primers. The resulting amplimer was digested with BamHI and NruI and subcloned into the BamHI and PmeI sites of pIE1-BR to produce a plasmid designated pIE1-EGFP-BGH. Third, the Bsu36I site of Rmd was deleted by overlapping PCR mutagenesis. This involved amplifying the 5'-region of Rmd with NruI-RMD-Fw and RMD-BsuDel-Rv as the primers and the 3'-region of Rmd with RMD-BsuDel-Fw and ApaI-RMD-Rv as the primers, with pIE1-RMD as the template in both cases. The resulting 5'- and 3'-region Rmd amplimers were mixed and used as templates for an overlapping PCR with NruI-RMD-Fw and ApaI-RMD-Rv as the primers. The resulting RMDBsu36I amplimer was subcloned into pGEM-T (Promega, Madison, Wis.) to produce pDIE1-EGFP/RMDΔBsu36I. Finally, the EGFP-BGH poly A signal and RMDΔBsu36I coding sequence were assembled by sequentially subcloning the KpnI-HindIII fragment of pIE1-EGFP-BGH and the NruI-ApaI fragment of pGEMT-RMDΔBsu36I into the corresponding sites of pDIE1-TOPO.3 (Shi et al. 2007) to produce the plasmid designated pDIE1-EGFP/RMDΔBsu36I.

To construct a baculovirus transfer vector targeting the chiA/v-cath locus, we produced three PCR amplimers comprised of AcMNPV orf124/lef7, chiA, or v-cath/gp64 sequences and independently subcloned each one into pGEM-T. After verifying their sequences, these three DNA fragments were assembled by sequentially subcloning the PmeI-ApaI fragment of chiA and then the ApaI fragment of v-cath/gp64 into the corresponding sites of pGEMT-orf124/lef7 to produce a new plasmid designated pChi/CathTVC6. Finally, we blunt-ended the HindIII-BamHI fragment of pDIE1-EGFP/RMDΔBsu36I with T4 DNA polymerase (New England Biolabs, Beverly, Mass.) and inserted the resulting DNA fragment into the T4 DNA polymerase blunt-ended HindIII and EcoRI sites of pChi/CathTVC6. This transfer plasmid, which was designated pΔChi/Cath-EGFP/RMDΔBsu36I, was used to create the new baculovirus vector in which the viral chiA and v-cath genes were replaced by genes encoding Rmd and EGFP, each under the control of the AcMNPV ie1 promoter.

pVL1393-polh-αCD20-IgG and pVL1393-p6.9-αCD20-IgG, which are baculovirus transfer plasmids used to isolate baculovirus expression vectors encoding anti-CD20-IgG, were constructed in four sequential steps. First, the BGH poly A signal was PCR amplified with pIE1-BR as the template and EcoRI-BGHpolyA-Fw and EcoRV-BGH-polyA-Rv as the primers. The resulting amplimer was digested with EcoRI and EcoRV and then subcloned into the corresponding sites of pVL1393 (Summers and Smith 1987) to produce pVL1393-BGH. Second, the NotI-SbfI fragment of pGEMT-αCD20HC, which encodes the heavy chain, and the NotI-EcoRI fragment of pGEMT-αCD20LC, which encodes the light chain of anti-CD20-IgG were sequentially subcloned into the NotI-PstI and NotI-EcoRI sites of pVL1393-BGH to produce pVL1393-αCD20-IgG-no promoter. Third, two copies of the AcMNPV polyhedrin or p6.9 promoter were assembled in back-to-back orientation, with the second intron of the *Drosophila melanogaster* white gene as an intervening spacer, to create plasmids designated either pGEMT-ppol-wi-ppol or pGEMT-p6.9-wi-p6.9, respectively. The former was constructed by PCR-amplifying two copies of the polyhedrin promoter with pAcGT N-term 8×His pPol (Toth et al. 2011) as the template and either NheI-ppol-Fw and NotI-ppol-Rv or XhoI-ppol-Fw and SphI/PmeI-ppol-Rv as the primers. The resulting amplimers were digested with NheI and NotI or XhoI and SphI, respectively, and sequentially subcloned into the corresponding sites of pGEM-WIZ (Bao and Cagan 2006). Similarly, pGEMT-p6.9-wi-p6.9 was constructed by PCR-amplifying two copies of the p6.9 promoter with pAcp6.9GT N-term 8×His pPol (Toth et al. 2011) as the template and either NheI-p6.9-Fw and NotI-p6.9-Rv or XhoI-p6.9-Fw and SphI/PmeI-p6.9-Rv as the primers. The resulting amplimers were digested with NheI and NotI or XhoI and SphI, respectively, and sequentially subcloned into the corresponding sites of pGEM-WIZ. Finally, each back-to-back promoter cassette was independently subcloned into the anti-CD20-IgG baculovirus transfer plasmid described above. pVL1393-polh-αCD20-IgG was constructed by subcloning the PmeI-NotI fragment of pGEMT-ppol-wi-ppol and pVL1393-p6.9-αCD20-IgG was constructed by subcloning the PmeI-NotI fragment of pGEMT-p6.9-wi-p6.9 into the corresponding sites of pVL1393-αCD20-IgG_no promoter, respectively.

Phusion® Taq DNA polymerase (New England Biolabs) and a Biometra TProfessional Standard Thermocycler (Gottingen, Germany) were used for all PCRs and all primer sequences are given in Table 1.

TABLE 1

Primers used in this study.

| Primer name | Sequence (5' to 3') |
|---|---|
| PmeI-BGHpolyA-Fw | Gtttaaacgcctcgactgtgccttctagttg (SEQ ID NO: 4) |
| SpeI-BGHpolyA-Rv | Actagttccccagcatgcctgctatt (SEQ ID NO: 5) |
| BamHI/KpnI-EGFP-Fw | Aatggatccggtaccaccatggtgagcaagggcg (SEQ ID NO: 6) |
| NruI-EGFPstop-Rv | Ggcacttcgcgattacttgtacagctcgtccatgcc (SEQ ID NO: 7) |
| NruI-RMD-Fw | Ttatctcgcgaaccatgactcaacgcttgttcg (SEQ ID NO: 8) |
| RMD-BsuDel-Rv | Atcacggaatgcctcgggtacgtatg (SEQ ID NO: 9) |
| RMD-BsuDel-Fw | Gctggtcaaacatacgtacccgaggc (SEQ ID NO: 10) |
| ApaI-RMD-Rv | Tgggcccttactcctctctaacacgagattccca (SEQ ID NO: 11) |
| EcoRI-BGHpolyA-Fw | Attgtgaattcgcctcgactgtgccttctagttgc (SEQ ID NO: 12) |
| EcoRV-BGHpolyA-Rv | Taattgatatctccccagcatgcctgctattg (SEQ ID NO: 13) |
| NheI-ppol-Fw | Gccgcgctagcatcatggagataattaaaatgataaccatctcgcaaataa (SEQ ID NO: 14) |
| NotI-ppol-Rv | Aatttgcggccgcagcgcccgatggtgggacg (SEQ ID NO: 15) |
| XhoI-ppol-Fw | Gggcctcgagatcatggagataattaaaatgataaccatctcgcaaataa (SEQ ID NO: 16) |
| SphI/PmeI-ppol-Rv | Atttgcatgcgtttaaacagcgcccgatggtgggacg (SEQ ID NO: 17) |
| NheI-p6.9-Fw | Gccgcgctagcaaattccgttttgcgacgatg (SEQ ID NO: 18) |

TABLE 1-continued

| Primers used in this study. | |
|---|---|
| Primer name | Sequence (5' to 3') |
| NotI-p6.9-Rv | Aatttgcggccgcgtttaaattgtgtaatttatgtagctgtaatttttacc (SEQ ID NO: 19) |
| XhoI-p6.9-Fw | Gggcctcgagaaattccgttttgcgacgatg (SEQ ID NO: 20) |
| SphI/PmeI-p6.9-Rv | Atttgcatgcgtttaaacgtttaaattgtgtaatttatgtagctgtaatttttacc (SEQ ID NO: 21) |
| orf124-Fw | Atttgtatttaatcaatcgaaccgtgcac (SEQ ID NO: 22) |
| RMD-Rv | Gattgggaatctcgtgttagagaggagtaa (SEQ ID NO: 23) |
| EGFP-Fw | Atcttcttcaaggacgacggcaac (SEQ ID NO: 24) |
| gp64-Rv | Agcaagatggtaagcgctattgttttatatgtgc (SEQ ID NO: 25) |
| chi-Fw | Agatgggtatgaaaccatacaacaagtgtg (SEQ ID NO: 26) |
| cath-Rv | Cgctaccataatctttgttgaatcgatg (SEQ ID NO: 27) |

Cells and Viruses

Sf9 and Tni PRO™ (Expression Systems, Woodland, Calif.) cells were routinely maintained as shake-flask cultures in ESF 921 medium (Expression Systems) at 28° C. High Five™ cells (Life Technologies) were maintained as adherent cultures in TNM-FH medium containing 10% (v/v) fetal bovine serum (Atlanta Biologics, Atlanta, Ga.).

SfRMD is a transgenic Sf9 cell derivative that was produced for this study using a modification of an established procedure (Harrison and Jarvis, 2007). Briefly, Sf9 cells were co-transfected with a mixture of pIE1-Neo (Jarvis et al. 1990) and pIE1-RMD using a modified calcium phosphate method (Summers and Smith 1987). The transfected cells were allowed to recover for 1 day, treated with 1 mg of G418 (Life Technologies)/mL of TNM-FH medium containing 10% (v/v) fetal bovine serum (Atlanta Biologics) for 1 week, and G418-resistant clones were isolated by limiting dilution, as described previously (Hollister and Jarvis 2001). After stepwise amplification into larger cultures, individual clones were assayed by cell surface staining with a fucose-specific lectin, as described below. Unstained clones were designated SfRMD, characterized in more detail, and used for downstream experiments, as described below.

TnRMD is a transgenic High Five™ cell derivative that was designed to constitutively express the Rmd gene and produced for this study as described above for SfRMD. The baculovirus expression vector designated AcmIgG2a-Fc has been described previously (Geisler and Jarvis 2012).

The baculovirus expression vector designated AcP(+)IE1-RMD was isolated by co-transfecting Sf9 cells with a mixture of pAcP(+)IE1-RMD and BacPAK6 (Kitts and Possee 1993) baculoviral DNA after pre-linearizing the latter by digestion with Bsu36I. Viral progeny were harvested, clones were resolved by plaque assay in the presence of X-Gal (Sigma-Aldrich; St. Louis, Mo.), and an isolated clone with a white plaque phenotype was amplified and titered in Sf9 cells.

Baculovirus expression vectors designated Ac-αCD20-IgG and Acp6.9-αCD20-IgG were isolated by co-transfecting Sf9 cells with mixtures of either pVL1393-polh-αCD20-IgG or pVL1393-p6.9-αCD20-IgG and AcGT baculoviral DNA (Toth et al. 2011) after pre-linearizing the latter by digestion with Bsu36I. The transfected cells were cultured for 5 days in growth medium containing 100 μM ganciclovir (Life Technologies) and then viral progeny were harvested, clones were resolved by plaque assay, and an isolated clone with a white plaque phenotype was amplified and titered in Sf9 cells, as described above.

The baculovirus expression vector designated AcRMD was isolated by co-transfecting Sf9 cells with a mixture of pΔChi/Cath-EGFP/RMDΔBsu36I and BacPAK6 (Kitts and Possee 1993) baculoviral DNA (FIG. 14). This recombination strategy was custom-designed to replace the AcMNPV chiA and v-cath coding sequences with Rmd and EGFP coding sequences placed under the control of dual AcMNPV ie1 promoters separated by the AcMNPV hr5 enhancer. Viral progeny were harvested, clones were resolved by plaque assay, and fluorescent plaques were identified using an Axiovert 25 microscope equipped with HBO 50 epi-fluorescence unit (Carl Zeiss, Oberkochen, Germany). Several plaques were picked, screened by PCR, as described below, and those that included viral progeny with the Rmd and EGFP genes in the correct genomic location were used for a second round of plaque purification. The PCR screen was repeated, promising clones were used for a third round of plaque purification, and well-isolated clones with fluorescent plaque phenotypes were picked and amplified in Sf9 cells. A Wizard genomic DNA purification kit (Promega) was used to extract total DNA from Sf9 cells infected with each of those viral clones and used as the templates for final PCR analyses, which were the same as those performed for the prior screening steps. In each case, we performed PCRs with two different primer pairs, orf124-Fw and RMD-Rv or EGFP-Fw and gp64-Rv to determine if the final AcRMD isolates had the EGFP/RMDΔBsu36I expression cassette in the correct genomic location, that is, in place of the viral chiA and v-cath genes. In addition, we used a third primer pair, chi-Fw and cath-Rv, to directly confirm the absence of those viral genes and show that the final AcRMD isolates were not detectably contaminated with parental BacPAK6 vector DNA. Three clones were positive with the first two primer pairs and negative with the third and one clone was designated AcRMD, further amplified in Sf9 cells, and used for the remainder of this study.

Baculovirus expression vectors designated AcRMD-αCD20-IgG and AcRMDp6.9-αCD20-IgG (FIGS. 15 and 16) were isolated by co-transfecting Sf9 cells with a mixture of pVL1393-polh-αCD20-IgG or pVL1393-p6.9-αCD20-IgG and AcRMD baculoviral DNA pre-linearized by digestion with Bsu36I. Viral progeny were harvested, clones were resolved by plaque assay, and an isolated clone with a white plaque phenotype was amplified and titered in Sf9 cells, as described above.

Cell Surface Lectin Staining

Sf9, SfRMD, High Five™, or TnRMD cells were stained with a mixture of biotinylated AAL (Vector Labs, Burlingame, Calif.) and fluorescein-conjugated streptavidin (Vector Labs) in lectin staining buffer (10 mM Hepes, pH 7.5, 50 mM NaCl, 1 mM $CaCal_2$, 1 mM $MgCl_2$, 1 mM $MnCl_2$) for 10 min at room temperature. The cells were then washed twice with lectin staining buffer and imaged using an Olympus FSX 100 fluorescence microscope (Tokyo, Japan).

Recombinant Protein Expression and Purification

For small scale recombinant protein expression experiments, Sf9 cells were seeded at a density of $2\times10^6$ cells/well into 6-well plates and infected with Ac-αCD20-IgG, Acp6.9-αCD20-IgG, AcRMD-αCD20-IgG, or AcRMDp6.9-αCD20-IgG at a multiplicity of about 2 plaque forming units/cell. The virus was allowed to adsorb for 1 hour and then the infected cells were washed once with 1 mL of ESF 921 and cultured in 1 mL of fresh ESF 921 at 28° C. to 48 hours post-infection. At that time, the cell-free media were prepared by low speed centrifugation and used as the extracellular fractions for downstream analysis. The cell pellets were washed once with phosphate buffered saline, lysed with 1 mL of extraction buffer (20 mM HEPES, pH 7.4, 0.15 M NaCl, 0.1 mM EDTA, 0.5% Nonidet P-40), clarified by centrifugation at 13,000 rpm for 10 min, and the supernatants were used as the intracellular fractions for downstream analysis.

For larger scale recombinant protein expression and purification, Sf9, Tni PRO™, or High Five™ cells were seeded into 50 mL shake flask cultures at a density of $2\times10^6$ cells/mL in ESF 921 and then infected with Acp6.9-αCD20-IgG, AcRMDp6.9-αCD20-IgG, AcmIgG2a-Fc, or a mixture of AcmIgG2a-Fc and AcP(+)IE1-RMD using a multiplicity of about 2 plaque forming units/cell for each virus. After a 1 hour adsorption period, the infected cells were gently pelleted, resuspended in 50 mL of fresh ESF 921 supplemented with antibiotics (1.25 μg/mL amphotericin B and 25 μg/mL gentamicin), returned to the shake flasks, and incubated at 28° C. to 48 hours post-infection. Cells and debris were pelleted by centrifugation at 1,000×g for 10 min at 4° C., the supernatants were harvested, and budded baculovirus progeny were removed by centrifugation at 70,000×g for 30 min at 4° C. One Complete Protease Inhibitor Cocktail tablet (Roche Diagnostics, Indianapolis, Ind.) was dissolved in each final supernatant and then each was transferred into a 12-14,000 molecular weight cut-off membrane (Spectrum Labs, Rancho-Dominguez, Calif.) and dialyzed against 0.1 M NaCl for 6 hours. Each anti-CD20-IgG or mIgG2a-Fc preparation was subsequently dialyzed against 0.15 M or 0.5 M NaCl, respectively, and then each was purified by was affinity-purified Protein A agarose (GenScript, Piscataway, N.J.) or ProBond nickel (Life Technologies) affinity chromatography, respectively, according to the manufacturer's instructions. Eluted fractions containing the purified proteins were pooled and desalted on PD10 columns (GE Healthcare) equilibrated with phosphate buffered saline.

SDS-PAGE, Western Blotting, and Lectin Blotting Analyses

Several different types of samples were isolated from Sf9, Tni PRO™, and/or High Five™ cells and used for SDS-PAGE, western blotting, and/or lectin blotting analysis. These included intracellular fractions from uninfected cells, extracellular fractions from cells infected with various recombinant baculoviruses, and anti-CD20-IgG or mIgG2a-Fc purified from cells infected with various recombinant baculoviruses, as described above. In some cases, the samples were pre-treated with PNGase-F in reaction buffer (New England Biolabs) or PNGase-F reaction buffer alone according to the manufacturer's instructions, as described in the Figure legends. All samples were boiled in Laemmli sample buffer and then proteins were resolved by SDS-PAGE on 12% polyacrylamide gels and either stained with Coomassie Brilliant blue, destained, and imaged or electrophoretically transferred to Immobilon-P membranes (Millipore). The latter were blocked for 1 hour at room temperature with Tris-buffered saline (150 mM NaCl in 50 mM Tris-HCl, pH 7.5) containing either 5% bovine serum albumin (w/v; Sigma-Aldrich) and 0.5% (v/v) Tween 20 (Sigma-Aldrich) or 1% Tween 20 for western or lectin blotting assays, respectively. After blocking, western blotting assays were completed using alkaline phosphatase-conjugated goat anti-human IgG κ chain (Sigma-Aldrich) to detect the anti-CD20-IgG light chain, alkaline phosphatase-conjugated goat anti-human IgG Fc (Sigma-Aldrich) to detect the anti-CD20-IgG heavy chain, alkaline phosphatase-conjugated goat anti-mouse IgG to detect mIgG2a-Fc, or rabbit anti-HRP IgG (Gentaur, Brussels, Belgium) as the primary and alkaline phosphatase-conjugated goat anti-rabbit IgG (Sigma-Aldrich) as the secondary antibody to detect core α1,3-liked fucose. The lectin blotting assays were completed using alkaline phosphatase-conjugated AAL (Vector Laboratories) and the probes used for all western and lectin blotting assays were detected using a standard chromogenic assay for alkaline phosphatase activity (Blake et al. 1984).

Mass Spectrometry

N-glycans were enzymatically released from various purified mIgG2a-Fc and anti-CD20-IgG preparations by exhaustive digestion with PNGaseAr (New England Biolabs). The spent reactions were applied to pre-conditioned C18 SepPak cartridges (Waters Corp., Milford, Mass.) and the flow-through and a 5% (v/v) aqueous acetic acid wash were pooled, evaporated, and permethylated, as described previously (Dell et al. 1994). The permethylated N-glycan derivatives were extracted into chloroform, pooled with several aqueous washes, re-evaporated, and then resuspended in acetonitrile, mixed 1:1 with 2,5-dihydroxybenzoic acid matrix (10 mg/mL in 50% aqueous acetonitrile), and samples were spotted onto the MALDI-TOF target plate. Data acquisition was performed manually on a Model 4700 Proteomics Analyzer equipped with an Nd:YAG laser (Applied Biosystems, Framingham, Mass.) and 1,000 shots were accumulated in the reflectron positive ion mode.

The following example is provided to illustrate certain embodiments of the invention. It is not intended to limit the invention in any way.

Example I

A Novel Baculovirus Vector for the Production of Non-Fucosylated Recombinant Glycoproteins in Insect Cells

Analysis of Core α1,3-Fucosylation in Three Insect Cell Lines

Figure 2A:
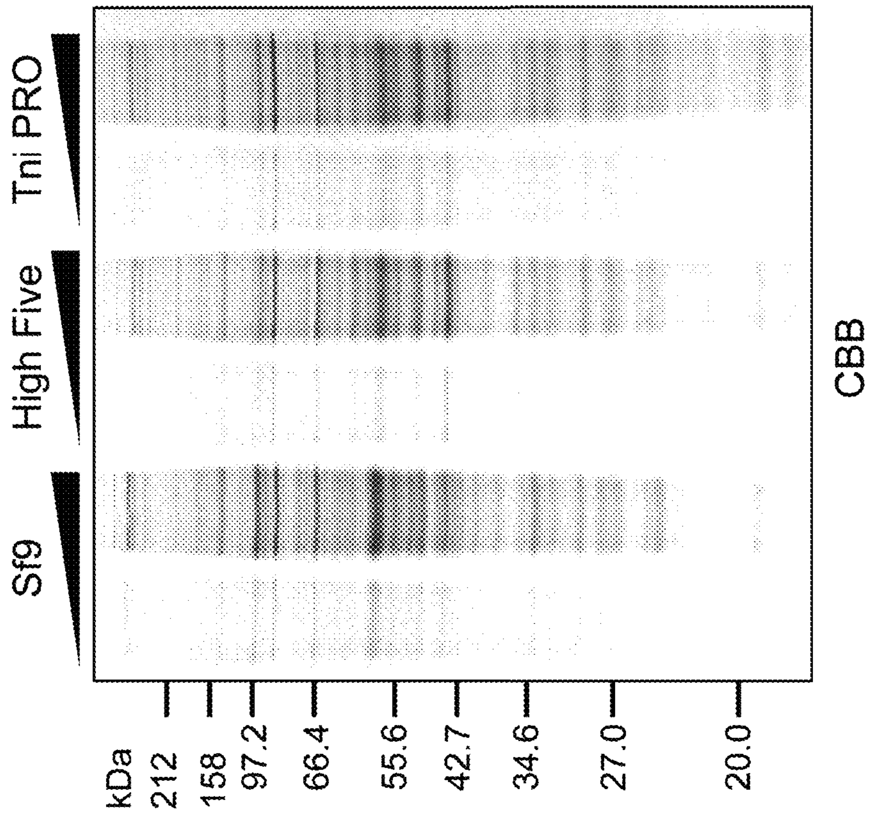
FIGS. 2A-2B. Core α1,3-fucosylation of endogenous insect cell glycoproteins. Total proteins in Sf9, High Five™, or Tni PRO™ cell lysates were resolved by SDS-PAGE in 12% acrylamide gels and stained with Coomassie Brilliant Blue (FIG. 2A) or transferred to a PVDF membrane and analyzed by western blotting with primary anti-HRP rabbit IgG and secondary α-rabbit IgG conjugated to alkaline phosphatase (FIG. 2B).
Figure 2B:
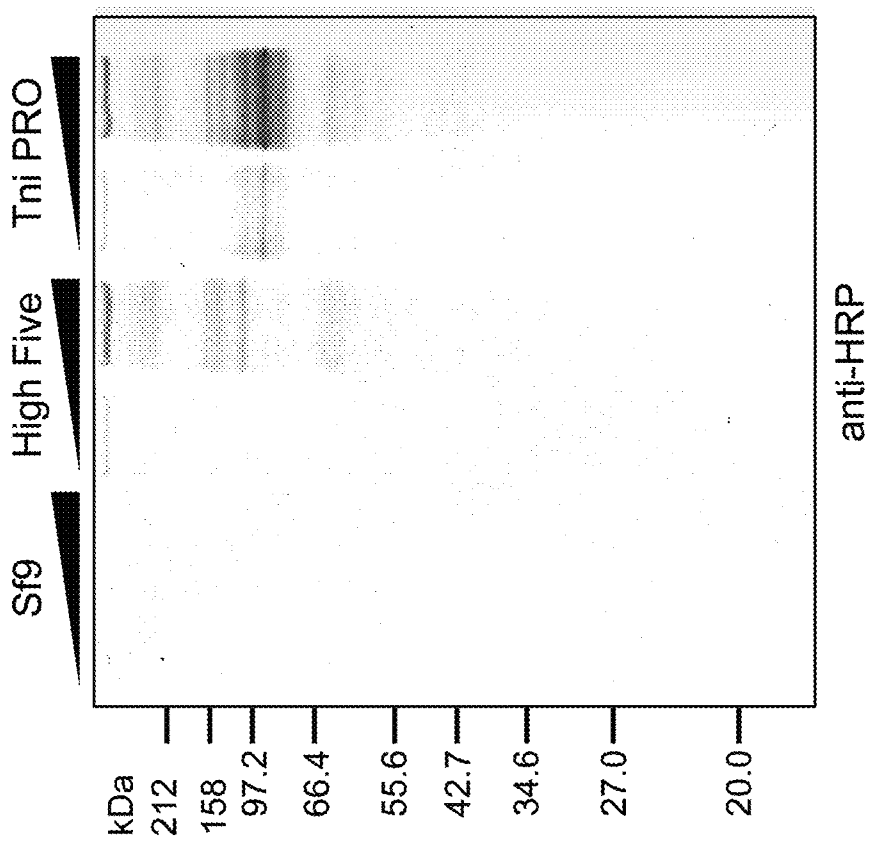

High Five™ cells, derived from *Trichoplusia ni*, but not Sf9 cells, derived from *Spodoptera frugiperda*, produce core α1,3-fucosylated glycoproteins (Rudd et al. 2000; Seismann et al. 2010; Blank et al. 2011; Palmberger et al. 2011). Another *Trichoplusia ni* cell line used as a host for baculovirus expression vectors is Tni PRO™ (Kwon et al. 2009; Bourhis et al. 2010; Bongiovanni et al. 2012; He et al. 2013; Merchant et al. 2013), but its capacity for core α1,3-fucosylation has not been reported. Thus, we analyzed intracellular extracts of uninfected Tni PRO™ cells by western blotting with anti-horseradish peroxidase (HRP), which detects core α1,3-linked fucosylation, using extracts from Sf9 and High Five™ cells as negative and positive controls. Coomassie brilliant blue staining showed that approximately equal amounts of protein were loaded in each case (FIG. 2A). The anti-HRP antibody did not detectably react with the Sf9 lysates, but reacted with several glycoproteins in the High Five™ lysates, as expected (FIG. 2B). In addition, this antibody reacted with several glycoproteins in the Tni PRO™ lysates (FIG. 2B), indicating that Tni PRO™ cells produce the immunogenic core α1,3-fucosylated sugar epitope at levels roughly comparable to High Five™ cells. These results show that it will be necessary to block core α1,3-fucosylation in both of these cell lines before we can exploit their potentially higher capacity for recombinant glycoprotein production (Davis et al. 1992; Krammer et al. 2010).

Glycoengineering Insect Cells to Block Glycoprotein Fucosylation

Figure 1B:
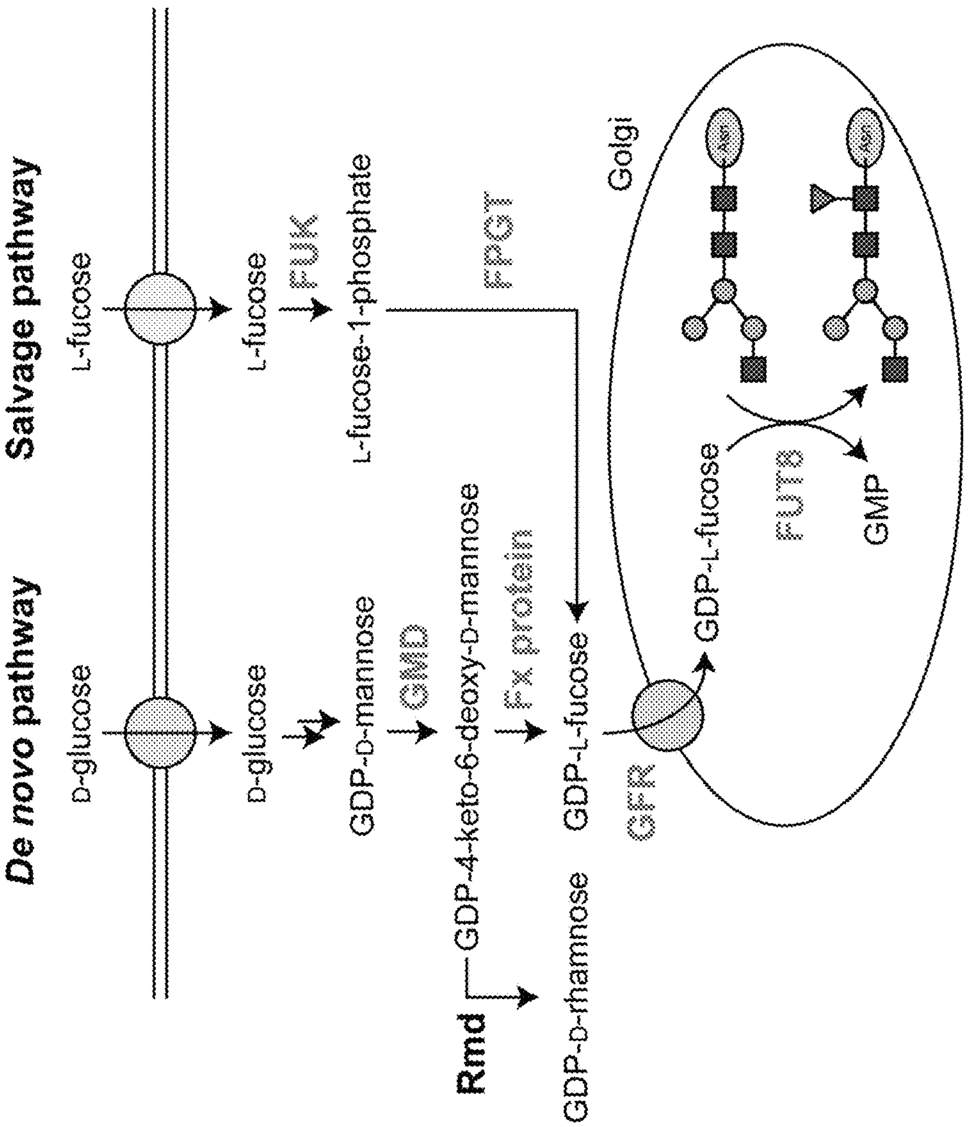
FIG. 1A-1B. Pathways of N-glycan fucosylation (FIG. 1A) and GDP-L-fucose biosynthesis (FIG. 1B). In theory, GDP-L-fucose biosynthesis in eukaryotic cells can be blocked by expression of bacterial RMD, which converts GDP-4-keto-6-deoxy-D-mannose to GDP-D-rhamnose. Abbreviations: FUT8, human core α1,6-fucosyltransferase 8; FucT6, insect core α1,6-fucosyltransferase; FucTA, insect core α1,3-fucosyltransferase; GMD, GDP-D-mannose 4,6-dehydratase; Fx protein, GDP-4-keto-6-deoxy-D-mannose 3,5-epimerase/4-reductase; GFR, Golgi GDP-L-fucose transporter; Rmd, GDP-4-dehydro-6-deoxy-D-mannose reductase; FUK, fucokinase; FPGT, fucose-1-phosphate guanylyltransferase.
Figure 1A:
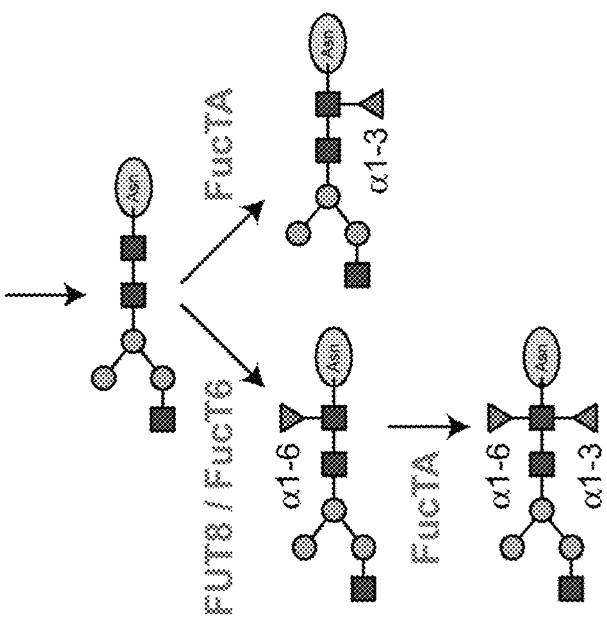
Figure 3A:
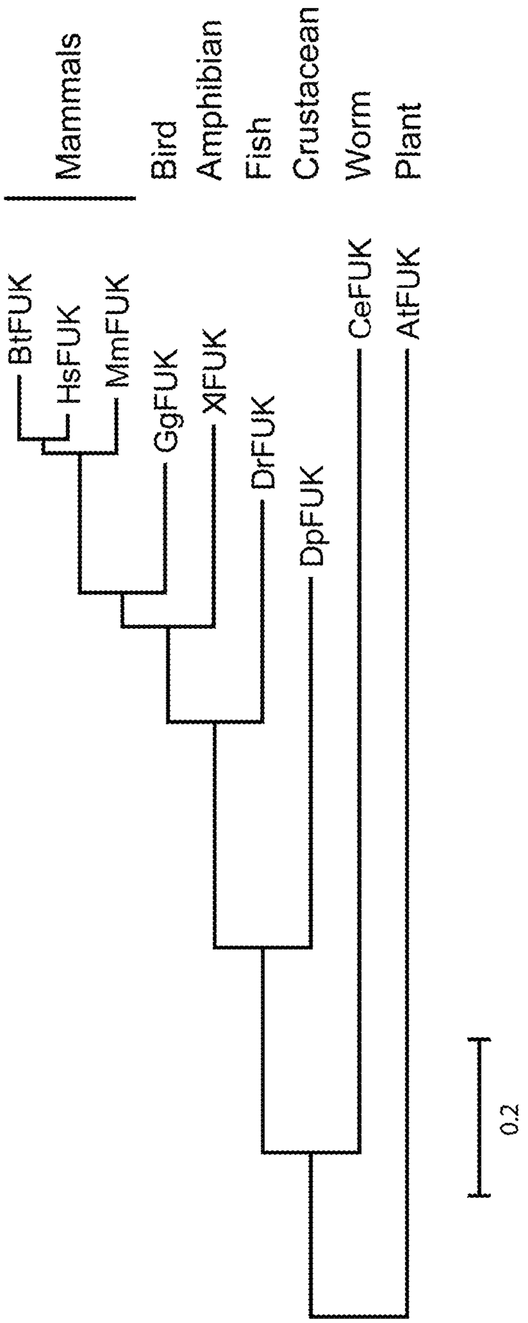
FIGS. 3A-3D. Phylogenetic trees of genes involved in GDP-L-fucose biosynthesis. Phylogenetic analysis of FUK (FIG. 3A), FPGT (FIG. 3B), GMD (FIG. 3C), and Fx protein (FIG. 3D) genes was performed using the Maximum Likelihood method with MEGA5 software (Tamura et al., 2011).
Figure 3B:
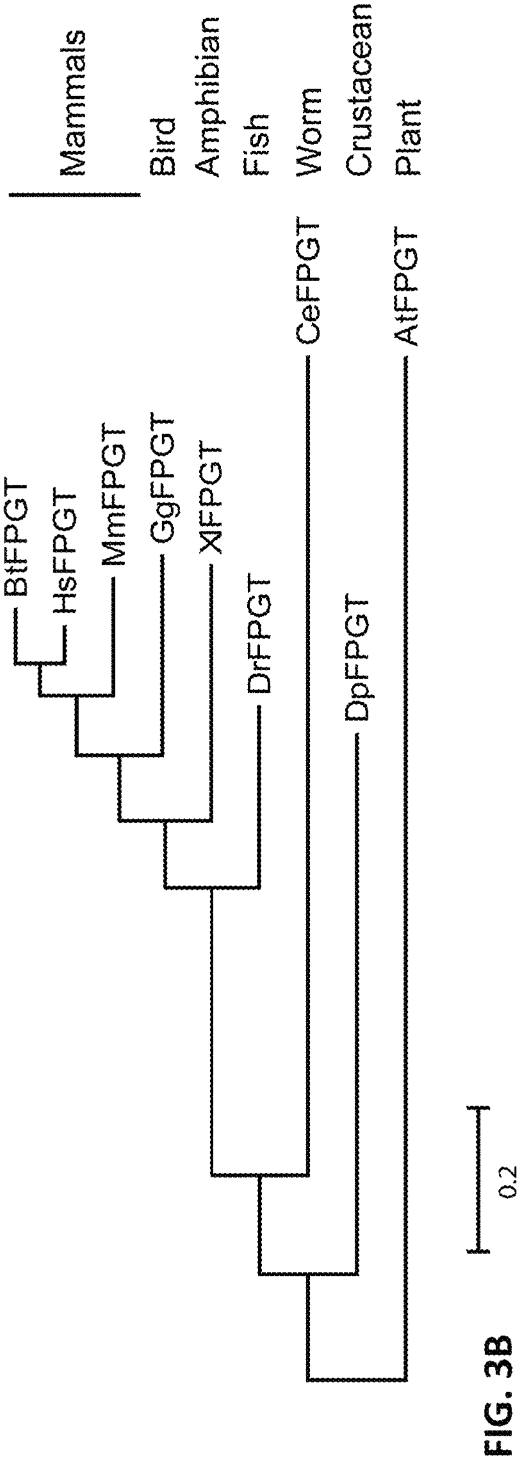
Figure 3C:
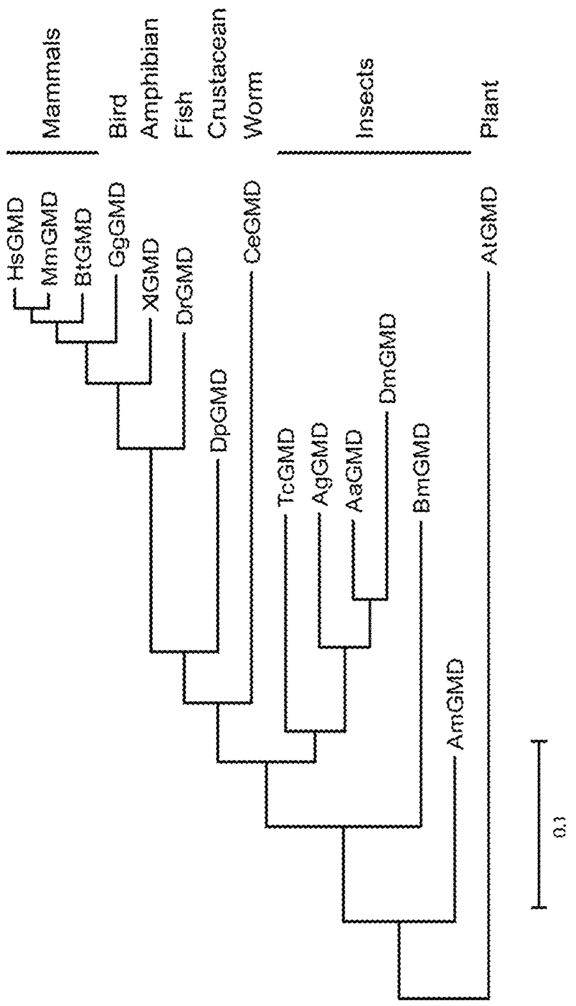
Figure 3D:
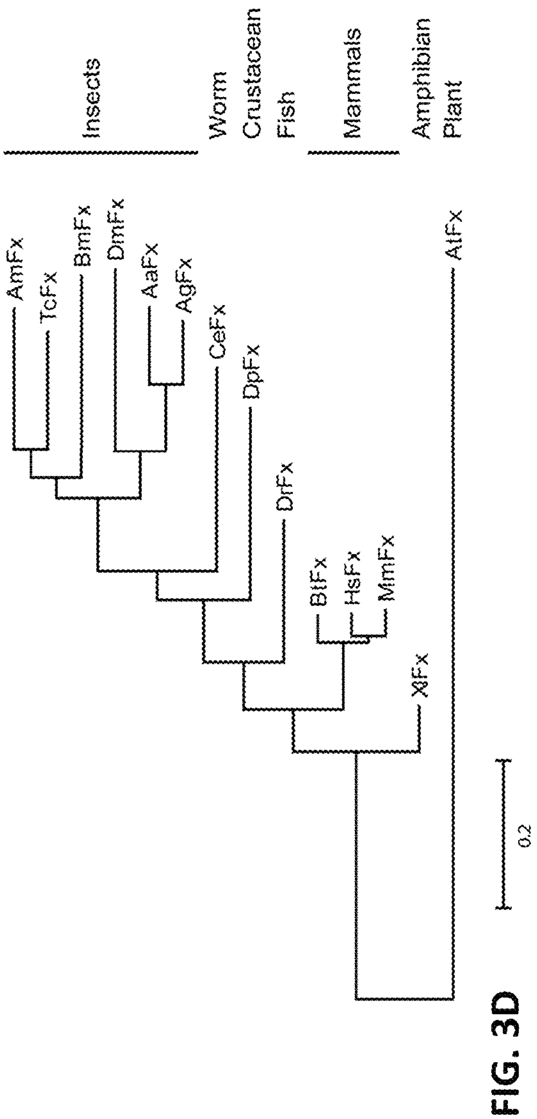

Our plan to block glycoprotein fucosylation in insect cell lines focused on blocking the biosynthesis of GDP-L-fucose, which is the donor substrate required for this process. This was a particularly attractive approach in our system because insects appeared to be the only multicellular organisms lacking two enzymes, FUK and FPGT, required for the GDP-L-fucose salvage pathway in other organisms (FIG. 1B). We drew this conclusion from a previous study indicating there are no FUK and FPGT orthologs in the *Drosophila melanogaster* genome, which was the only insect genome sequenced at that time (Rhomberg et al. 2006). However, because we now have more information from silkworm, honeybee, and mosquito genome sequencing projects, among others, we also searched the NCBI database using mammalian FUK and/or FPGT genes as queries. We identified putative orthologs in some invertebrates, including arthropods and nematodes, but none in any insects (FIG. 3A-3B). In contrast, using genes required for de novo GDP-L-fucose synthesis as queries, we found putative orthologs in a wide variety of insects, as expected (FIG. 3C-3D). Although we could not exclude the possibility that insects have an unknown salvage pathway, these results strengthened the idea that we could effectively block GDP-L-fucose biosynthesis by blocking the de novo biosynthetic pathway, alone, in insect cell lines.

In principle, we might have achieved this goal by inactivating any of the genes encoding enzymes involved in this pathway, including GMD, Fx, GFR, or FUT8 (FIG. 1B). However, there are no reported examples of targeted gene knockouts in any lepidopteran insect cell line and this approach is technically complicated by the fact that neither the *Spodoptera frugiperda* nor the *Trichoplusia ni* genomes have been sequenced. On the other hand, we have reported many examples of foreign gene knock-ins using both Sf9 (Hollister et al. 1998; Hollister and Jarvis 2001; Hollister et al. 2002; Aumiller et al. 2003; Aumiller et al. 2012; Geisler and Jarvis 2012; Mabashi-Asazuma et al. 2013) and High Five™ (Breitbach and Jarvis 2001) cells, as part of our broader effort to glycoengineer the baculovirus-insect cell system. Thus, we pursued an analogous glycoengineering strategy that involved transforming Sf9 and High Five™ cells with a constitutively expressible *Pseudomonas aeruginosa* Rmd gene. This gene encodes an enzyme that consumes the immediate precursor to GDP-L-fucose to produce GDP-D-rhamnose, which we believed would be a dead-end product in insect cells (FIG. 1B; Rocchetta et al. 1998). Thus, we expected Rmd to block the production of GDP-L-fucose and glycoprotein fucosylation because GDP-L-fucose is required as the donor substrate for this process.

We constructed an expression plasmid encoding Rmd under the transcriptional control of the *Autographa californica* multicapsid nucleopolyhedrovirus (AcMNPV) immediate early 1 (ie1) promoter, as described in Materials and methods. We then co-transfected Sf9 and High Five™ cells with a mixture of this plasmid and an antibiotic-resistance marker and selected polyclonal transformed Sf9 and High Five™ cell subpopulations, which were designated SfRMD and TnRMD, respectively. We assayed both polyclonal transformed cell populations for cell surface fucosylation by staining with *Aleuria aurantia* lectin (AAL), as described in Materials and methods. The results showed that 100% of the parental Sf9 and High Five™ cells were stained, while only 23% of the SfRMD and 33% of the TnRMD cells were stained with AAL (FIG. 4). These results demonstrated that Rmd overexpression significantly reduced glycoprotein fucosylation in insect cells. We subsequently isolated single cell clones from the polyclonal transformed SfRMD and TnRMD populations, identified several that exhibited no detectable AAL cell surface staining, and amplified one of each, designated SfRMD 2B2 and TnRMD 6A6. We then infected Sf9, SfRMD 2B2, High Five™ and TnRMD 6A6 cells with a baculovirus vector encoding a 6×HIS-tagged Fc domain of mouse IgG2a (mIgG2a-Fc) under the control of the baculovirus p6.9 promoter, which is activated during the late phase of infection (Passarelli and Guarino 2007), and affinity-purified the mIgG2a-Fc from the extracellular fractions, as described in Materials and methods. Samples were then treated with peptide-$N^4$-(N-acetyl-β-glucosaminyl)asparagine amidase (PNGase)-F or reaction buffer alone, resolved by SDS-PAGE, transferred to a PVDF membrane, and probed with AAL to detect fucose or with anti-mouse IgG to detect the protein (FIG. 5).

The results of this analysis showed that the mIgG2a-Fc preparations produced by the parental cell lines were AAL-reactive and either completely (Sf9) or partially (High Five™) sensitive to PNGase-F, indicating they were core α1,6- (Sf9) or α1,6- and α1,3- (High Five™) fucosylated, respectively. In contrast, neither of the mIgG2aFc preparations from SfRMD 2B2 or TnRMD 6A6 cells was AAL-reactive, indicating that RMD effectively blocked glycoprotein fucosylation in both cell types. However, we were surprised to find that both of these prototype SfRMD and TnRMD clones recovered strong AAL reactivity after 38 and 35 passages in culture, respectively, indicating that the fucosylation-negative phenotype is unstable in these cells (data not shown). We obtained this same result with other SfRMD and TnRMD clones, which was extremely surprising, because this knock-in approach had been used previously to isolate a stable, fucosylation deficient CHO cell derivative (von Horsten et al. 2010) and because we had previously demonstrated that a transgenic insect cell line transformed with six different transgenes was stable for at least 300 passages in culture (Aumiller et al. 2012). Although we found that they still expressed the Rmd gene at the transcriptional level, we did not expend any further effort to determine how the SfRMD and TnRMD cells recovered their original fucosylation-positive phenotypes. Rather, after finding, much to our surprise, that our insect cell glycoengineering approach was unsuccessful, we began to develop a new approach for blocking glycoprotein fucosylation in the baculovirus-insect cell system.

Assessing a Vector-Based Glycoengineering Strategy for Blocking Glycoprotein Fucosylation In view of the surprising phenotypic instability of SfRMD and TnRMD cells, we abandoned our efforts to glycoengineer the host cell component and focused our attention on the baculoviral vector component of the baculovirus-insect cell system. The baculovirus-insect cell system is a transient expression system in which baculovirus-infected insect cells express the glycoprotein of interest for a period of about 2 days, beginning about a day after infection, when the gene encoding the glycoprotein of interest begins to be expressed during the late or very late phase of infection. Baculovirus-infected cells are typically harvested by about 60-72 hours post-infection because the host cells die and lyse at later times of infection. Given the transient nature of this expression system, we realized that the phenotypic instability observed with long-term constitutive expression of Rmd in the host cells could be overcome by engineering the viral vector to express this enzyme. However, we also realized we would have to design the new vector to express Rmd early in infection, in order to reduce endogenous GDP-L-fucose to low enough levels to block fucosylation before the glycoprotein of interest began to be expressed during a later phase of infection.

To assess our ability to meet these requirements, we isolated a recombinant baculovirus designated AcP(+)IE1-RMD, which encodes Rmd under the control of the AcMNPV ie1 promoter and was expected to express the Rmd gene immediately after baculovirus infection (Guarino and Summers 1986). We then used this virus to examine the impact of immediate early Rmd expression on fucosylation of mIgG2a-Fc. This was accomplished by co-infecting Sf9 or Tni PRO™ cells with equal doses of AcP(+)IE1-RMD and Acp6.9-mIgG2a-Fc, or with Acp6.9-mIgG2a-Fc alone as a control, and then affinity-purifying the mIgG2a-Fc from the extracellular fractions for analysis, as described in Materials and methods. Samples of the purified mIgG2a-Fc were then treated with PNGase-F or reaction buffer alone, resolved by SDS-PAGE, transferred to a PVDF membrane, and probed with AAL to detect fucose, anti-HRP to detect core α1,3-linked fucose, or anti-mouse IgG to detect the protein. The results showed that the control mIgG2a-Fc preparation produced by Sf9 cells infected with Acp6.9-mIgG2a-Fc alone were AAL-reactive (FIG. 6, top panel), indicating it was fucosylated. In addition, PNGase-F pretreatment eliminated its AAL reactivity (FIG. 6, top panel), indicating that it was exclusively core α1,6-fucosylated, because PNGase-F does not remove core α1,3-fucosylated N-glycans (Tretter et al. 1991). This interpretation was supported by the fact that anti-HRP, which recognizes the immunogenic sugar epitope produced by core α1,3-fucosylation, did not react with this mIgG2a-Fc preparation (FIG. 6, middle panel). In contrast, the mIgG2a-Fc preparation from Sf9 cells co-infected with Acp6.9-mIgG2a-Fc and AcP(+)IE1-RMD was not AAL-reactive (FIG. 6, upper panel), indicating it was not fucosylated and, therefore, that baculovirus-mediated Rmd expression blocked core α1,6-fucosylation in Sf9 cells. The mIgG2a-Fc from Tni PRO™ cells infected with Acp6.9-mIgG2a-Fc alone reacted not only with AAL (FIG. 6, top panel), but also with anti-HRP (FIG. 6, middle panel), whether or not it was pre-treated with PNGase-F, indicating that it was core α1,3-fucosylated. This interpretation was supported by the fact that PNGase-F did not detectably alter the electrophoretic mobility of this mIgG2a-Fc preparation (FIG. 6, bottom panel). In contrast, the mIgG2a-Fc from Tni PRO™ cells co-infected with Acp6.9-mIgG2a-Fc and AcP(+)IE1-RMD had no detectable AAL (FIG. 6, top panel) or anti-HRP (FIG. 6, middle panel) reactivity and was sensitive to PNGase-F (FIG. 6, bottom panel). These results indicated that baculovirus-mediated Rmd expression blocked both core α1,6- and core α1,3-fucosylation in Tni PRO™ cells.

To more directly assess the impact of AcP(+)IE1-RMD co-infection on core fucosylation of mIgG2a-Fc, we enzymatically released, permethylated, and analyzed the N-glycans from each mIgG2a-Fc preparation in FIG. 6 by matrix assisted laser desorption ionization-time of flight mass spectrometry (MALDI-TOF MS), as described in Materials and methods. The results indicated that the major N-glycans isolated from the mIgG2a-Fc produced by Sf9 cells infected with Acp6.9-mIgG2a-Fc alone were mono-fucosylated (m/z 1345.7 and 1590.8; FIG. 7A). Based on the results shown in FIG. 6, these are most likely core α1,6-fucosylated N-glycans. In contrast, none of the peaks assigned as fucosylated N-glycans were detected in the mIgG2a-Fc produced by Sf9 cells co-infected with Acp6.9-mIgG2a-Fc and AcP(+)IE1-RMD (FIG. 7B). The major N-glycans isolated from the mIgG2a-Fc produced by Tni PRO™ cells infected with Acp6.9-mIgG2a-Fc alone included mono-, but predominantly di-fucosylated structures (FIG. 7C). While their masses cannot directly reveal the nature of the linkages between the fucose and core N-acetylglucosamine residues in these N-glycans, it is most reasonable to conclude that the di-fucosylated N-glycans have both α1,6- and α1,3-linked fucose residues. Again, none of the peaks assigned as mono- or di-fucosylated N-glycans were detected in the mIgG2a-Fc produced by Tni PRO™ cells co-infected with Acp6.9-mIgG2a-Fc and AcP(+)IE1-RMD (FIG. 7D). Together, the AAL blotting, anti-HRP antibody blotting, and MALDI-TOF MS data clearly demonstrate that baculovirus-mediated expression of Rmd at an early stage of infection can effectively block core α1,6- and α1,3-fucosylation of recombinant glycoproteins expressed later in infection in the baculovirus-insect cell system.

A Novel Baculovirus Vector Designed to Produce Non-Fucosylated Recombinant Glycoproteins While co-infection with multiple baculoviruses is an approach that can be used to co-express two or more different recombinant proteins in insect cells, balanced co-infections can be difficult to achieve, infection with multiple baculoviruses can dramatically reduce recombinant glycoprotein yields, and optimal co-infection conditions must be established for each experiment (Sokolenko et al. 2012). We chose to circumvent these issues by isolating a novel baculovirus vector designed not only to express Rmd immediately after infection, but also to facilitate downstream insertion of genes encoding any glycoprotein of interest for expression at a later time of infection. The experimental design used to isolate this new baculovirus vector, designated AcRMD, included using the ie1-Rmd gene to replace portions of the viral chiA and v-cath genes, which encode a chitinase purported to interfere with secretory pathway function (Hawtin et al. 1997; Kaba et al. 2004; Hitchman et al. 2010) and a cathepsin-like protease that can degrade recombinant proteins of interest (Slack et al. 1995; Kaba et al. 2004; Hitchman et al. 2010), respectively. The complete details of the strategy used to isolate this new vector are given in Materials and methods and genetic maps of the parental viral genome, transfer plasmid, and final baculoviral vector are shown in FIG. 8 and the plasmid map shown in FIG. 14.

AcRMD Produces Non-Fucosylated Recombinant Glycoproteins

To examine the capabilities of the new baculovirus vector described in the preceding section, we isolated two independent daughter recombinants encoding rituximab, an anti-CD20-IgG, with the light and heavy chain genes placed under the independent transcriptional control of dual back-to-back promoters from either the AcMNPV p6.9 or polyhedrin genes (see genetic maps in FIG. 9). We chose rituximab as the model glycoprotein for this work because it is a biotechnologically relevant therapeutic antibody that is core α1,6-fucosylated in mammalian cells, has enhanced effector function in the absence of fucosylation, and has been used to treat rheumatoid arthritis and non-Hodgkin's lymphoma in human patients (Li et al. 2013; reviewed by Lim et al. 2010). We isolated AcRMD daughters encoding anti-CD20-IgG under the control of either the p6.9 or the polyhedrin promoters because the latter is activated during the very late phase of infection and is widely used to drive recombinant gene expression in baculoviral vectors, whereas the former is activated somewhat earlier, during the late phase of infection, and can sometimes provide higher efficiencies of protein secretion (Sridhar et al. 1993; Rankl et al. 1994; Bozon et al. 1995; Kost et al. 1997; Toth et al. 2011). We then infected Sf9 cells with these viruses, designated Ac-αCD20-IgG, Acp6.9-αCD20-IgG, AcRMD-αCD20-IgG, or AcRMDp6.9-αCD20-IgG, and measured the relative amounts of anti-CD20-IgG produced and secreted by viruses encoding the heavy and light chains under the control of the two different promoters. The results showed that all four baculovirus vectors induced production and secretion of the anti-CD20-IgG heavy and light chains (FIG. 10). The results also showed that cells infected with the baculovirus vectors encoding anti-CD20-IgG under the control of the late p6.9 promoters secreted higher levels of heavy and light chains than those infected with the baculovirus encoding this product under the control of the very late polyhedrin promoters. Together with the lower levels of heavy and light chains observed in the intracellular fraction, these results indicated that the p6.9-based vectors provided higher efficiencies of anti-CD20-IgG secretion than the polyhedrin-based vectors (FIG. 10). Based on these results, we used Acp6.9-αCD20-IgG and AcRMDp6.9-αCD20-IgG for the remainder of the experiments described in this study.

Acp6.9-αCD20-IgG or AcRMDp6.9-αCD20-IgG were used to infect Sf9 or Tni PRO™ cells and the anti-CD20-IgG secreted by all four virus-cell combinations was affinity purified, resolved by SDS-PAGE under reducing or non-reducing conditions with commercial human IgG as a control, and then stained with Coomassie Brilliant Blue. The results showed that each anti-CD20-IgG preparation analyzed under reducing conditions contained approximately equal proportions of the heavy and light chains, indicating that each virus-cell combination produced and secreted properly assembled forms of anti-CD20-IgG (FIG. 11). This was confirmed by SDS-PAGE analysis under non-reducing conditions, which revealed that each anti-CD20-IgG preparation migrated with relative electrophoretic mobilities that were consistent with their calculated molecular weights (~165 kDa) and comparable to the human IgG control (FIG. 11). Further analysis showed that the anti-CD20-IgG heavy chain produced by Acp6.9-αCD20-IgG-infected Sf9 cells was PNGase-F-sensitive and AAL-reactive, indicating that it had core α1,6-fucosylated N-glycans (FIG. 12). In contrast, the anti-CD20-IgG heavy chain produced by AcRMDp6.9-αCD20-IgG-infected Sf9 cells was PNGase-F-sensitive, but not AAL-reactive, indicating that it had non-fucosylated N-glycans (FIG. 12). The anti-CD20-IgG heavy chain produced by Acp6.9-αCD20-IgG-infected Tni PRO™ cells was PNGase-F-resistant and AAL-reactive, presumably because its N-glycans were α1,3-fucosylated in these cells (FIG. 12). In contrast, the anti-CD20-IgG heavy chain produced by AcRMDp6.9-αCD20-IgG-infected Tni PRO™ cells was PNGase-F-sensitive and did not react with AAL (FIG. 12). Together, these results strongly suggested that early expression of Rmd by the vectors derived from the AcRMD parent blocked core fucosylation of anti-CD20-IgG in the baculovirus-insect cell system.

To confirm and extend these results using a more direct approach, we enzymatically released, permethylated, and used MALDI-TOF MS to analyze the N-glycans from anti-CD20-IgG preparations purified from various virus-cell combinations, as described in Materials and methods. The N-glycan profiles observed with the anti-CD20-IgG from Acp6.9-αCD20-IgG-infected Sf9 cells included four peaks assigned as mono-fucosylated N-glycans (m/z 1345.7, 1590.8, 1794.9, and 1999.0; FIG. 13A), which are presumably core α1,6-fucosylated, based on the PNGase-F-sensitivity of the heavy chain (FIG. 12). In contrast, none of these mono-fucosylated peaks were detected among the N-glycans isolated from the anti-CD20-IgG produced by AcRMDp6.9-αCD20-IgG-infected Sf9 cells (FIG. 13B). In addition, the loss of the fucosylated N-glycan peaks was accompanied by increased N-glycan peaks corresponding to their non-fucosylated counterparts, especially those with m/z values of 1171.6 and 1416.7 (FIGS. 13A and 13B). The N-glycan profiles observed with the anti-CD20-IgG from Acp6.9-αCD20-IgG-infected Tni PRO™ cells included seven peaks assigned as fucosylated N-glycans, three of which were mono-fucosylated (m/z 1345.7, 1590.8, and 1835.9) and four of which were di-fucosylated (m/z 1315.7, 1519.8, 1764.9, and 2173.1; FIG. 13C). The di-fucosylated N-glycans represented ~65.5% of total (FIG. 13C), reflecting the high levels of core α1,3-fucosylation observed in Tni PRO™ and High Five™ cells (FIG. 2). In contrast, no fucosylated N-glycans were detected in the profiles obtained with the anti-CD20-IgG produced by AcRMDp6.9-αCD20-IgG-infected Tni PRO™ cells (FIG. 13D) and, again, the loss of fucosylated N-glycan peaks was accompanied by increases in the N-glycan peaks corresponding to their non-fucosylated counterparts (FIGS. 13C and 13D; m/z 1171.6 and 1416.7). It is tempting to speculate that the large increase in the m/z 1416.7 peak, which represents an N-glycan with a single N-acetylglucosamine residue on its non-reducing end, reflects the relative inability of Sf-FDL (Geisler et al., 2008) to remove this sugar from non-fucosylated substrates. Regardless, the mass spectrometric analysis of the N-glycans isolated from anti-CD20-IgG produced by the Rmd-negative or Rmd-positive baculovirus vectors clearly demonstrated that the new vector designed to express Rmd early in infection can block recombinant glycoprotein fucosylation in the baculovirus-insect cell system.

Discussion

Core α1,3-fucosylation generates an immunogenic sugar epitope that has significantly hindered development and utilization of insect-based systems, including the baculovirus-insect cell system for the production of recombinant glycoproteins for therapeutic drug and diagnostic applications in human medicine. In addition, core α1,6-fucosylation of certain types of recombinant antibodies in this system and others represses their effector functions. Thus, the basic purpose of this study was to develop new tools that could be used to produce non-fucosylated recombinant glycoproteins, including antibodies, in insect-based systems, including the baculovirus-insect cell system.

It is well established that High Five™, which is a widely used insect cell line derived from *Trichoplusia ni*, produces high levels of immunogenic core α1,3-fucosylated N-glycans. In the first part of this study, we showed that Tni PRO™ cells, also derived from *Trichoplusia ni*, produce high levels of immunogenic core α1,3-fucosylated N-glycans, as well. This finding is relevant because High Five™ and Tni PRO™ cells can potentially produce recombinant glycoproteins at higher levels than other insect cell lines (Davis et al. 1992; Krammer et al. 2010). Tni PRO™ cells have the additional advantage of being easier to culture in suspension and, unlike High Five™ cells (Dee et al. 1997; Taticek et al. 1997; Savary et al. 1999), are directly transferrable without adaptation from serum containing to serum-free ESF 921 medium (unpublished observations). In the course of this study, we found that a mouse IgG2a-Fc domain and a therapeutic anti-CD20-IgG were both core α1,6-fucosylated when produced in Sf9 cells and core α1,6- and core α1,3-fucosylated when produced in High Five™ or Tni PRO™ cells. While these results were not surprising in view of previous literature, they were important because they clearly justified an effort to block recombinant glycoprotein fucosylation in the baculovirus-insect cell system.

To accomplish this goal, we focused on a bacterial enzyme, Rmd, which consumes the direct precursor to GDP-L-fucose and was expected to block recombinant glycoprotein fucosylation in insect cell lines. In fact, previous work had shown that core α1,6-fucosylation could be blocked in CHO cells genetically transformed to overexpress this enzyme (von Horsten et al. 2010). Thus, our analogous initial approach was to transform Sf9 and High Five™ cells to constitutively express Rmd under the control of the AcMNPV ie1 promoter. We successfully isolated Sf9 and High Five™ cell subclones that initially had fucosylation-negative phenotypes and were able to produce a non-fucosylated recombinant glycoprotein. However, this phenotype was unstable, as both insect cell lines reverted to fucosylation-positive phenotypes after a relatively small number of passages in culture. This completely surprising result revealed that the cell engineering approach previously used to block core α1,6-fucosylation in CHO cells cannot be successfully applied to block core α1,6- and/or α1,3-fucosylation in insect cell systems. Thus, we sought to develop a new approach that involved glycoengineering the baculovirus vector, rather than the host.

We assessed the efficacy of our proposed vector engineering approach by co-infecting Sf9 and Tni PRO™ cells with separate baculovirus vectors encoding Rmd under the control of the ie1 promoter or mIgG2a-Fc under the control of the polyhedrin promoter. Analysis of the resulting N-glycosylation patterns showed that early expression of Rmd could block core fucosylation of mIgG2a-Fc produced at a later time of infection. This encouraged us to create a novel baculovirus vector designed not only to express Rmd immediately after infection, but also to enable quick and efficient isolation of daughter vectors capable of expressing any recombinant glycoprotein of interest at later times after infection. After isolating and characterizing AcRMD, the parent baculovirus vector, we used it to isolate a daughter encoding the heavy and light chains of rituximab, an anti-CD20-IgG, under the control of dual, back-to-back p6.9 promoters. We chose the late p6.9, rather than the very late polyhedrin promoter to drive expression of this biotechnologically relevant recombinant glycoprotein because we found that it provided a higher efficiency of IgG secretion. Finally, we showed that this novel baculovirus vector could be used to produce recombinant anti-CD20-IgG with no detectable core α1,6- or α1,3-fucosylation. This conclusion was based on results obtained from several different methods of N-glycan analysis, including endoglycosidase treatments, lectin blotting assays, and MALDI-TOF MS profiling. It is important to note that our MALDI-TOF MS profiling results indicating there were no detectable fucosylated N-glycans on the recombinant anti-CD20-IgG produced by the Rmd-positive baculovirus vector were obtained using N-glycans isolated with a highly active form of PNGase-A (PNGaseAr; New England Biolabs), which effectively removes core α1,3-fucosylated structures, and with glycan detection levels in the picomolar range. It is also important to note that our MALDI-TOF MS results revealed no detectable N-glycans containing any deoxyhexose, indicating that GDP-rhamnose is a dead-end product that cannot be utilized for N-glycan modification in the baculovirus-insect cell system.

There are clear advantages to engineering the baculovirus vector, rather than host cell lines to block recombinant glycoprotein fucosylation in baculovirus-insect cell systems. One is that any investigator familiar with these systems can use the new AcRMD vector in conjunction with an established linearized viral DNA (Kitts and Possee 1993) approach for homologous recombination with familiar, even pre-existing baculovirus transfer plasmids to efficiently isolate daughter baculovirus vectors encoding their favorite recombinant glycoprotein. Another is that the resulting daughter vectors can be used to produce non-fucosylated forms of that product in standard, familiar, commercially available insect cell lines, such as Sf9, Sf21, High Five™, Tni PRO™, Ea4, S2, or S2R+, even if the investigators favorite cell line normally produces high levels of α1,3-fucosylated N-glycans. This eliminates the need to maintain specialized cell lines transformed to block recombinant glycoprotein fucosylation, which might require different growth media and/or conditions and have different growth properties, all of which complicate routine cell culture operations. Overall, it is highly advantageous to be able to produce non-fucosylated recombinant glycoproteins by simply replacing the recombinant baculovirus used for standardized production runs with its AcRMD counterpart, without having to alter or re-optimize existing protocols. Most importantly, engineering the virus eliminates the problem of genetic instability associated with engineering the insect cell lines, because low passage virus stocks can be produced, checked, and stored in a biologically inert state. In contrast, cell lines transformed to constitutively express Rmd must be maintained in culture and, therefore, subjected to constant selective pressure, which can drive loss of the fucosylation-negative phenotype, as observed in this study. Mammalian cell expression systems engineered to produce non-fucosylated recombinant glycoproteins, such as FG1, CHO SM 3G1, CHO $FUT8^{-/-}$, RMD-CHO, and CHO-DUKX (Imai-Nishiya et al. 2007; Kanda et al. 2007; Malphettes et al. 2010; von Horsten et al. 2010; Zhong et al. 2012), are also subject to the potential problem of long-term instability. In addition, mammalian cells have a salvage pathway that can produce GDP-L-fucose using exogenous fucose, which is a common contaminant of many cell culture components. This salvage pathway can rescue recombinant glycoprotein fucosylation in all mammalian cell lines engineered to eliminate this modification except the FUT8 knockout line. This is unlikely to be a problem in the baculovirus-insect cell system because insects do not appear to encode the enzymes involved in the salvage pathways for GDP-L-fucose biosynthesis.

Arguably, the most important feature of the novel baculovirus vector described in this study is its ability to eliminate the immunogenic sugar epitope resulting from core α1,3-fucosylation of recombinant glycoproteins. This will enable investigators to exploit the potentially higher productivity of insect cell lines derived from *Trichoplusia ni* for recombinant glycoprotein manufacturing (Davis et al. 1992; Krammer et al. 2010). It will also expand the utility of the baculovirus-insect cell system to include production of recombinant glycoproteins for human clinical applications, including therapeutics and diagnostics. Historically, the production of recombinant glycoproteins for therapeutic use in humans has not been a legitimate application of the baculovirus-insect cell system. This study shifts this paradigm because the new baculovirus vector described herein can block core α1,3-fucosylation in insect cell lines glycoengineered to produce humanized, terminally sialylated N-glycans. The combination of these emerging tools constitutes a novel baculovirus-insect cell platform that can be used to manufacture safe and efficacious glycoproteins for human therapy.

Another important feature of the novel baculovirus vector described in this study is its ability to block core α1,6-fucosylation, which is a common modification of a conserved N-glycan on the Fc domain that represses the effector functions of certain types of therapeutic antibodies. As noted above, core α1,6-fucosylation has been blocked in other expression systems in efforts to produce therapeutic antibodies with enhanced effector functions and, therefore, higher efficacy at lower doses (reviewed by Yamane-Ohnuki and Satoh 2009). Sf9 and Tni PRO™ cells infected with the AcRMD daughter vector encoding anti-CD20-IgG produced a non-fucosylated form of this antibody, which is expected to have enhanced effector function, based on a significant body of previous literature (Shields et al. 2002; Shinkawa et al. 2003; Li et al. 2013; reviewed by Lim et al. 2010; Owen and Stewart 2012). Moreover, while many recombinant antibodies have been produced in the baculovirus-insect cell system (reviewed by Cérutti and Golay 2012), most were expressed using dual, back-to-back, very late polyhedrin and p10 promoters to express the heavy and light chains and the heavy chain product. In this study, we found that expression of the heavy and light chains under the control of dual, back-to-back, late p6.9 promoters separated by the second intron from the *Drosophila* white gene provided a higher secretion efficiency than the analogous arrangement of very late polyhedrin promoters (FIG. 10). This result is consistent with those obtained in similar studies on the relationship between the timing of promoter activation and the efficiency of recombinant glycoprotein processing (Sridhar et al. 1993; Rankl et al. 1994; Bozon et al. 1995; Kost et al. 1997; Toth et al. 2011).

REFERENCES

Ailor E, Takahashi N, Tsukamoto Y, Masuda K, Rahman B A, Jarvis D L, Lee Y C, Betenbaugh M J, 2000. N-glycan patterns of human transferrin produced in *Trichoplusia ni* insect cells: effects of mammalian galactosyltransferase. Glycobiology. 10:837-847.

Altmann F, 2007. The role of protein glycosylation in allergy. Int Arch Allergy Immunol. 142:99-115.

Aumiller J J, Hollister J R, Jarvis D L, 2003. A transgenic insect cell line engineered to produce CMP-sialic acid and sialylated glycoproteins. Glycobiology. 13:497-507.

Aumiller J J, Mabashi-Asazuma H, Hillar A, Shi X, Jarvis D L, 2012. A new glycoengineered insect cell line with an inducibly mammalianized protein N-glycosylation pathway. Glycobiology. 22:417-428.

Ausabel, F, 1994-1999. Current Protocols in Molecular Biology. John Wiley & Sons, New York, N.Y.

Bao S, Cagan R, 2006. Fast cloning inverted repeats for RNA interference. RNA. 12:2020-2024.

Blake M S, Johnston K H, Russell-Jones G J, Gotschlich E C, 1984. A rapid, sensitive method for detection of alkaline phosphatase-conjugated anti-antibody on Western blots. Analyt Biochem. 136:175-179.

Blank S, Michel Y, Seismann H, Plum M, Greunke K, Grunwald T, Bredehorst R, Ollert M, Braren I, Spillner E, 2011. Evaluation of different glycoforms of honeybee venom major allergen phospholipase A2 (Api m 1) produced in insect cells. Prot Pept Lett. 18:415-422.

Bongiovanni A, Romancino D P, Campos Y, Paterniti G, Qiu X, Moshiach S, Di F V, Vergani N, Ustek D, d'Azzo A, 2012. Alix protein is substrate of Ozz-E3 ligase and modulates actin remodeling in skeletal muscle. J Biol Chem. 287:12159-12171.

Bourhis E, Tam C, Franke Y, Bazan J F, Ernst J, Hwang J, Costa M, Cochran A G, Hannoush R N, 2010. Reconstitution of a frizzled8•Wnt3a•LRP6 signaling complex reveals multiple Wnt and Dkkl binding sites on LRP6. J Biol Chem. 285:9172-9179.

Bozon V, Remy J J, Pajot-Augy E, Couture L, Biache G, Severini M, Salesse R, 1995. Influence of promoter and signal peptide on the expression and secretion of recombinant porcine L H extracellular domain in baculovirus/lepidopteran cells or the caterpillar system. J Mol Endocrinol. 14:277-284.

Breitbach K, Jarvis D L, 2001. Improved glycosylation of a foreign protein by Tn-5B1-4 cells engineered to express mammalian glycosyltransferases. Biotechnol Bioeng. 74:230-239.

Cary L C, Goebel M, Corsaro B G, Wang H G, Rosen E, Fraser M J. 1989. Transposon mutagenesis of baculoviruses: analysis of *Trichoplusia ni* transposon IFP2 insertions within the FP-locus of nuclear polyhedrosis viruses. Virology. 172(1):156-69.

Cérutti M, Golay J, 2012. Lepidopteran cells, an alternative for the production of recombinant antibodies? MAbs. 4:294-309.

Chang G D, Chen C J, Lin C Y, Chen H C, Chen H, 2003. Improvement of glycosylation in insect cells with mammalian glycosyltransferases. J Biotechnol. 102:61-71.

Davis T R, Trotter K M, Granados R R, Wood H A, 1992. Baculovirus expression of alkaline phosphatase as a reporter gene for evaluation of production, glycosylation and secretion. Nat Biotechnol. 10:1148-1150.

Dee K U, Shuler M L, Wood H A, 1997. Inducing single-cell suspension of BTI-TN5B1-4 insect cells: I. The use of sulfated polyanions to prevent cell aggregation and enhance recombinant protein production. Biotechnol Bioeng. 54:191-205.

Dell A, Reason A J, Khoo K H, Panico M, McDowell R A, Morris H R, 1994. Mass spectrometry of carbohydrate-containing biopolymers. Meth Enzymol. 230:108-132.

Elvin J G, Couston R G, van C F, 2013. Therapeutic antibodies: market considerations, disease targets and bioprocessing. Int J Pharm. 440:83-98.

Fabini G, Freilinger A, Altmann F, Wilson I B, 2001. Identification of core α1,3-fucosylated glycans and cloning of the requisite fucosyltransferase cDNA from *Drosophila melanogaster*. Potential basis of the neural anti-horseadish peroxidase epitope. J Biol Chem. 276:28058-28067.

Ferrara C, Brunker P, Suter T, Moser S, Puntener U, Umana P, 2006. Modulation of therapeutic antibody effector functions by glycosylation engineering: influence of Golgi enzyme localization domain and co-expression of heterologous β1,4-N-acetylglucosaminyltransferase III and Golgi alpha-mannosidase II. Biotechnol Bioeng. 93:851-861.

Fotisch K, Vieths S, 2001. N- and O-linked oligosaccharides of allergenic glycoproteins. Glycoconj J. 18:373-390.

Geisler C, Aumiller J J, Jarvis D L, 2008. A fused lobes gene encodes the processing β-N-acetylglucosaminidase in Sf9 cells. J Biol Chem. 283:11330-11339.

Geisler C, Jarvis D L, 2012. Innovative use of a bacterial enzyme involved in sialic acid degradation to initiate sialic acid biosynthesis in glycoengineered insect cells. Metabol Engr. 14:642-652.

Grossman, G. L., Rafferty, C. S., Fraser, M. J., Benedict, M. Q. 2000. The piggyback element is capable of precise excision and transposition in cells and embryos of the mosquito: *Anopheles gambiae*. Insect Biochem Molecular Biology. 10:909-914.

Guarino L A, Summers M D, 1986. Functional mapping of a trans-activating gene required for expression of a baculovirus delayed-early gene. J Virol. 57:563-571.

Hancock K, Narang S, Pattabhi S, Yushak M L, Khan A, Lin S C, Plemons R, Betenbaugh M J, Tsang V C, 2008. False positive reactivity of recombinant, diagnostic, glycoproteins produced in High Five insect cells: effect of glycosylation. J Immunol Meth. 330:130-136.

Handler, A., McCombs, S., Fraser, M., Saul, S. 1998. The lepidopteran transposon vector, piggyBac, mediates germ-line transformation in the Mediterranean fruit fly. Proc. Natl. Acad. Sci. 95:7520-7525.

Handler, J. (ed). The TTAA-specific family of transposable elements. Insect transgenesis: Methods and Applications. 1999. CRC Press. Orlando, Fla.

Hawtin R E, Zarkowska T, Arnold K, Thomas C J, Gooday G W, King L A, Kuzio J A, Possee R D, 1997. Liquefaction of *Autographa californica* nucleopolyhedrovirus-infected insects is dependent on the integrity of virus-encoded chitinase and cathepsin genes. Virology. 238: 243-253.

He C H, Lee C G, Dela C C S, Lee C M, Zhou Y, Ahangari F, Ma B, Herzog E L, Rosenberg S A, Li Y, Nour A M, Parikh C R, Schmidt I, Modis Y, Cantley L, Elias J A, 2013. Chitinase 3-like 1 regulates cellular and tissue responses via IL-13 receptor α2. Cell Rep. 4:830-841.

Hill D R, Aumiller J J, Shi X, Jarvis D L, 2006. Isolation and analysis of a baculovirus vector that supports recombinant glycoprotein sialylation by SfSWT-1 cells cultured in serum-free medium. Biotechnol Bioengr. 95:37-47.

Hillar A, Jarvis D L, 2010. Re-visiting the endogenous capacity for recombinant glycoprotein sialylation by baculovirus-infected Tn-4h and DpN1 cells. Glycobiology. 20:1323-1330.

Hitchman R B, Possee R D, Siaterli E, Richards K S, Clayton A J, Bird L E, Owens R J, Carpentier D C, King F L, Danquah J O, Spink K G, King L A, 2010. Improved expression of secreted and membrane-targeted proteins in insect cells. Biotechnol Appl Biochem. 56:85-93.

Hollister J R, Shaper J H, Jarvis D L, 1998. Stable expression of mammalian β1,4-galactosyltransferase extends the N-glycosylation pathway in insect cells. Glycobiology. 8:473-480.

Hollister J R, Jarvis D L, 2001. Engineering lepidopteran insect cells for sialoglycoprotein production by genetic transformation with mammalian β1,4-galactosyltransferase and α2,6-sialyltransferase genes. Glycobiology. 11:1-9.

Hollister J R, Grabenhorst E, Nimtz M, Conradt H, Jarvis D L, 2002. Engineering the protein N-glycosylation pathway in insect cells for production of biantennary, complex N-glycans. Biochemistry. 41:15093-15104.

Horn C, Offen N, Nystedt S, Hacker U, Wimmer E A., 2003. piggyBac-based insertional mutagenesis and enhancer detection as a tool for functional insect genomics. Genetics. 163(2):647-61.

Imai-Nishiya H, Mori K, Inoue M, Wakitani M, lida S, Shitara K, Satoh M, 2007. Double knockdown of α1,6-fucosyltransferase (FUT8) and GDP-mannose 4,6-dehydratase (GMD) in antibody-producing cells: a new strategy for generating fully non-fucosylated therapeutic antibodies with enhanced ADCC. BMC Biotechnol. 7:84.

Jarvis D L, Fleming J A, Kovacs G R, Summers M D, Guarino L A, 1990. Use of early baculovirus promoters for continuous expression and efficient processing of foreign gene products in stably transformed lepidopteran cells. Nat Biotechnol. 8:950-955.

Jarvis D L, Weinkauf C, Guarino L A, 1996. Immediate-early baculovirus vectors for foreign gene expression in transformed or infected insect cells. Prot Expr Purif. 8:191-203.

Jarvis D L, Finn E E, 1996. Modifying the insect cell N-glycosylation pathway with immediate early baculovirus expression vectors. Nat Biotechnol. 14:1288-1292.

Jarvis D L, Howe D, Aumiller J J, 2001. Novel baculovirus expression vectors that provide sialylation of recombinant glycoproteins in lepidopteran insect cells. J Virol. 75:6223-6227.

Jarvis D L, 2009. Baculovirus-insect cell expression systems. Meth Enzymol. 463:191-222.

Jefferis R, 2009. Glycosylation as a strategy to improve antibody-based therapeutics. Nat Rev Drug Discov. 8:226-234.

Kaba S A, Salcedo A M, Wafula P O, Vlak J M, van O M M, 2004. Development of a chitinase and v-cathepsin negative bacmid for improved integrity of secreted recombinant proteins. J Virol. Methods. 122:113-118.

Kanda Y, Imai-Nishiya H, Kuni-Kamochi R, Mori K, Inoue M, Kitajima-Miyama K, Okazaki A, Lida S, Shitara K, Satoh M, 2007. Establishment of a GDP-mannose 4,6-dehydratase (GMD) knockout host cell line: a new strategy for generating completely non-fucosylated recombinant therapeutics. J Biotechnol. 130:300-310.

King T P, Sobotka A K, Kochoumian L, Lichtenstein L M, 1976. Allergens of honey bee venom. Arch Biochem Biophys. 172:661-671.

Kitts P A, Possee R D, 1993. A method for producing recombinant baculovirus expression vectors at high frequency. Biotechniques. 14:810-817.

Kost T A, Ignar D M, Clay W C, Andrews J, Leray J D, Overton L, Hoffman C R, Kilpatrick K E, Ellis B, Emerson D L, 1997. Production of a urokinase plasminogen activator-IgG fusion protein (uPA-IgG) in the baculovirus expression system. Gene. 190:139-144.

Krammer F, Schinko T, Palmberger D, Tauer C, Messner P, Grabherr R, 2010. *Trichoplusia ni* cells (High Five) are highly efficient for the production of influenza A virus-like particles: a comparison of two insect cell lines as production platforms for influenza vaccines. Mol Biotechnol. 45:226-234.

Kubelka V, Altmann F, Marz L, 1995. The asparagine-linked carbohydrate of honeybee venom hyaluronidase. Glycoconj J. 12:77-83.

Kwon H J, Abi-Mosleh L, Wang M L, Deisenhofer J, Goldstein J L, Brown M S, Infante R E, 2009. Structure of N-terminal domain of NPC1 reveals distinct subdomains for binding and transfer of cholesterol. Cell. 137: 1213-1224.

Li C, Rossomando A, Wu S L, Karger B L, 2013. Comparability analysis of anti-CD20 commercial (rituximab) and RNAi-mediated fucosylated antibodies by two L C-M S approaches. MAbs. 5:565-575.

Lim S H, Beers S A, French R R, Johnson P W, Glennie M J, Cragg M S, 2010. Anti-CD20 monoclonal antibodies: historical and future perspectives. Haematologica. 95:135-143.

Lobo, N., Li, M., Fraser, M. J., 1999. Transposition of the piggyBac element in embryos of *Drosophila melanogaster, Aedes aegypti* and *Trichoplusia ni*. Mol. Gen. Genetics. 261:803-810.

Lorenzen M D, Berghammer A J, Brown S J, Denell R E, Klingler M, Beeman R W, 2003. piggyBac-mediated germline transformation in the beetle Tribolium castaneum. Insect Mol. Biol. 12(5):433-40.

Mabashi-Asazuma H, Shi X, Geisler C, Kuo C W, Khoo K H, Jarvis D L, 2013. Impact of a human CMP-sialic acid transporter on recombinant glycoprotein sialylation in glycoengineered insect cells. Glycobiology. 23:199-210.

Maeda S, 1989. Gene transfer vectors of a baculovirus, *Bombyx mori* nuclear polyhedrosis virus, and their use for expression of foreign genes in insect cells. In: J. Mitsuhashi, editor. Invertebrate cell system applications, vol. I. Boca Raton (Fla.): CRC Press. p. 167-181.

Malphettes L, Freyvert Y, Chang J, Liu P Q, Chan E, Miller J C, Zhou Z, Nguyen T, Tsai C, Snowden A W, Collingwood T N, Gregory P D, Cost G J, 2010. Highly efficient deletion of FUT8 in CHO cell lines using zinc-finger nucleases yields cells that produce completely nonfucosylated antibodies. Biotechnol Bioengr. 106:774-783. Marchal I, Jarvis D L, Cacan R, Verbert A, 2001. Glycoproteins from insect cells: sialylated or not? Biol Chem. 382:151-159.

Merchant M, Ma X, Maun H R, Zheng Z, Peng J, Romero M, Huang A, Yang N Y, Nishimura M, Greve J, Santell L, Zhang Y W, Su Y, Kaufman D W, Billeci K L, Mai E, Moffat B, Lim A, Duenas E T, Phillips H S, Xiang H, Young J C, Vande W G F, Dennis M S, Reilly D E, Schwall R H, Starovasnik M A, Lazarus R A, Yansura D G, 2013. Monovalent antibody design and mechanism of action of onartuzumab, a MET antagonist with anti-tumor activity as a therapeutic agent. Proc Natl Acad Sci USA. 110:E2987-2996.

Murkhammer, D. W. (ed). 2007. Methods in Molecular Biology: Baculovirus Expression Protocols. Humana Press, Clifton, N.J.

Ngantung F A, Miller P G, Brushett F R, Tang G L, Wang D I, 2006. RNA interference of sialidase improves glycoprotein sialic acid content consistency. Biotechnol Bioengr. 95:106-119.

Okada T, Mara H, Ito R, Nakano M, Matsumoto K, Yamaguchi Y, Taniguchi N, Ikeda Y, 2010. N-Glycosylation engineering of lepidopteran insect cells by the introduction of the β1,4-N-acetylglucosaminyltransferase III gene. Glycobiology. 20:1147-1159.

Owen C, Stewart D A, 2012. Obinutuzumab for the treatment of lymphoproliferative disorders. Exp Op Biol Ther. 12:343-351.

Palmberger D, Rendic D, Tauber P, Krammer F, Wilson I B, Grabherr R, 2011. Insect cells for antibody production: evaluation of an efficient alternative. J Biotechnol. 153: 160-166.

Palmberger D, Wilson I B, Berger I, Grabherr R, Rendic D, 2012. SweetBac: a new approach for the production of mammalianised glycoproteins in insect cells. PLoS One. 7:e34226.

Paschinger K, Staudacher E, Stemmer U, Fabini G, Wilson I B, 2005. Fucosyltransferase substrate specificity and the order of fucosylation in invertebrates. Glycobiology. 15:463-474.

Passarelli A L, Guarino L A, 2007. Baculovirus late and very late gene regulation. Curr Drug Targets. 8:1103-1115.

Prenner C, Mach L, Glossl J, Marz L, 1992. The antigenicity of the carbohydrate moiety of an insect glycoprotein, honey-bee (*Apis mellifera*) venom phospholipase A2. The role of α1,3-fucosylation of the asparagine-bound N-acetylglucosamine. Biochem J. 284:377-380.

Rankl N B, Rice J W, Gurganus T M, Barbee J L, Burns D J, 1994. The production of an active protein kinase C-delta in insect cells is greatly enhanced by the use of the basic protein promoter. Prot Expr Purif 5:346-356.

Rendić D, Klaudiny J, Stemmer U, Schmidt J, Paschinger K, Wilson I B, 2007. Towards abolition of immunogenic structures in insect cells: characterization of a honey-bee (*Apis mellifera*) multi-gene family reveals both an allergy-related core α1,3-fucosyltransferase and the first insect Lewis-histo-blood-group-related antigen-synthesizing enzyme. Biochem J. 402:105-115.

Rhomberg S, Fuchsluger C, Rendic D, Paschinger K, Jantsch V, Kosma P, Wilson I B, 2006. Reconstitution in vitro of the GDP-fucose biosynthetic pathways of *Caenorhabditis elegans* and *Drosophila melanogaster*. FEBS J. 273:2244-2256.

Rocchetta H L, Pacan J C, Lam J S, 1998. Synthesis of the A-band polysaccharide sugar D-rhamnose requires Rmd and WbpW: identification of multiple AlgA homologues, WbpW and ORF488, in *Pseudomonas aeruginosa*. Mol Microbiol. 29:1419-1434.

Rudd P M, Downing A K, Cadene M, Harvey D J, Wormald M R, Weir I, Dwek R A, Rifkin D B, Gleizes P E, 2000. Hybrid and complex glycans are linked to the conserved N-glycosylation site of the third eight-cysteine domain of LTBP-1 in insect cells. Biochemistry. 39:1596-1603.

Satoh M, Iida S, Shitara K, 2006. Non-fucosylated therapeutic antibodies as next-generation therapeutic antibodies. Exp Op Biol Ther. 6:1161-1173.

Sambrook, J., Fritsch, E. F., and Maniatis, T. 1989 Molecular Cloning: A Laboratory Manual, 2nd edition Ed. Cold Spring Harbor Press, Cold Spring Harbor, N.Y.

Savary A C, Georges B, Auriault C, 1999. Adaptation of BTI-TN5B1-4 (high five) insect cells for large-scale production in a stirred bioreactor. Biotechniques. 27:448-450.

Seismann H, Blank S, Braren I, Greunke K, Cifuentes L, Grunwald T, Bredehorst R, Ollert M, Spillner E, 2010. Dissecting cross-reactivity in hymenoptera venom allergy by circumvention of α-1,3-core fucosylation. Mol Immunol. 47:799-808.

Seo N S, Hollister J R, Jarvis D L, 2001. Mammalian glycosyltransferase expression allows sialoglycoprotein production by baculovirus-infected insect cells. Prot Expr Purif. 22:234-241.

Shi X, Harrison R L, Hollister J R, Mohammed A, Fraser M J J, Jarvis D L, 2007. Construction and characterization of new piggyBac vectors for constitutive or inducible expression of heterologous gene pairs and the identification of a previously unrecognized activator sequence in piggyBac. BMC Biotechnol. 7:5.

Shields R L, Lai J, Keck R, O'Connell L Y, Hong K, Meng Y G, Weikert S H, Presta L G, 2002. Lack of fucose on human IgG1 N-linked oligosaccharide improves binding to human FcγRIII and antibody-dependent cellular toxicity. J Biol Chem. 277:26733-26740.

Shinkawa T, Nakamura K, Yamane N, Shoji-Hosaka E, Kanda Y, Sakurada M, Uchida K, Anazawa H, Satoh M, Yamasaki M, Hanai N, Shitara K, 2003. The absence of fucose but not the presence of galactose or bisecting N-acetylglucosamine of human IgG1 complex-type oligosaccharides shows the critical role of enhancing antibody-dependent cellular cytotoxicity. J Biol Chem. 278: 3466-3473.

Slack J M, Kuzio J, Faulkner P, 1995. Characterization of v-cath, a cathepsin L-like proteinase expressed by the baculovirus *Autographa californica* multiple nuclear polyhedrosis virus. J Gen Virol. 76:1091-1098.

Sokolenko S, George S, Wagner A, Tuladhar A, Andrich J M, Aucoin M G, 2012. Co-expression vs. co-infection using baculovirus expression vectors in insect cell culture: Benefits and drawbacks. Biotechnol Adv. 30:766-781.

Sridhar P, Panda A K, Pal R, Talwar G P, Hasnain S E, 1993. Temporal nature of the promoter and not relative strength determines the expression of an extensively processed protein in a baculovirus system. FEBS Lett. 315:282-286.

Sumitani M, Yamamoto D S, Oishi K, Lee J M, Hatakeyama M., 2003. Germline transformation of the sawfly, *Athalia rosae* (Hymenoptera: Symphyta), mediated by a piggyBac-derived vector. Insect Biochem Mol Biol. 33(4):449-58.

Summers M D, Smith G E. 1987. A manual of methods for baculovirus vectors and insect cell culture procedures. Tx Ag Expt Stn Bull No 1555.

Tamura K, Peterson D, Peterson N, Stecher G, Nei M, Kumar S, 2011. MEGA5: molecular evolutionary genetics analysis using maximum likelihood, evolutionary distance, and maximum parsimony methods. Mol Biol Evol. 28:2731-2739.

Taticek R A, McKenna K A, Granados R R, Shuler M L, 1997. Rapid initiation of suspension cultures of *Trichoplusia ni* insect cells (TN 5B-1-4) using heparin. Biotechnol Tech. 11:237-240.

Tomiya N, Howe D, Aumiller J J, Pathak M, Park J, Palter K B, Jarvis D L, Betenbaugh M J, Lee Y C, 2003. Complex-type biantennary N-glycans of recombinant human transferrin from *Trichoplusia ni* insect cells expressing mammalian β-1,4-galactosyltransferase and β-1,2-N-acetylglucosaminyltransferase II. Glycobiology. 13:23-34.

Toth A M, Geisler C, Aumiller J J, Jarvis D L, 2011. Factors affecting recombinant Western equine encephalitis virus glycoprotein production in the baculovirus system. Prot Expr Purif. 80:274-282.

Tretter V, Altmann F, Marz L, 1991. Peptide-$N^4$-(N-acetyl-β-glucosaminyl)asparagine amidase F cannot release glycans with fucose attached α1→3 to the asparagine-linked N-acetylglucosamine residue. Eur J Biochem. 199:647-652.

Usami A, Suzuki T, Nagaya H, Kaki H, Ishiyama S, 2010. Silkworm as a host of baculovirus expression. Curr Pharm Biotechnol. 11:246-250.

Varki A, Gagneux P, 2012. Multifarious roles of sialic acids in immunity. Ann N Y Acad Sci. 1253:16-36.

Vaughn, J. L., R. H. Goodwin, G. J. Tompkins, and P. McCawley. The establishment of two cell lines from the insect *Spodoptera frugiperda* (Lepidoptera: Noctuidae). In Vitro 13:213-217.1977.

von Horsten H H, Ogorek C, Blanchard V, Demmler C, Giese C, Winkler K, Kaup M, Berger M, Jordan I, Sandig V, 2010. Production of non-fucosylated antibodies by co-expression of heterologous GDP-6-deoxy-D-lyxo-4-hexulose reductase. Glycobiology. 20:1607-1618.

Wagner R, Liedtke S, Kretzschmar E, Geyer H, Geyer R, Klenk H D, 1996. Elongation of the N-glycans of fowl plague virus hemagglutinin expressed in *Spodoptera frugiperda* (Sf9) cells by coexpression of human β1,2-N-acetylglucosaminyltransferase I. Glycobiology. 6:165-175.

Wickham T J, Davis T, Granados R R, Shuler M L, Wood H A, 1992. Screening of insect cell lines for the production of recombinant proteins and infectious virus in the baculovirus expression system. Biotechnol Progr. 8:391-396.

Wu, W., Zhang, H. 1997. Methods in Gene Biotechnology. CRC Press. New York, N.Y.

Yamane-Ohnuki N, Kinoshita S, Inoue-Urakubo M, Kusunoki M, Iida S, Nakano R, Wakitani M, Niwa R, Sakurada M, Uchida K, Shitara K, Satoh M, 2004. Establishment of FUT8 knockout Chinese hamster ovary cells: an ideal host cell line for producing completely defucosylated antibodies with enhanced antibody-dependent cellular cytotoxicity. Biotechnol Bioengr. 87:614-622.

Yamane-Ohnuki N, Satoh M, 2009. Production of therapeutic antibodies with controlled fucosylation. MAbs. 1:230-236.

Yun E Y, Goo T W, Kim S W, Choi K H, Hwang J S, Kang S W, Kwon O Y, 2005. Galatosylation and sialylation of mammalian glycoproteins produced by baculovirus-mediated gene expression in insect cells. Biotechnol Lett. 27:1035-1039.

Zhong X, Cooley C, Seth N, Juo Z S, Presman E, Resendes N, Kumar R, Allen M, Mosyak L, Stahl M, Somers W, Kriz R, 2012. Engineering novel Lecl glycosylation mutants in CHO-DUKX cells: molecular insights and effector modulation of N-acetylglucosaminyltransferase I. Biotechnol Bioengr. 109:1723-1734.

While certain of the preferred embodiments of the present invention have been described and specifically exemplified above, it is not intended that the invention be limited to such embodiments. Various modifications may be made thereto without departing from the scope of the present invention, as set forth in the following claims.

What is claimed is:

1. A method for production of a non-fucosylated protein in insect larvae, comprising a) providing insect larvae;

b) introducing a baculovirus comprising at least one nucleic acid molecule encoding the enzyme GDP-4-dehydro-6-deoxy-D-mannose reductase (RMD) operably driven by an immediate early expression control sequence for expression immediately after infection or an inducible promoter, thereby stabilizing inhibition of fucosylation, and at least one additional nucleic acid molecule encoding at least one protein of interest driven by an expression control sequence active later in infection, thereby producing non-fucosylated proteins, wherein said additional nucleic acid is present on the same baculovirus encoding RMD or is present on a second baculovirus vector;

c) incubating under conditions wherein GDP-4-dehydro-6-deoxy-D-mannose reductase blocks the production of GDP-L-fucose, and said at least one protein of interest is produced lacking fucose; and d) isolating said protein of interest, wherein said RMD encoding nucleic acid is the reverse complement of nucleotides 10034-10948 of SEQ ID NO: 1.

2. The method of claim 1, wherein said nucleic acid molecule encoding the enzyme RMD is operably driven by an immediate early expression control sequence for expression immediately after infection.

3. The method of claim 2, wherein said immediate early expression control sequence comprises the ie1 promoter.

4. The method of claim 3, wherein said expression control sequence active later in infection comprises the p6.9 promoter.

5. A method for producing at least one protein of interest lacking fucose, comprising a) providing insect cells;

b) introducing a baculovirus comprising at least one nucleic acid molecule encoding the enzyme GDP-4-dehydro-6-deoxy-D-mannose reductase (RMD) operably driven by an immediate early expression control sequence for expression immediately after infection or an inducible promoter, thereby stabilizing inhibition of fucosylation, and at least one additional nucleic acid molecule encoding at least one protein of interest driven by an expression control sequence active later in infection, thereby producing non-fucosylated proteins, wherein said additional nucleic acid is present on the same baculovirus encoding RMD or is present on a second baculovirus vector;

c) incubating under conditions wherein GDP-4-dehydro-6-deoxy-D-mannose reductase blocks the production of GDP-L-fucose, and said at least one protein of interest is produced lacking fucose; and d) isolating said at least one protein of interest, wherein said RMD encoding nucleic acid is the reverse complement of nucleotides 10034-10948 of SEQ ID NO: 1.

6. The method of claim 5, wherein said RMD enzyme and said protein of interest are encoded by a single recombinant baculoviral vector and expressed sequentially at earlier and later times of infection.

7. The method of claim 5, wherein said nucleic acid encoding said enzyme and said protein of interest are on separate baculovirus vectors and expressed sequentially at earlier and later times of infection.

8. The method of claim 5, wherein said protein of interest is a therapeutic protein.

9. The method of claim 5, wherein said baculovirus vector comprises SEQ ID NO: 1.

10. The method of claim 5, wherein said baculovirus vector comprises SEQ ID NO: 1, wherein nucleotides 845-1564 are deleted.

11. The method of claim 5, wherein said expression control sequence active later in infection comprises the p6.9 promoter.

12. The method of claim 5, wherein said immediate early control sequence comprises a promoter selected from the group consisting of ie1, ie2, ie0, etl, and gp64, insect actin, tubulin, a ubiquitin promoter; RSV promoter, copia, gypsy promoter and a cytomegalovirus IE promoter.

13. The method of claim 5, wherein said inducible promoter is selected from the group consisting of baculovirus delayed early, late, and very late promoters, an hsp70 promoter, a metallothionein promoter and a tetracycline-regulated promoter.

14. The method of claim 5, wherein said expression control sequence active later in infection comprises a promoter selected from the group consisting of a promoter from baculovirus delayed early, late, and very late promoters.

15. The method of claim 5, wherein said immediate early expression control sequence comprises a promoter and an enhancer element that increases activity of said promoter.

16. The method of claim 15, wherein said enhancer is hr5.

17. The method of claim 5, wherein said protein of interest is selected from the group consisting of an antibody, a subunit vaccine, an antibiotic, a cytokine, an anticoagulant, a viral antigen, an enzyme, a hormone, and a blood clotting factor.

18. The method of claim 5, wherein said insect cells are selected from the group consisting of Sf9, Sf21, Tn368, BTI-Tn-5B1-4, Ea4, Ao38, BmN, S2, and S2R+.

19. The method of claim 5, wherein said nucleic acid molecule encoding the enzyme RMD is operably driven by an immediate early expression control sequence for expression immediately after infection.

20. The method of claim 19, wherein said immediate early expression control sequence comprises the ie1 promoter.

21. The method of claim 20, wherein said expression control sequence active later in infection comprises the p6.9 promoter.

* * * * *